(12) United States Patent
Rosner et al.

(10) Patent No.: US 10,888,569 B1
(45) Date of Patent: Jan. 12, 2021

(54) METHODS AND COMPOSITIONS FOR TREATING CANCER

(71) Applicant: THE UNIVERSITY OF CHICAGO, Chicago, IL (US)

(72) Inventors: Marsha Rosner, Chicago, IL (US); Jiyoung Lee, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/005,052

(22) Filed: Jun. 11, 2018

Related U.S. Application Data

(60) Provisional application No. 62/517,626, filed on Jun. 9, 2017.

(51) Int. Cl.

| | |
|---|---|
| *A61K 31/555* | (2006.01) |
| *A61P 35/00* | (2006.01) |
| *A61K 31/155* | (2006.01) |
| *A61K 9/00* | (2006.01) |
| *A61K 31/352* | (2006.01) |
| *A61K 31/357* | (2006.01) |

(52) U.S. Cl.
CPC ......... *A61K 31/555* (2013.01); *A61P 35/00* (2018.01); *A61K 9/0019* (2013.01); *A61K 9/0053* (2013.01); *A61K 31/155* (2013.01); *A61K 31/352* (2013.01); *A61K 31/357* (2013.01); *A61K 2300/00* (2013.01)

(58) Field of Classification Search
CPC ............... A61K 31/555; A61K 31/155; A61K 2300/00; A61P 35/00
See application file for complete search history.

(56) References Cited

U.S. PATENT DOCUMENTS

| | | | |
|---|---|---|---|
| 2013/0253007 | A1 | 9/2013 | Kasiss et al. |
| 2016/0078167 | A1 | 3/2016 | Rosner et al. |
| 2018/0104232 | A1 | 4/2018 | Rosner et al. |

FOREIGN PATENT DOCUMENTS

| | | | |
|---|---|---|---|
| WO | WO9735569 | * | 10/1997 |

OTHER PUBLICATIONS

Lim et al., Hemin inhibits cyclin D1 and IGF-1 expression via STAT5b under hypoxia in ERalpha-negative MDA-MB-231 breast cancer cells. International J. of Oncology, vol. 36, 1243-1251 (Year: 2010).*
Yang et al., KR 2011083032, Heme-iron for preventing and treating breast cancer. Abstract (Year: 2011).*
Yang et al., KR 2010083579, Hemin for preventing and treating breast cancers. Abstract (Year: 2010).*
Dowling et al., Metformin inhibits mammalian target of rapamycin-dependent translation initiation in breast cancer cells. Cancer Res., vol. 67, 10804-10812 (Year: 2007).*
Wandan-Alaswad et al., Metformin attenuates transforming growth factor beta (TGF-beta) mediated oncogenesis in mesenchymal stem-like/claudin-low triple negative breast cancer. Cell Cycle, vol. 15(8), 1046-1059 (Year: 2016).*
Aletaha et al., Therapeutic effects of bach1 siRNA on human breast adenocarcinoma cell line. Biomedicine & Pharmacotherapy, vol. 88, 34-42 (Year: 2017).*
Oakes et al., Sensitization of BCL-2 expressing breast tumors to chemotherapy by the BH3 mimetic ABT-737. Proc. Natl. Acad. Sci., vol. 109(8), 2766-2771 (Year: 2012).*
Heeba et al., Induction of heme oxygenase-1 with hemin alleviates cisplatin-induced reproductive toxicity in male rats and enhances it cytotoxicity in prostate cancer cell line. Toxicology Letters, vol. 264, pp. 38-50 (Year: 2016).*
Gui, et al, "Environment Dictates Dependence on Mitochondrial Complex 1 for NAD+ and Aspartate Production and Determines Cancer Cell Sensitivity to Metformin," Cell Metab, 24; 716-727, 2016.
Lee, et al., "Network of Mutually Repressive Metastasis Regulators Can Promote Cell Hetergeneity and Metastatic Transitions," Proc Natl Acad Sci USA, 111; E364-373, 2014.
Tsilidis, et al., Metformin Does Not Affect Cancer Risk: A Cohort Study in the U.K. Clinical Practice Research Datalink Analyzed Like an Intention-to-Treat Trial, Diabetes Care, 37; 2522-2532, 2014.
Wheaton, et al., "Metformin Inhibits Mitochondrial Complex I of Cancer Cells to Reduce Tumorigenesis," eLife 3; e02242, 2014.

* cited by examiner

*Primary Examiner* — Barbara P Badio
(74) *Attorney, Agent, or Firm* — Norton Rose Fulbright US LLP

(57) ABSTRACT

The disclosure relates to improved therapeutic methods for treating cancer patients. The methods include a method for treating cancer in a subject comprising administering an effective amount of a BACH1 inhibitor and an ETC inhibitor to the subject. Further aspects of the disclosure relate to a method for treating cancer in a subject comprising: administering a first therapeutic regimen comprising an ETC inhibitor to the subject after a biological sample from the subject was determined to have a decreased or substantially the same level of expression of BACH1 relative to a control sample or to a cut-off value; wherein the first therapeutic regimen excludes a BACH1 inhibitor; or administering a second therapeutic regimen comprising a BACH1 inhibitor and an ETC inhibitor to the subject after a biological sample from the subject was determined to have an increased level of expression of BACH1 relative to a control sample or a cut-off value.

9 Claims, 33 Drawing Sheets
Specification includes a Sequence Listing.

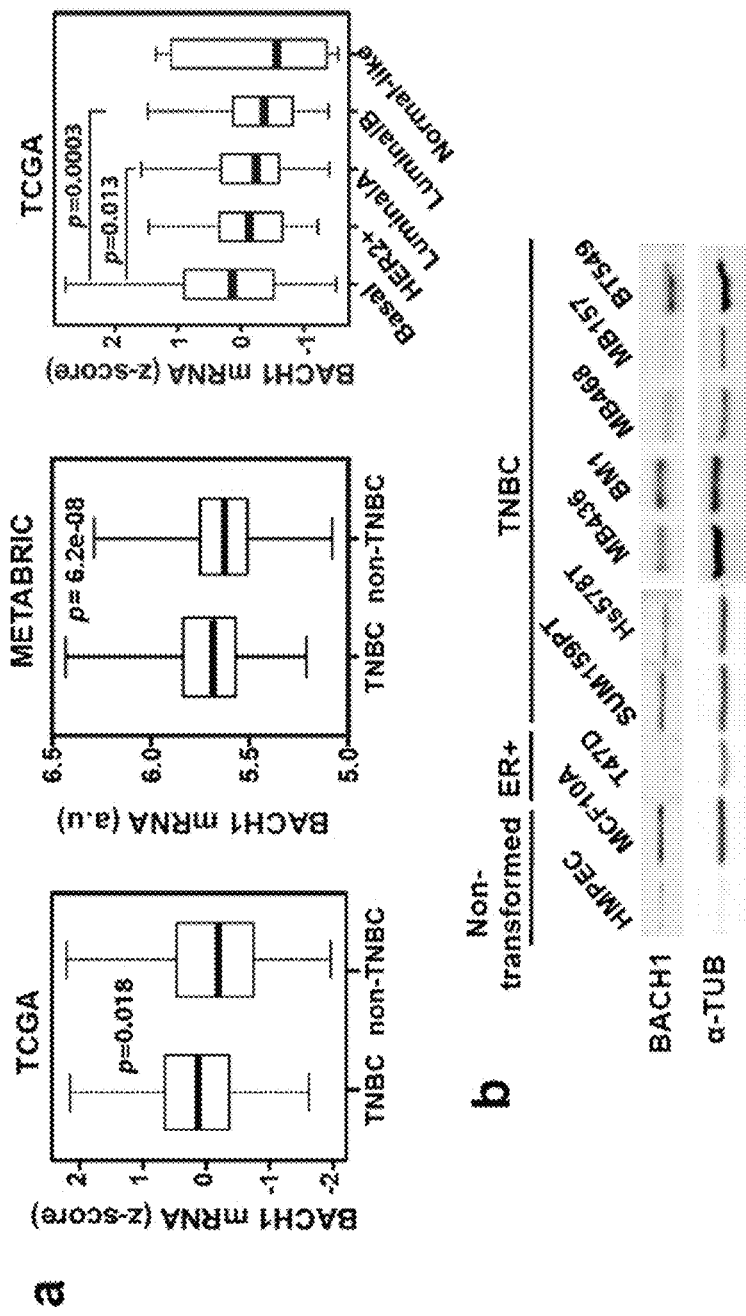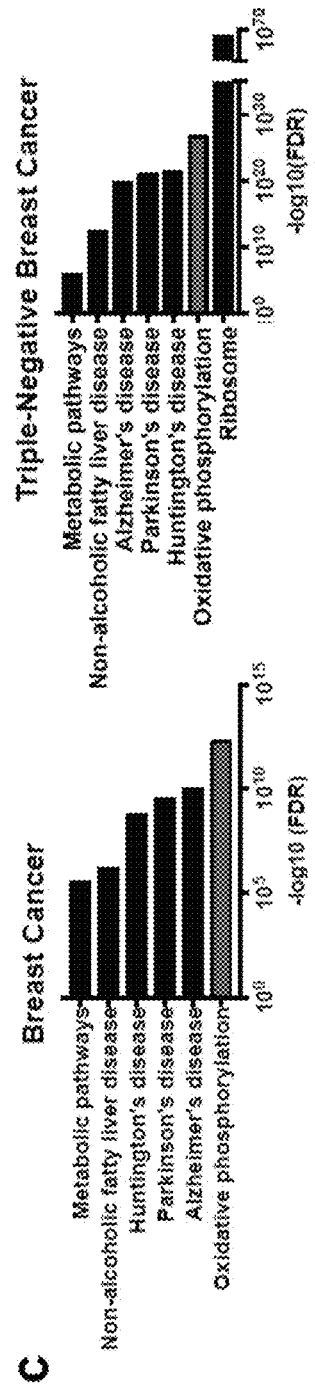
FIGs. 1A-C

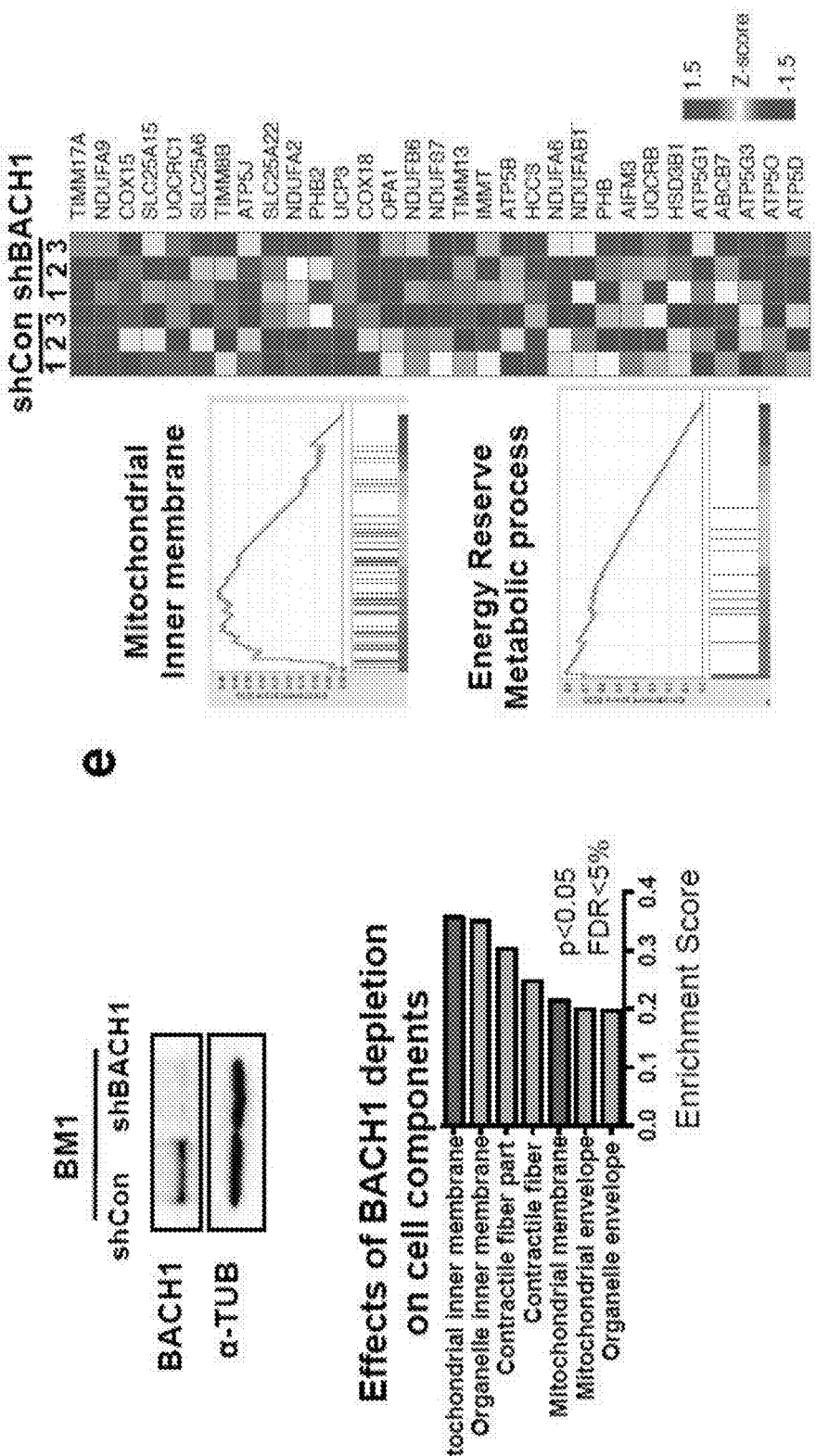
FIGs. 1D-E

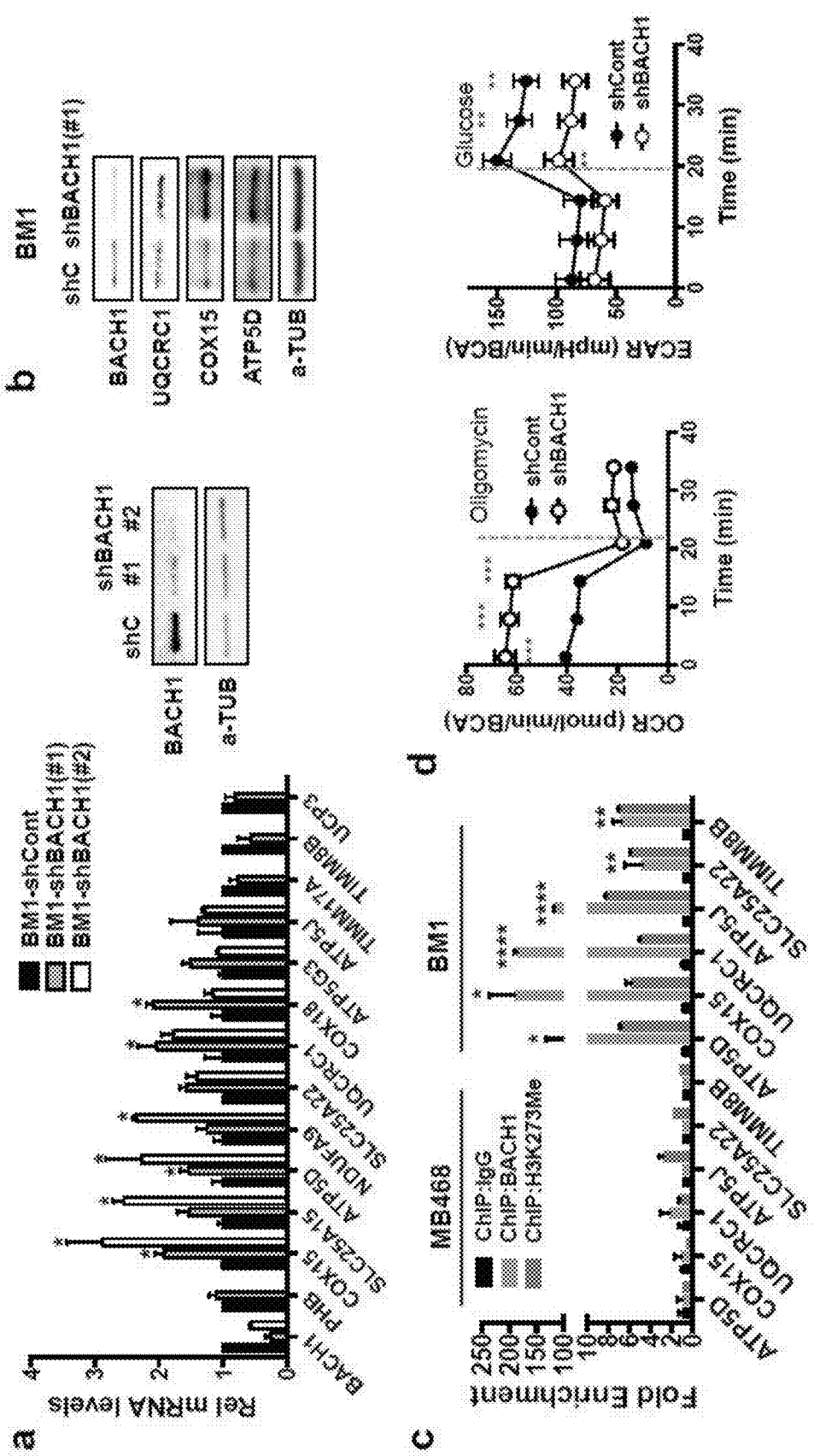
FIGs. 2A-D

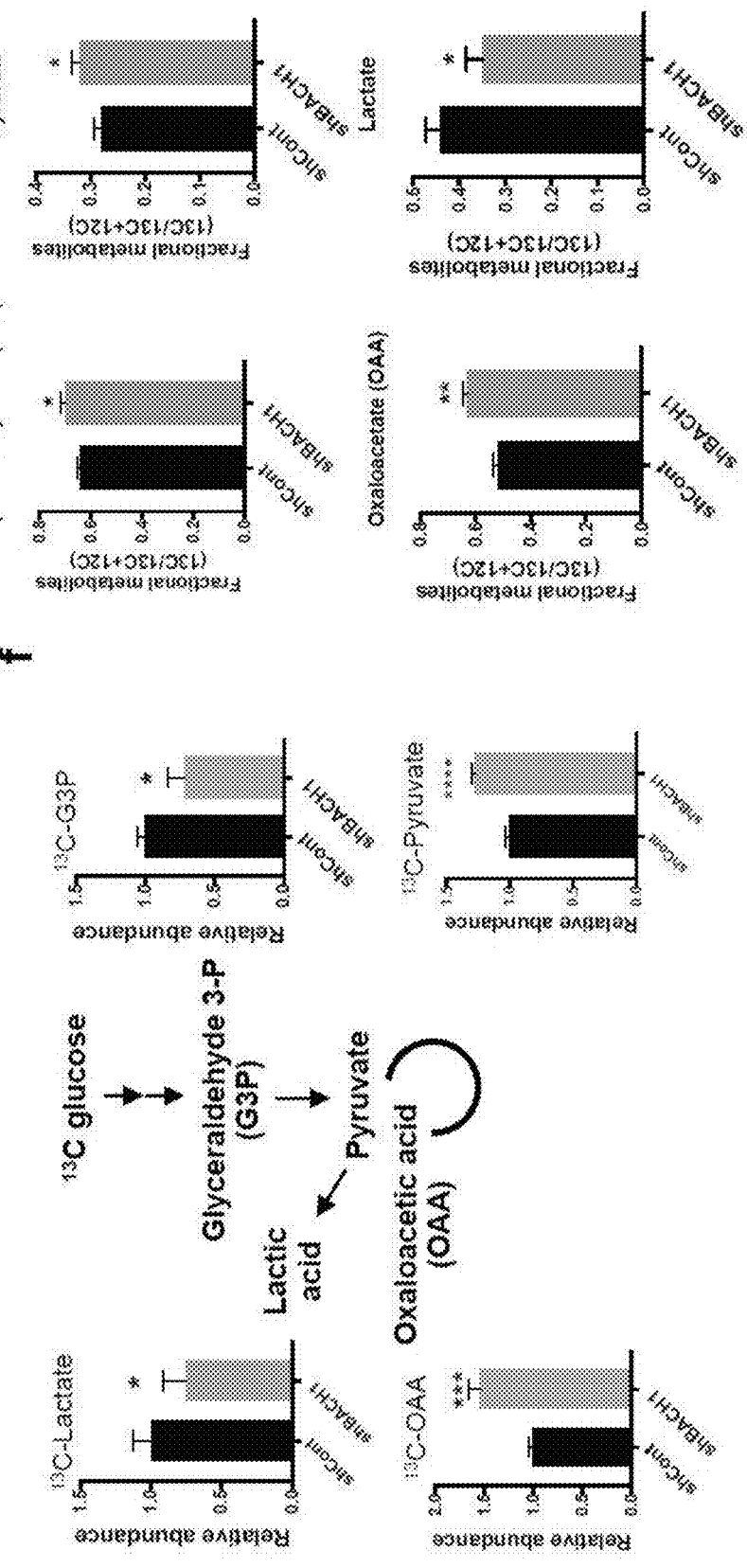
FIGs. 2E-F

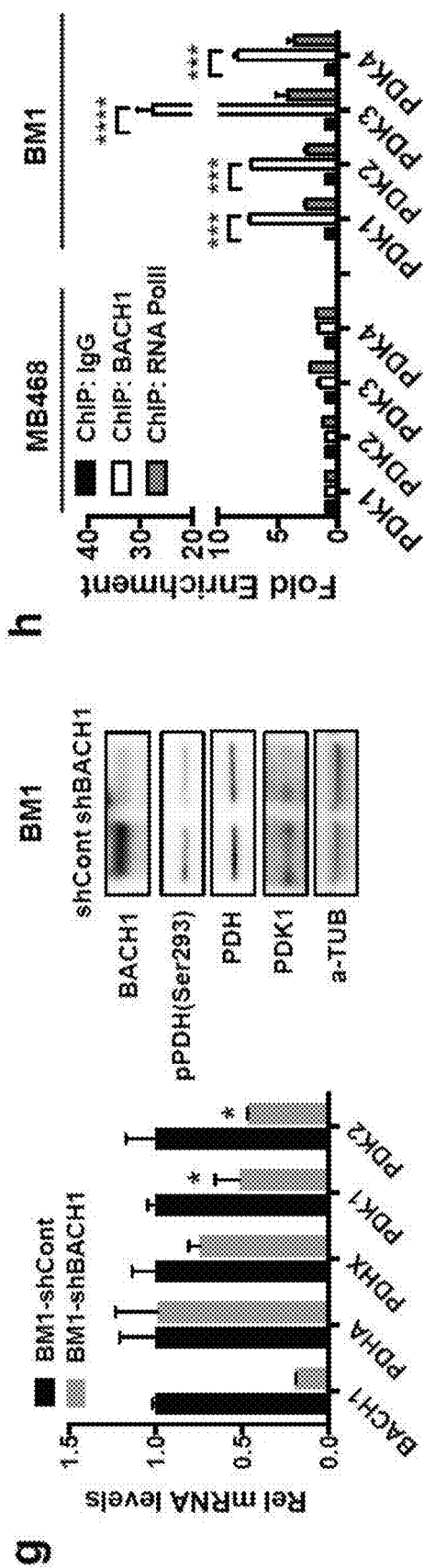
FIGs. 2G-H

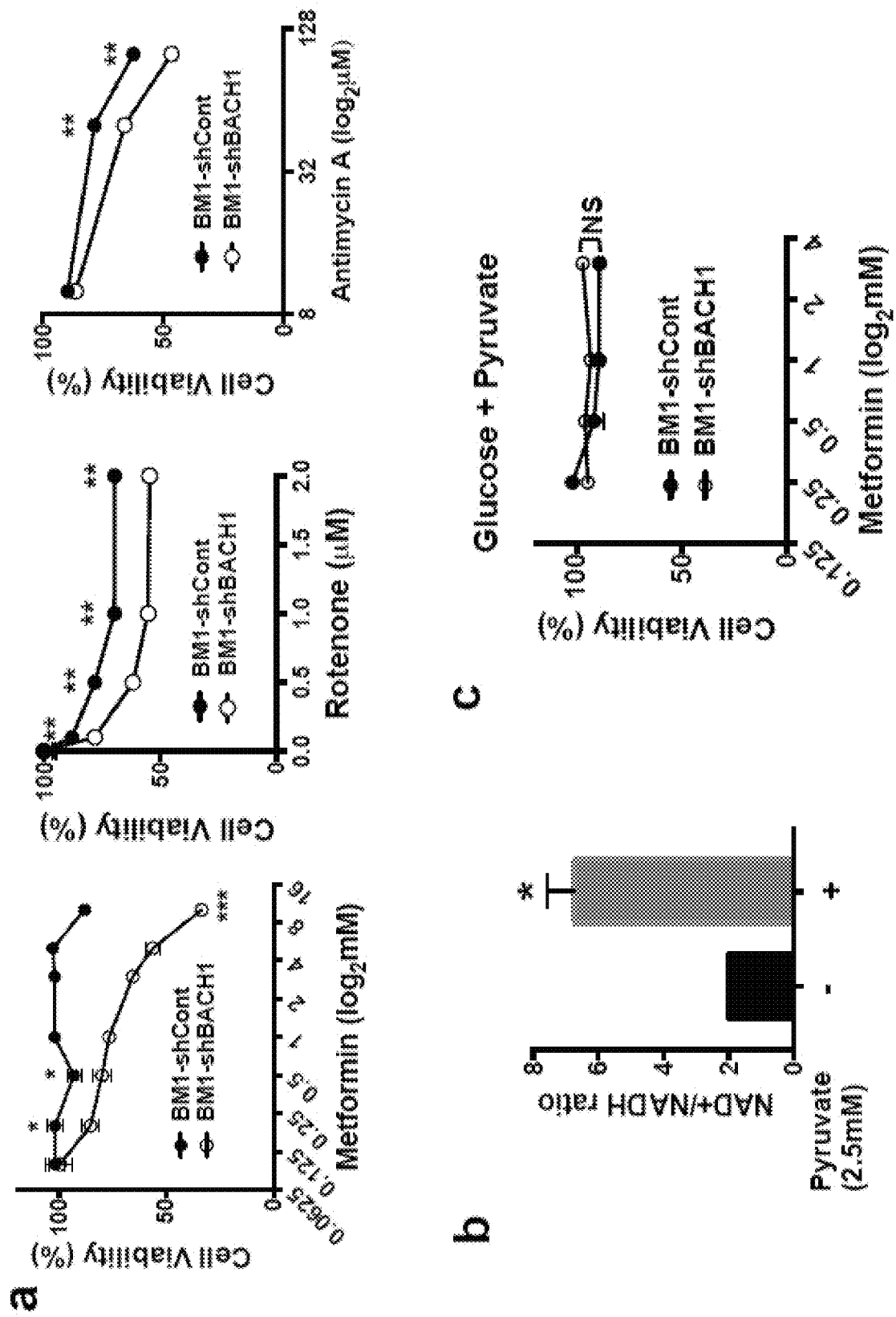
FIGs. 3A-C

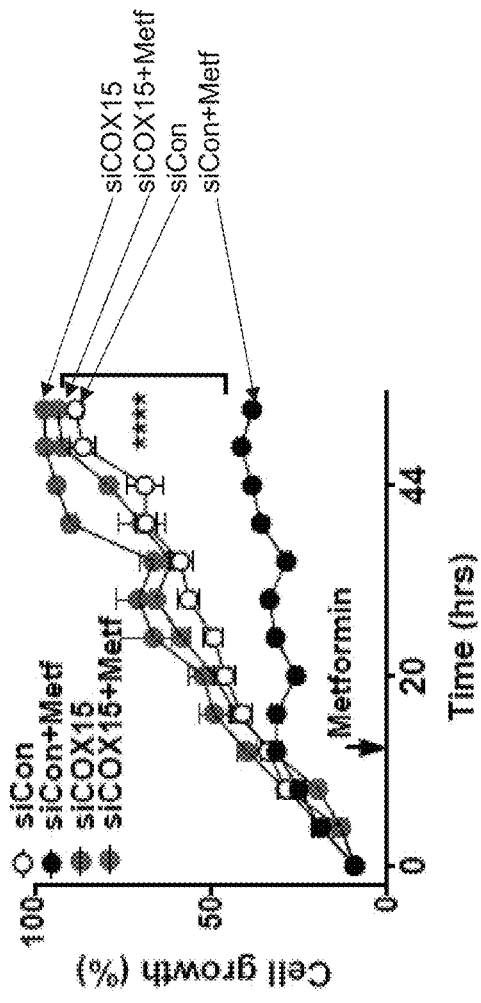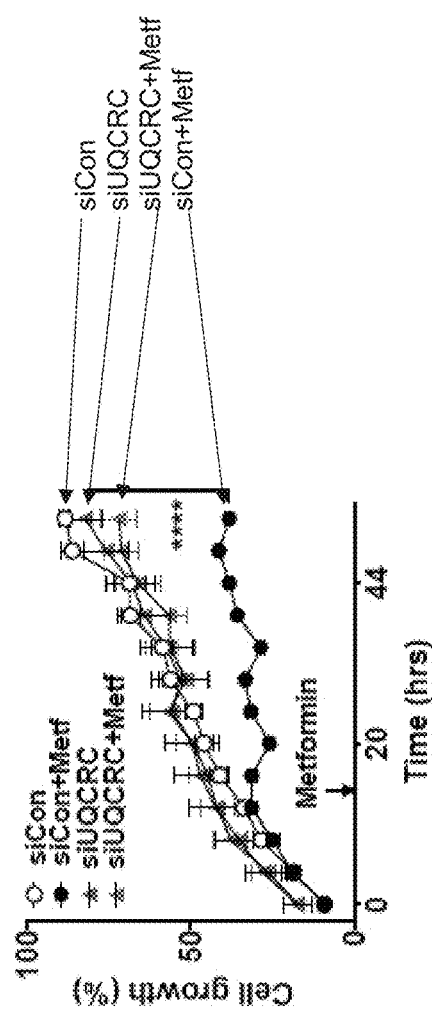
FIG. 3D

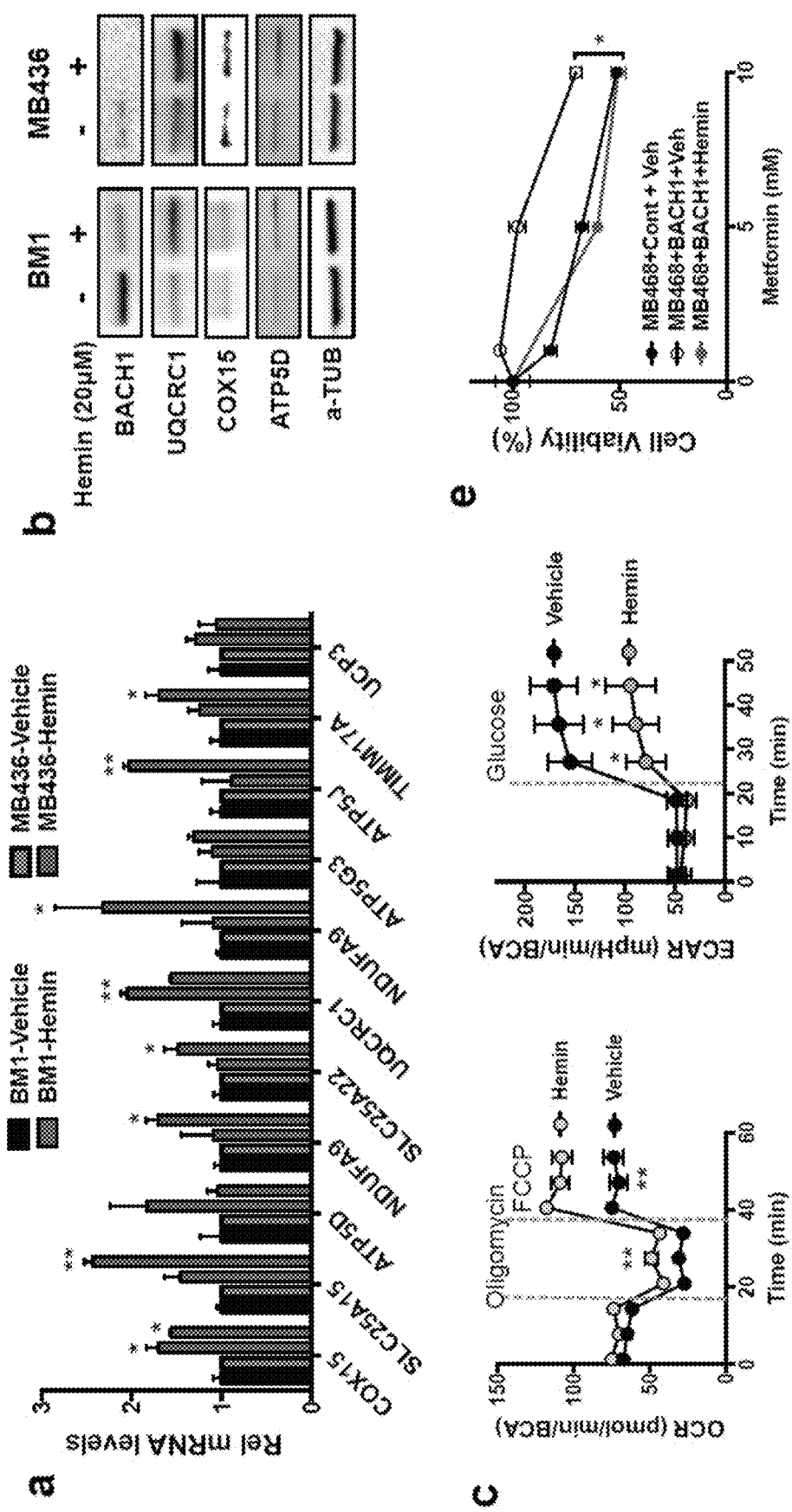
FIGs. 4A-C and 4E

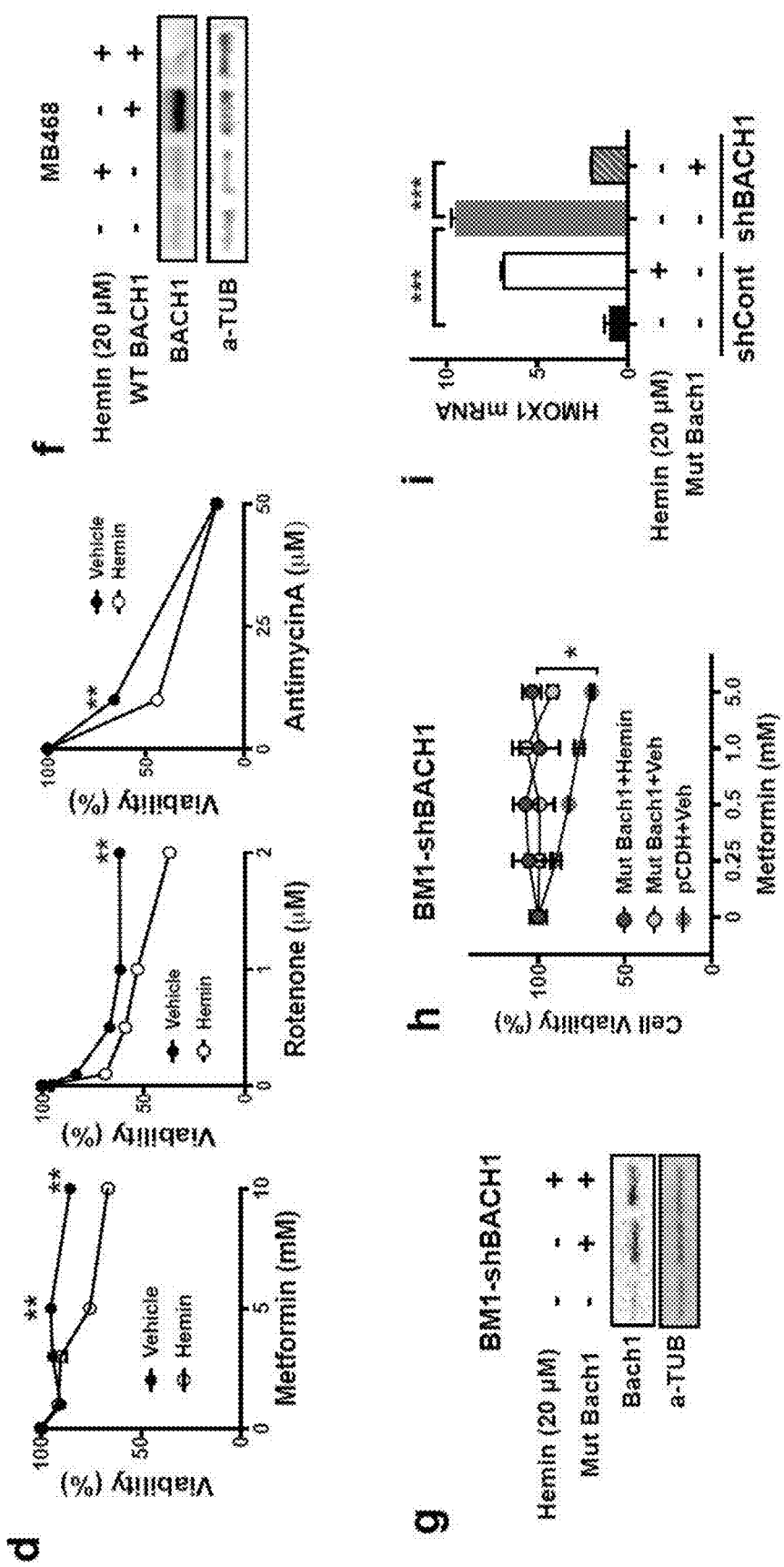
FIGs. 4D and 4F-I

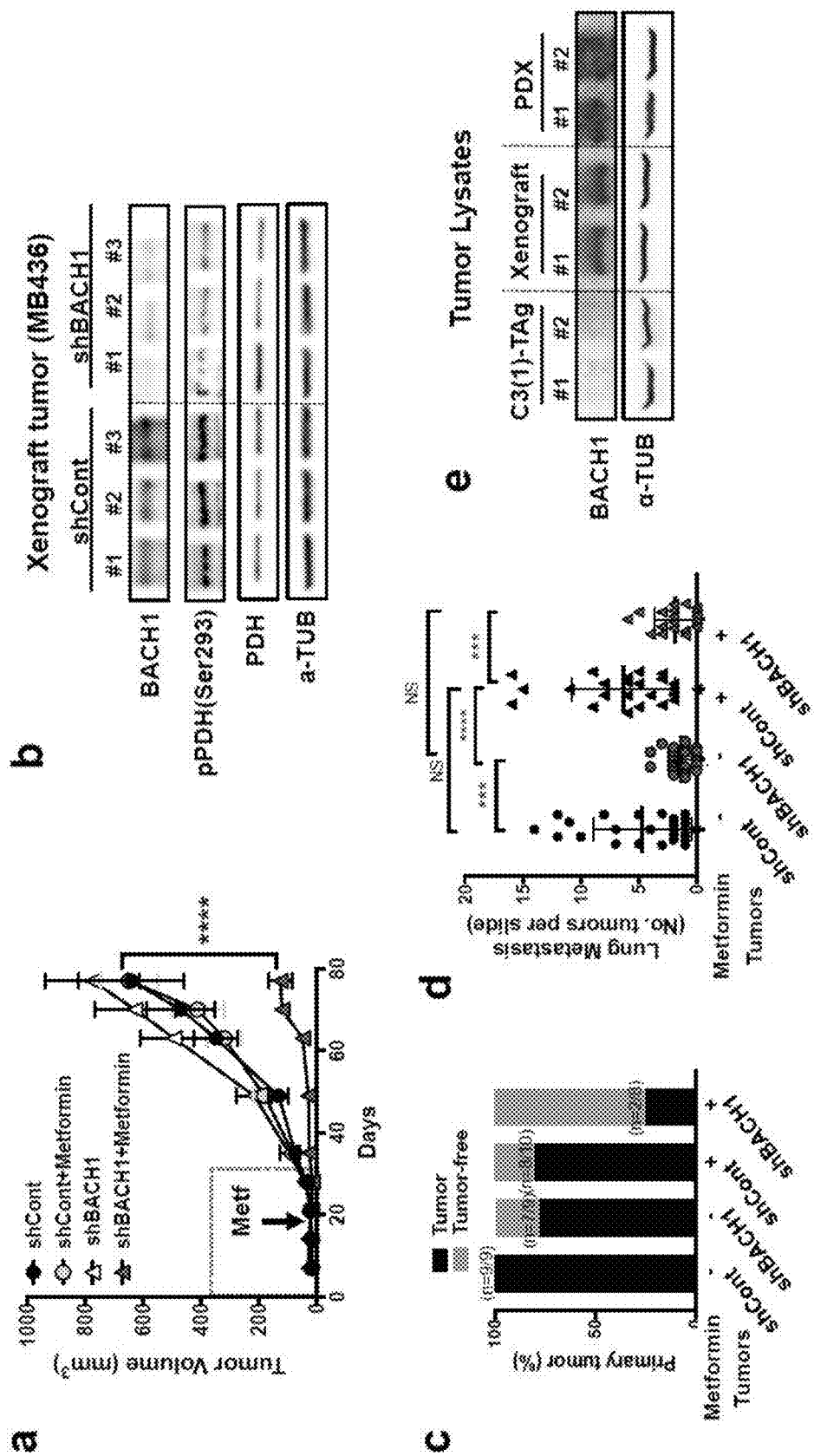
FIGs. 5A-E

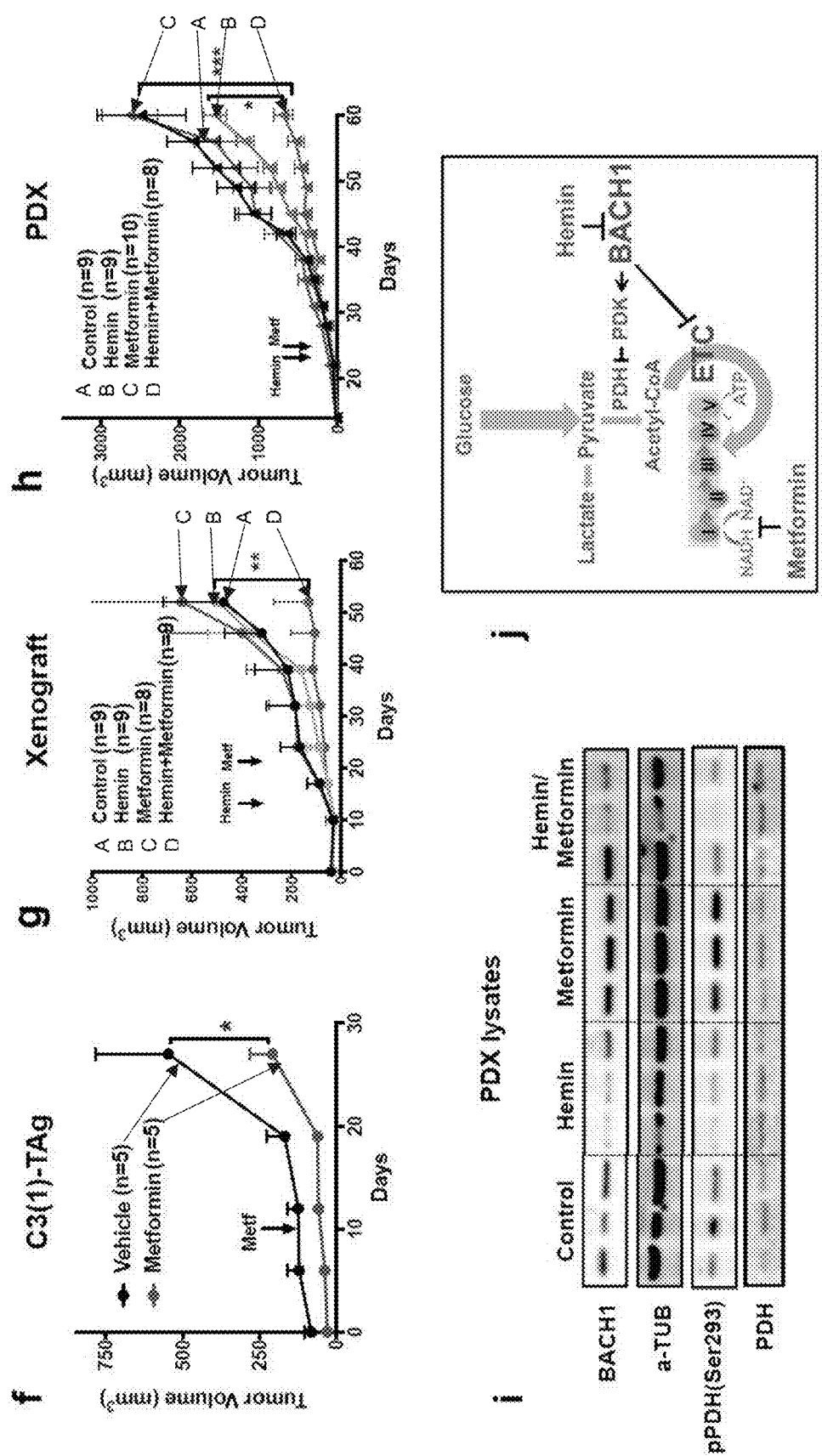
FIGs. 5F-J

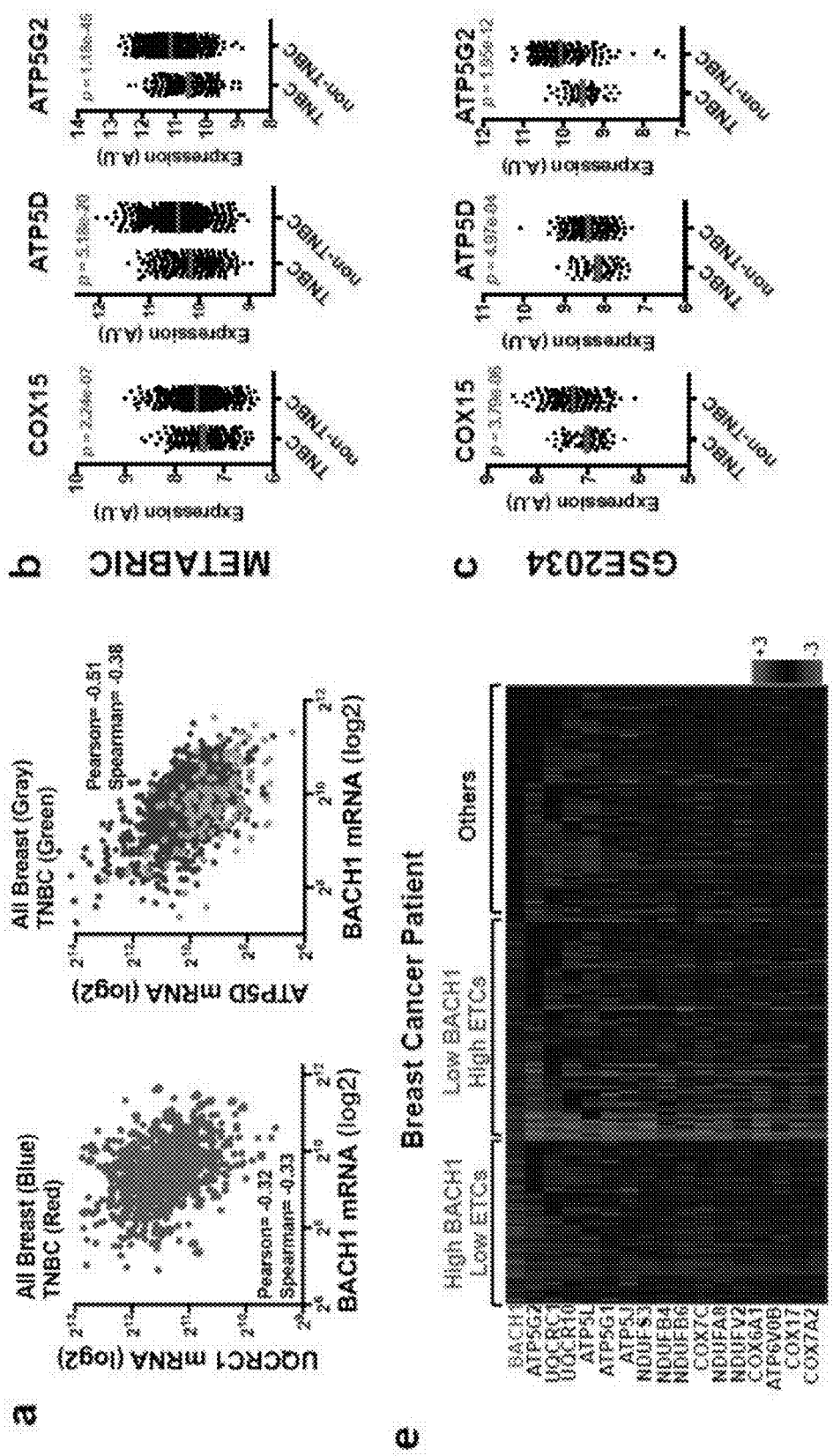
FIGs. 6A-C and 6E

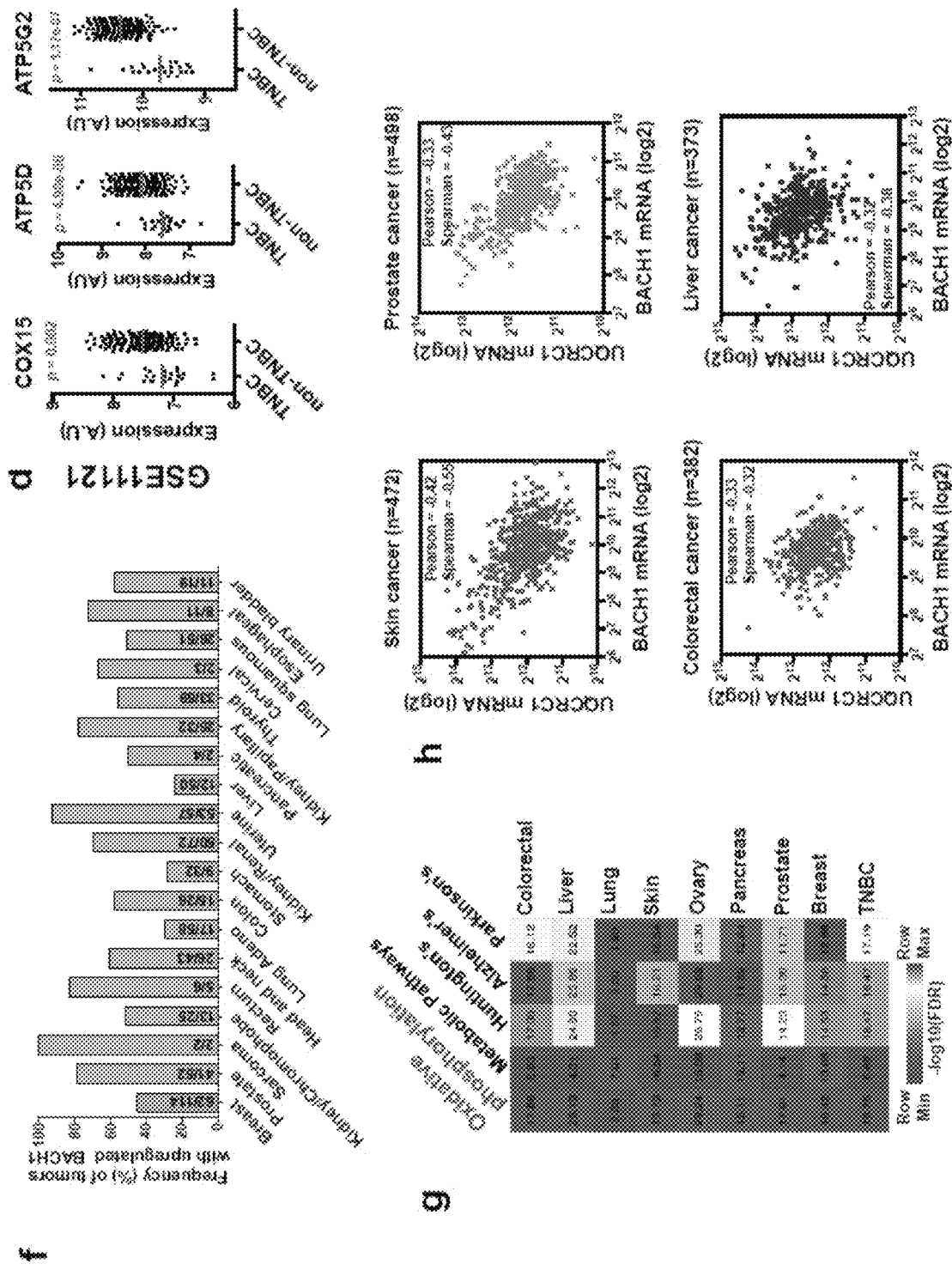
FIGs. 6D and 6F-H

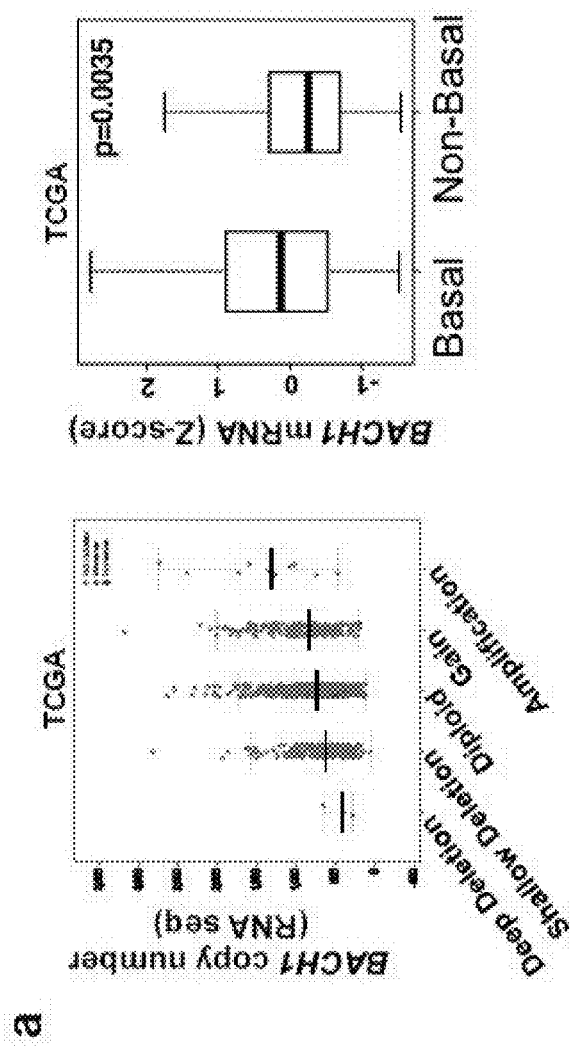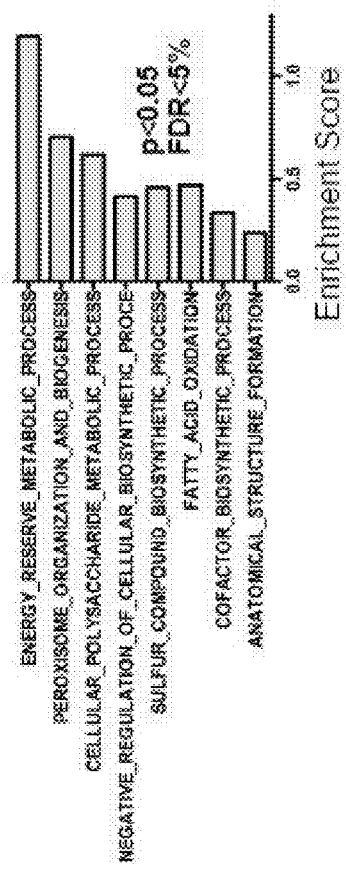
FIGs. 7A-B

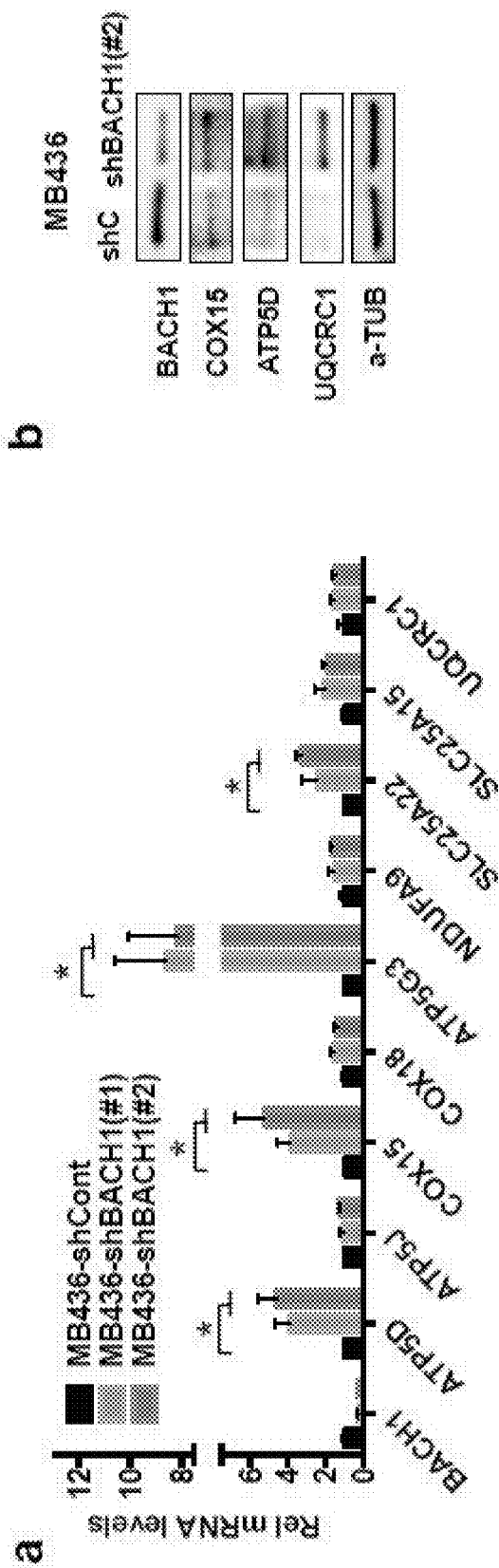
FIGs. 8A-B

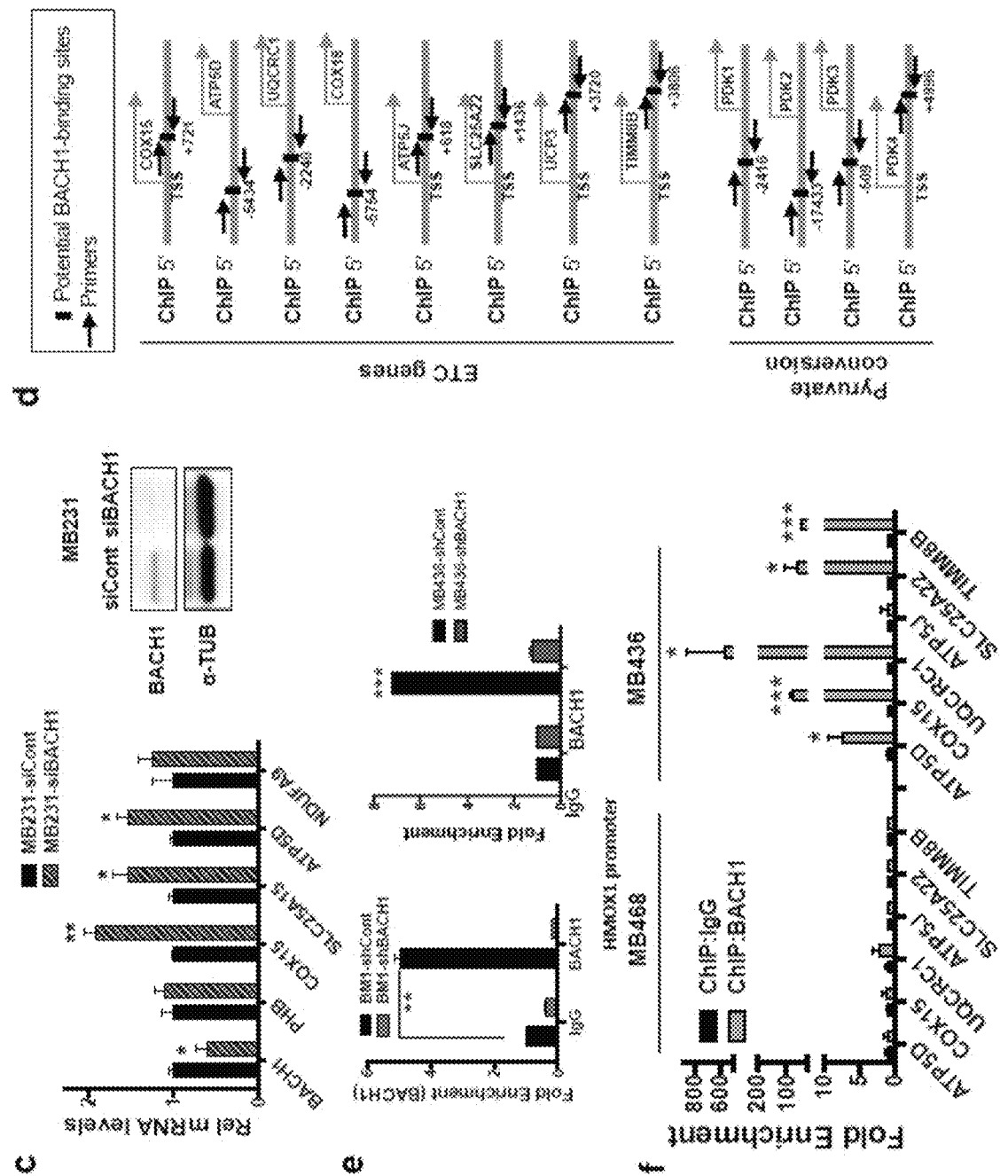
FIGs. 8C-F

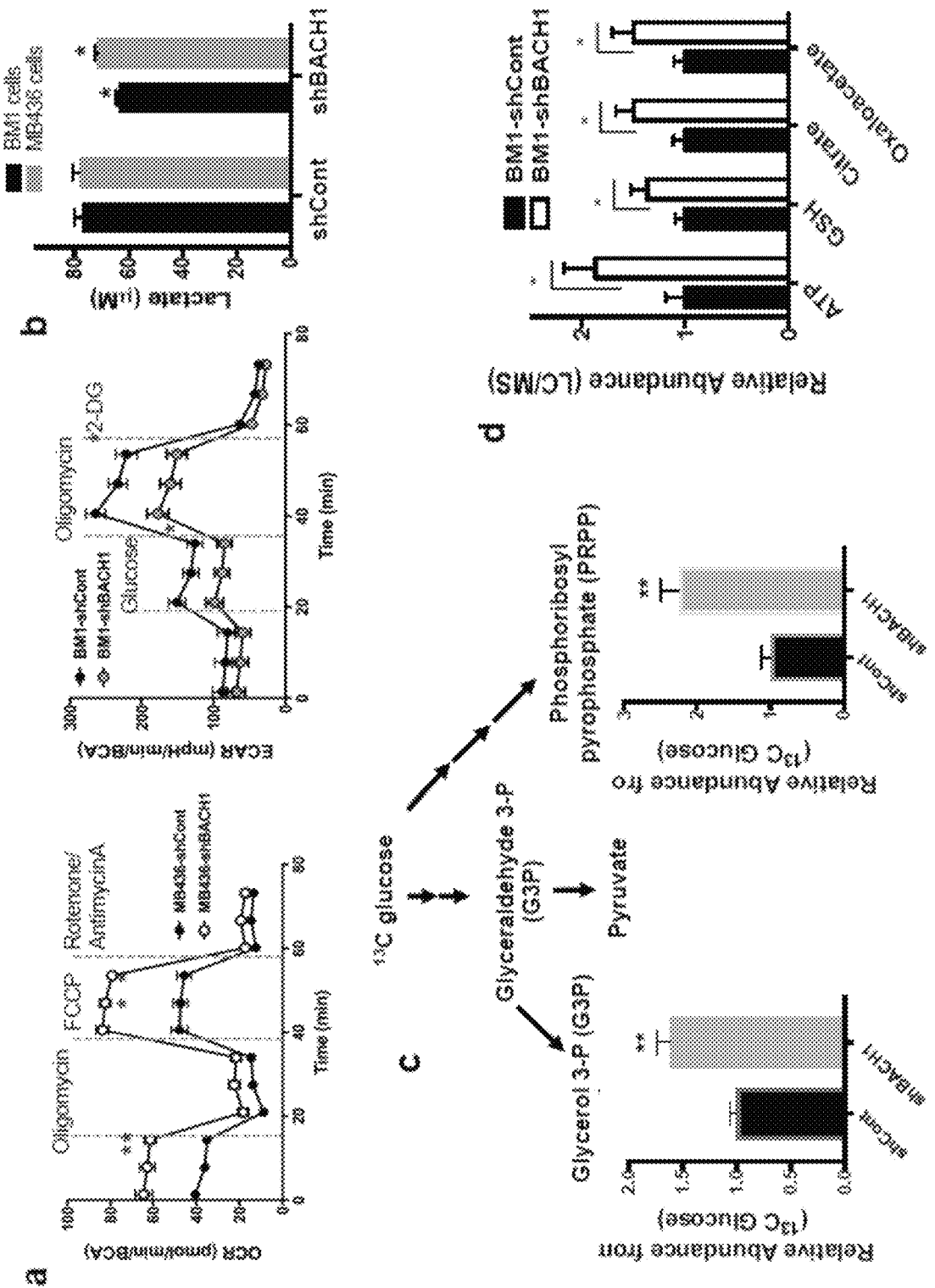
FIGs. 9A-D

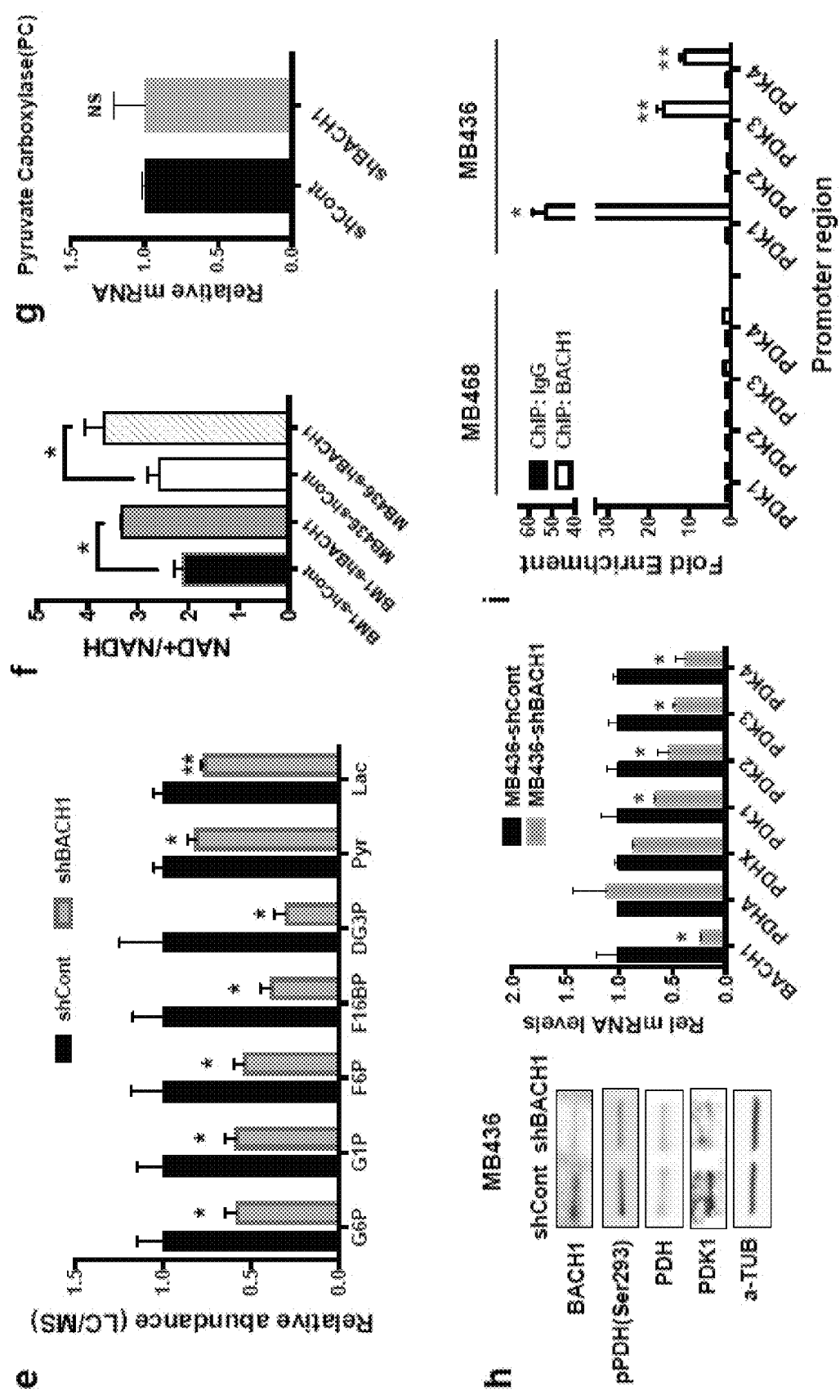
FIGs. 9E-I

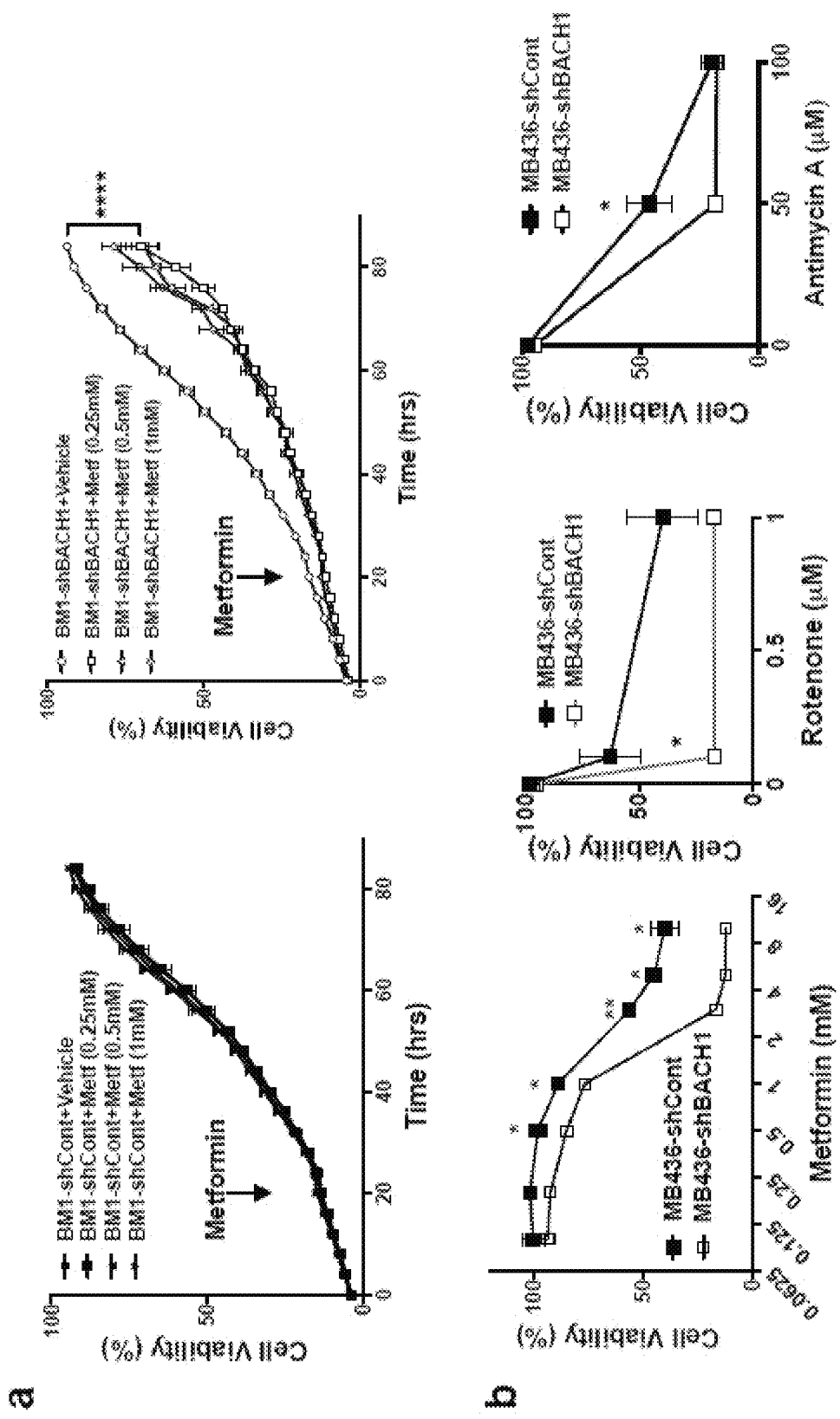
FIGs. 10A-B

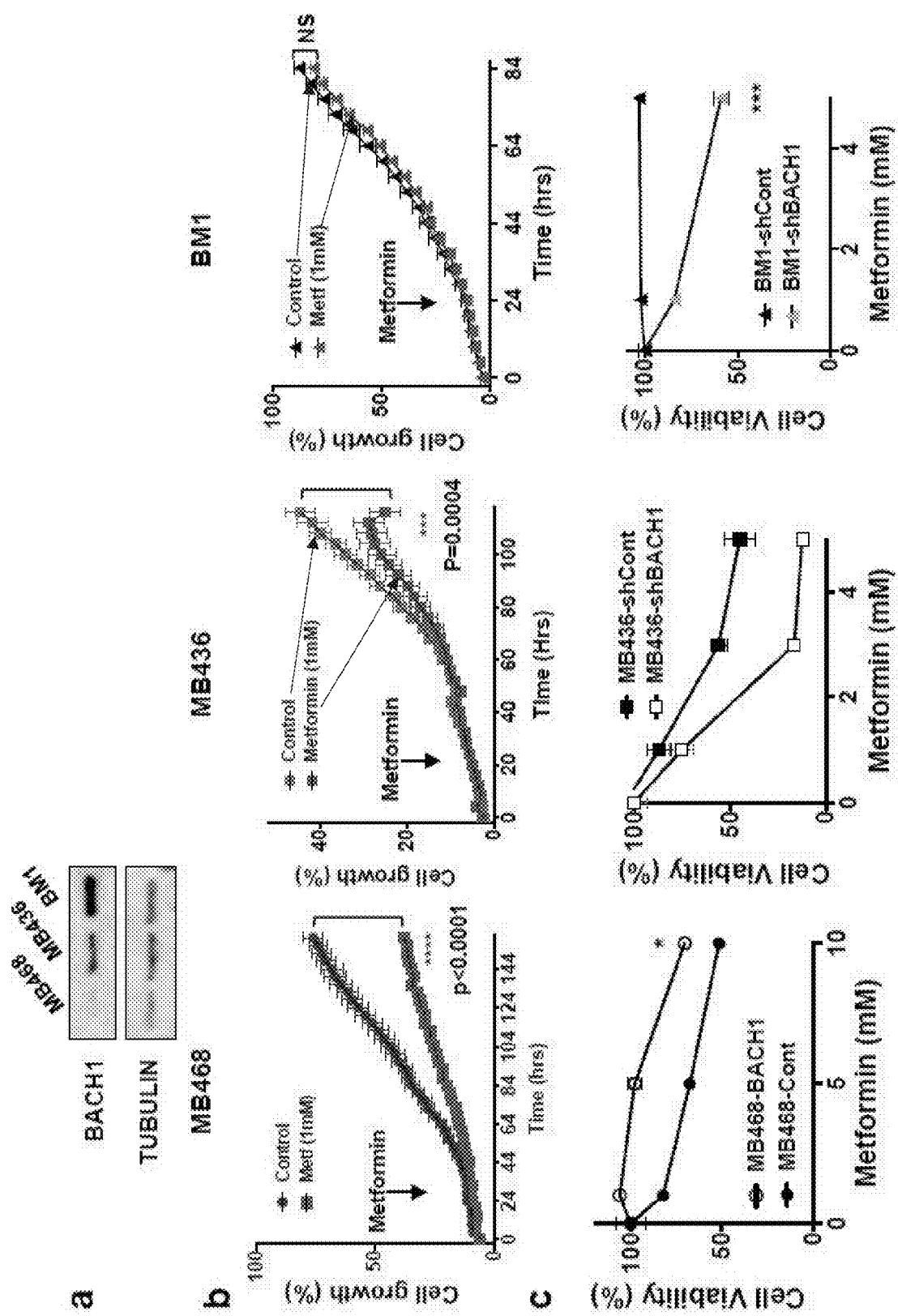
FIGs. 11A-C

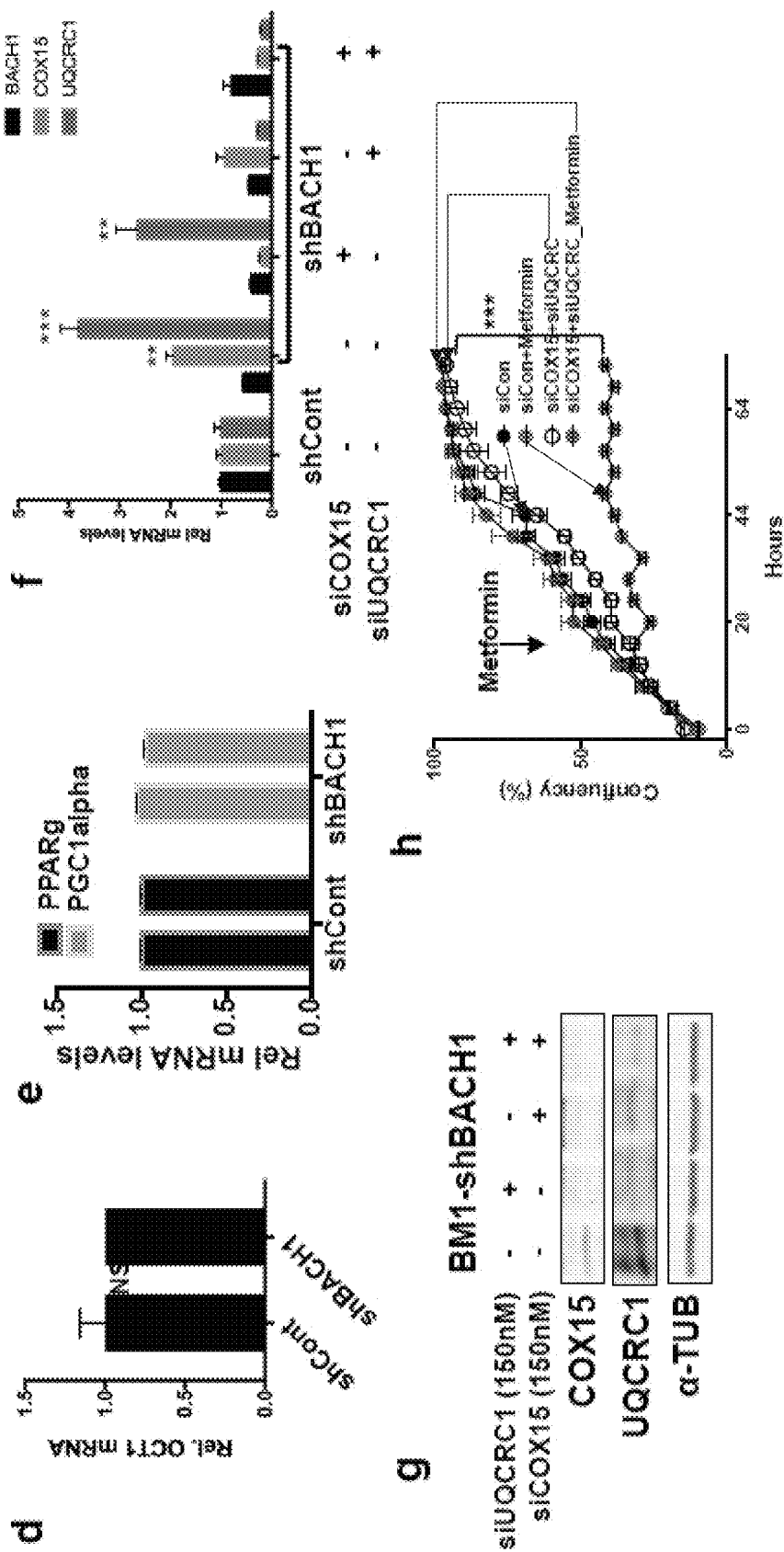
FIGs. 11D-H

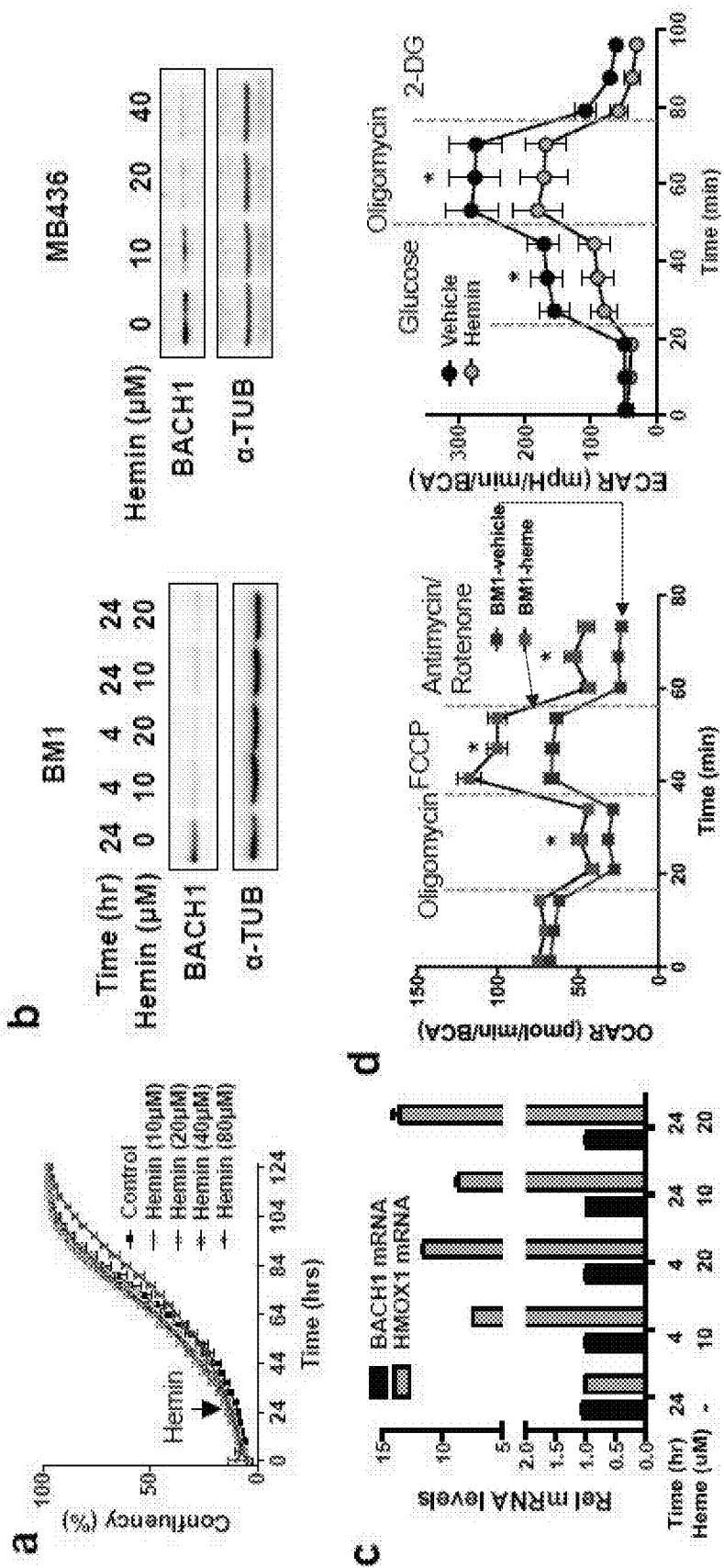
FIGs. 12A-D

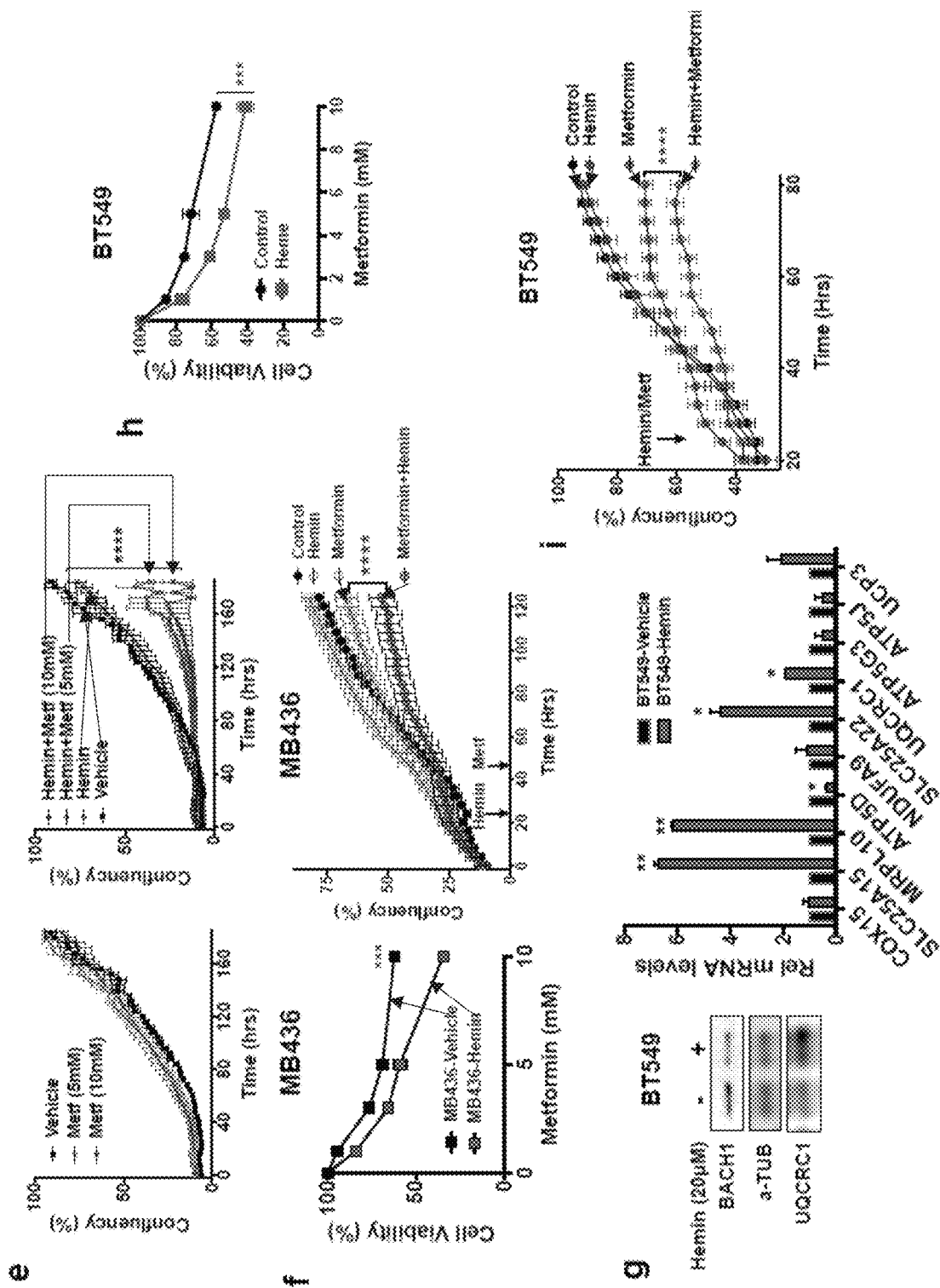
FIGs. 12E-I

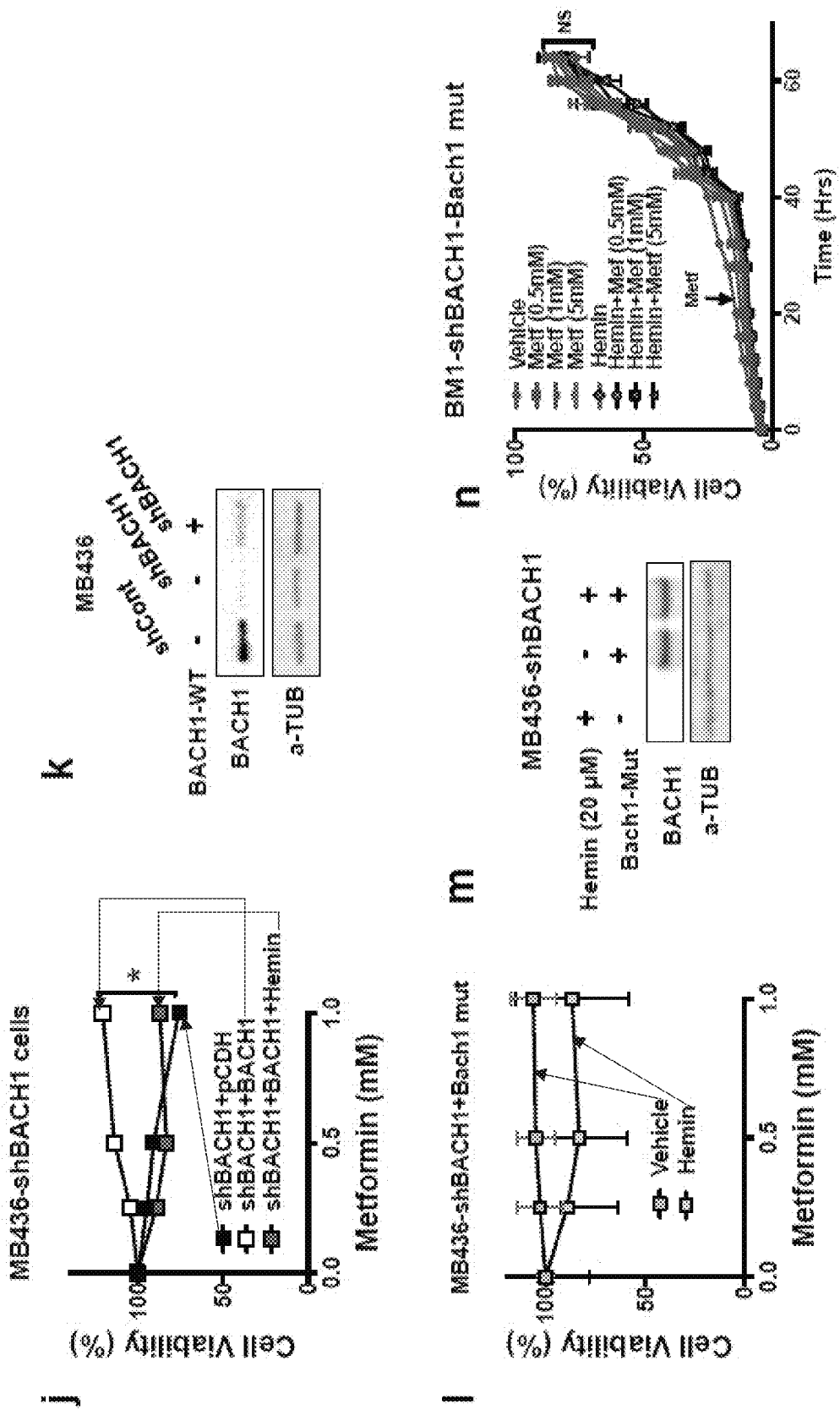
FIGs. 12J-N

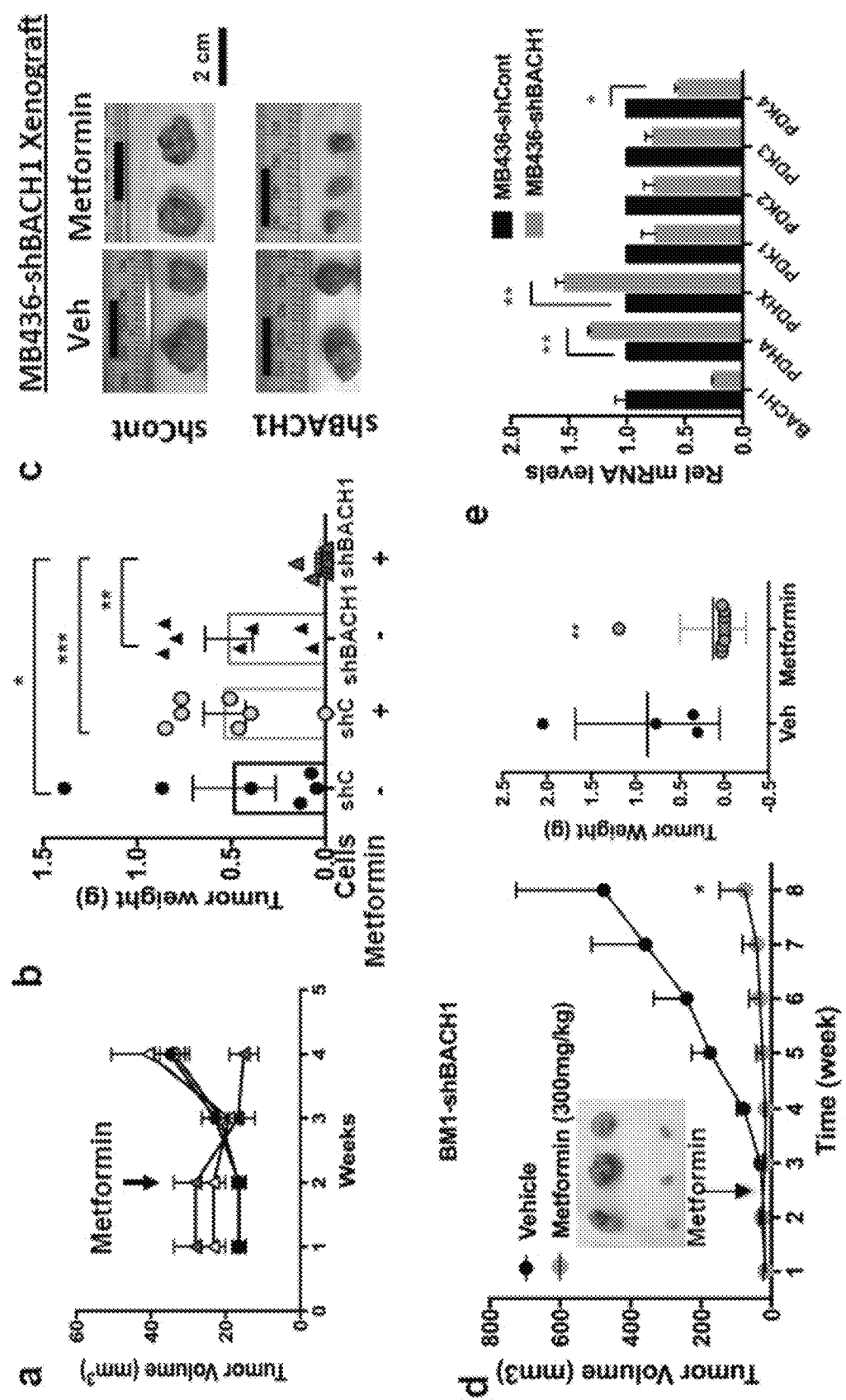
FIGs. 13A-E

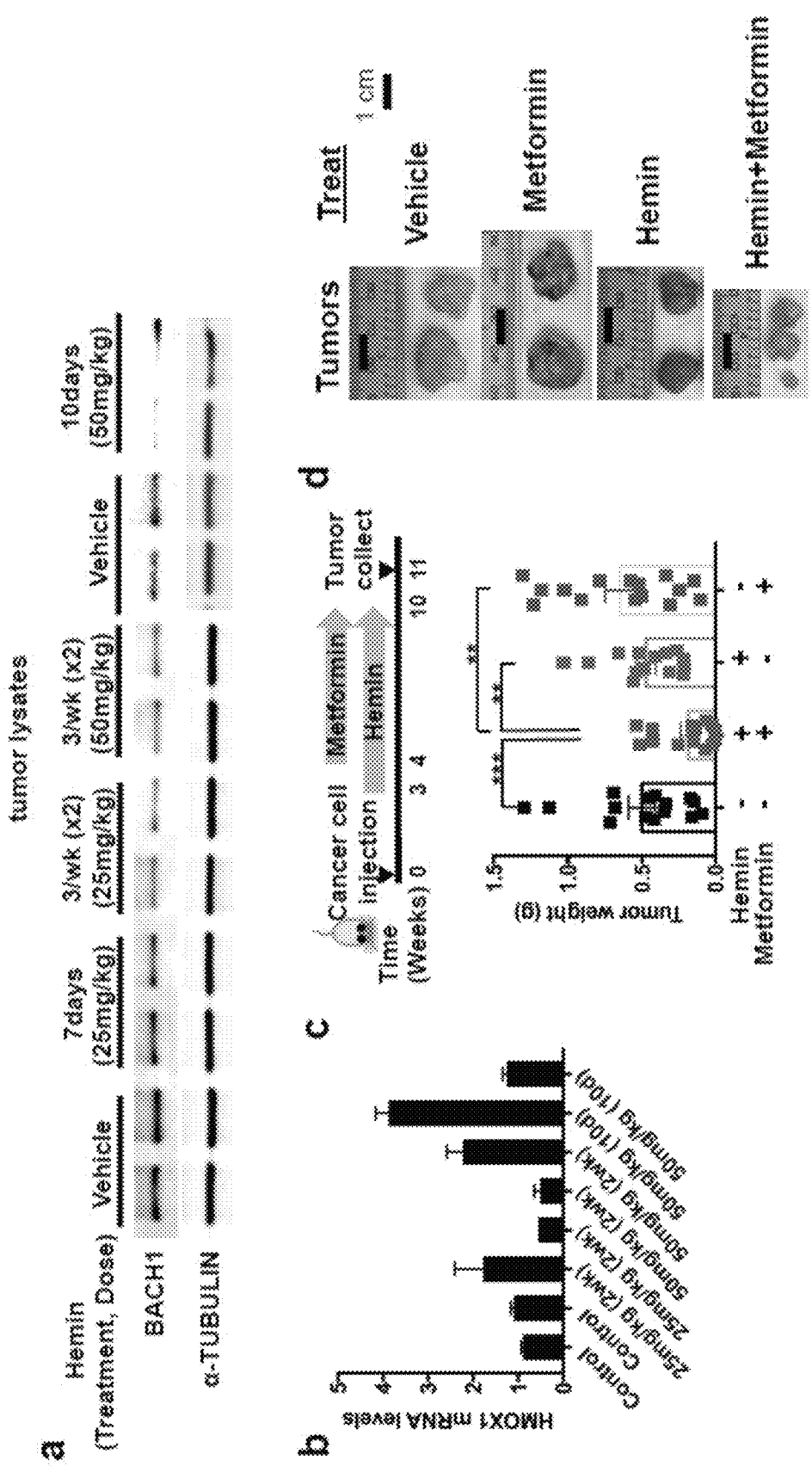
FIGs. 14A-D

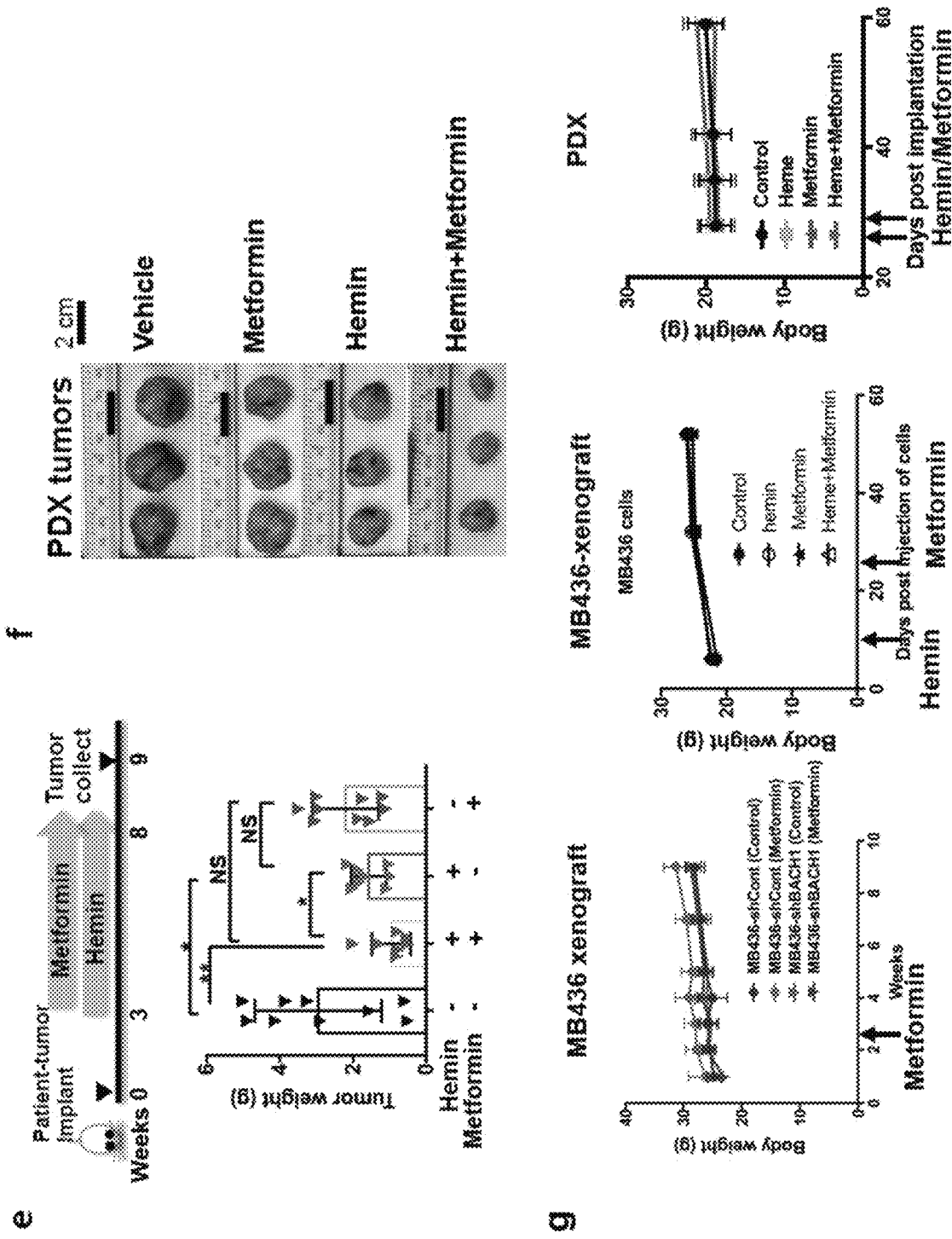
FIGs. 14E-G

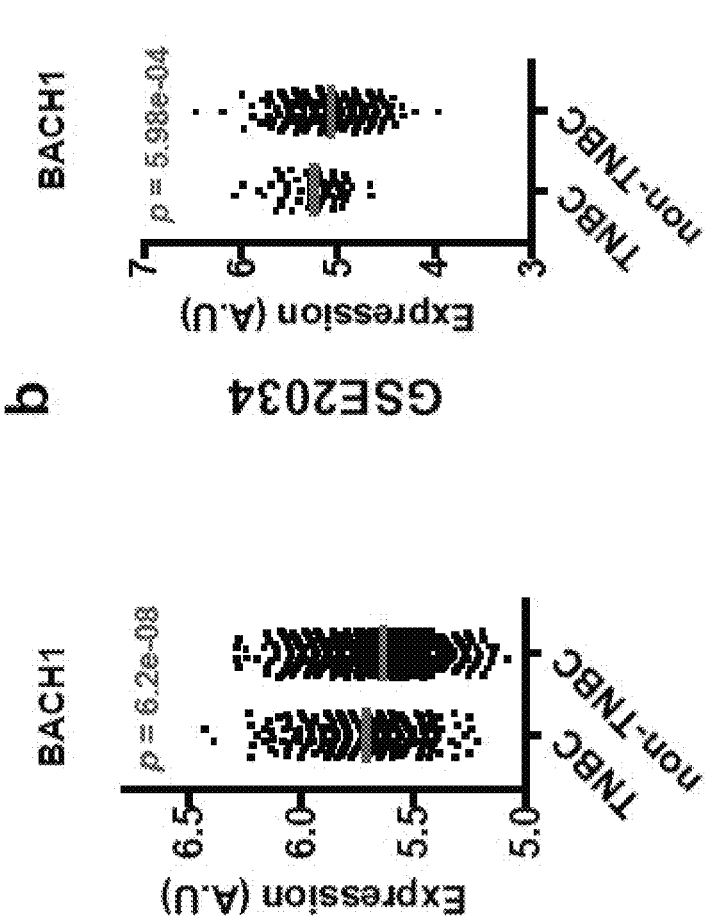
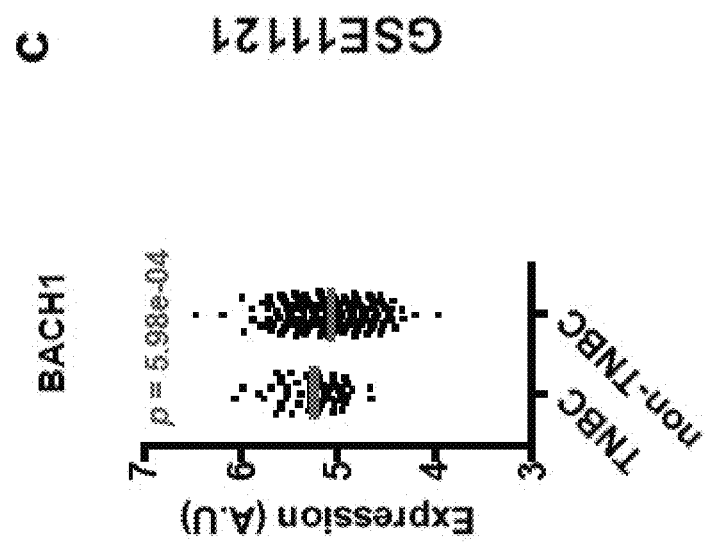
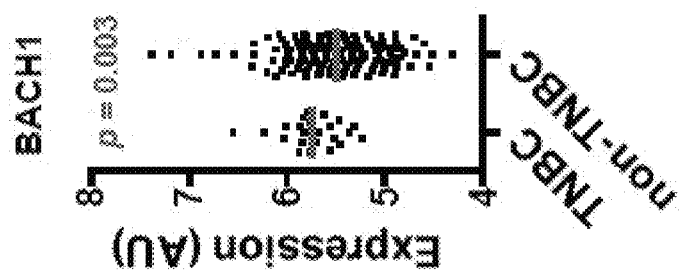
FIGs. 15A-C

SEQUENCE LISTING

```
<160> NUMBER OF SEQ ID NOS: 106

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaauccugc uuucaguuu                                                    19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaacugaaag caggauucc                                                    19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gucugagugu ccgugguua                                                    19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaaccacgga cacucagac                                                    19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcaguuacuu ccacucaag                                                    19

<210> SEQ ID NO 6
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuugagugga aguaacugc                                                  19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuacacugcu aaacugauu                                                  19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aaucaguuua gcaguguag                                                  19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gauuugcagg ugauguuaa                                                  19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuaacaucac cugcaaauc                                                  19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
auuugaaccu uuaauucag                                                  19

<210> SEQ ID NO 12
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 12
cugaauuaaa gguucaaau                                                       19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guuaaaggau uugaaccuu                                                       19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
aagguucaaa uccuuuaac                                                       19

<210> SEQ ID NO 15
<211> LENGTH: 736
<212> TYPE: PRT
<213> ORGANISM: Homo sapiens

<400> SEQUENCE: 15
```

Met Ser Leu Ser Glu Asn Ser Val Phe Ala Tyr Glu Ser Ser Val His
1               5                   10                  15

Ser Thr Asn Val Leu Leu Ser Leu Asn Asp Gln Arg Lys Lys Asp Val
                20                  25                  30

Leu Cys Asp Val Thr Ile Phe Val Glu Gly Gln Arg Phe Arg Ala His
            35                  40                  45

Arg Ser Val Leu Ala Ala Cys Ser Ser Tyr Phe His Ser Arg Ile Val
        50                  55                  60

Gly Gln Ala Asp Gly Glu Leu Asn Ile Thr Leu Pro Glu Glu Val Thr
65                  70                  75                  80

Val Lys Gly Phe Glu Pro Leu Ile Gln Phe Ala Tyr Thr Ala Lys Leu
                85                  90                  95

Ile Leu Ser Lys Glu Asn Val Asp Glu Val Cys Lys Cys Val Glu Phe
            100                 105                 110

Leu Ser Val His Asn Ile Glu Glu Ser Cys Phe Gln Phe Leu Lys Phe
        115                 120                 125

Lys Phe Leu Asp Ser Thr Ala Asp Gln Gln Glu Cys Pro Arg Lys Lys
    130                 135                 140

Cys Phe Ser Ser His Cys Gln Lys Thr Asp Leu Lys Leu Ser Leu Leu
145                 150                 155                 160

Asp Gln Arg Asp Leu Glu Thr Asp Glu Val Glu Glu Phe Leu Glu Asn
                165                 170                 175

Lys Asn Val Gln Thr Pro Gln Cys Lys Leu Arg Arg Tyr Gln Gly Asn
            180                 185                 190

```
Ala Lys Ala Ser Pro Pro Leu Gln Asp Ser Ala Ser Gln Thr Tyr Glu
            195                 200                 205

Ser Met Cys Leu Glu Lys Asp Ala Ala Leu Ala Leu Pro Ser Leu Cys
    210                 215                 220

Pro Lys Tyr Arg Lys Phe Gln Lys Ala Phe Gly Thr Asp Arg Val Arg
225                 230                 235                 240

Thr Gly Glu Ser Ser Val Lys Asp Ile His Ala Ser Val Gln Pro Asn
                245                 250                 255

Glu Arg Ser Glu Asn Glu Cys Leu Gly Val Pro Glu Cys Arg Asp
                260                 265                 270

Leu Gln Val Met Leu Lys Cys Asp Glu Ser Lys Leu Ala Met Glu Pro
            275                 280                 285

Glu Glu Thr Lys Lys Asp Pro Ala Ser Gln Cys Pro Thr Glu Lys Ser
290                 295                 300

Glu Val Thr Pro Phe Pro His Asn Ser Ser Ile Asp Pro His Gly Leu
305                 310                 315                 320

Tyr Ser Leu Ser Leu Leu His Thr Tyr Asp Gln Tyr Gly Asp Leu Asn
                325                 330                 335

Phe Ala Gly Met Gln Asn Thr Thr Val Leu Thr Glu Lys Pro Leu Ser
            340                 345                 350

Gly Thr Asp Val Gln Glu Lys Thr Phe Gly Glu Ser Gln Asp Leu Pro
        355                 360                 365

Leu Lys Ser Asp Leu Gly Thr Arg Glu Asp Ser Ser Val Ala Ser Ser
    370                 375                 380

Asp Arg Ser Ser Val Glu Arg Glu Val Ala Glu His Leu Ala Lys Gly
385                 390                 395                 400

Phe Trp Ser Asp Ile Cys Ser Thr Asp Thr Pro Cys Gln Met Gln Leu
                405                 410                 415

Ser Pro Ala Val Ala Lys Asp Gly Ser Glu Gln Ile Ser Gln Lys Arg
            420                 425                 430

Ser Glu Cys Pro Trp Leu Gly Ile Arg Ile Ser Glu Ser Pro Glu Pro
        435                 440                 445

Gly Gln Arg Thr Phe Thr Thr Leu Ser Ser Val Asn Cys Pro Phe Ile
    450                 455                 460

Ser Thr Leu Ser Thr Glu Gly Cys Ser Ser Asn Leu Glu Ile Gly Asn
465                 470                 475                 480

Asp Asp Tyr Val Ser Glu Pro Gln Gln Glu Pro Cys Pro Tyr Ala Cys
                485                 490                 495

Val Ile Ser Leu Gly Asp Asp Ser Glu Thr Asp Thr Glu Gly Asp Ser
            500                 505                 510

Glu Ser Cys Ser Ala Arg Glu Gln Glu Cys Glu Val Lys Leu Pro Phe
        515                 520                 525

Asn Ala Gln Arg Ile Ile Ser Leu Ser Arg Asn Asp Phe Gln Ser Leu
    530                 535                 540

Leu Lys Met His Lys Leu Thr Pro Glu Gln Leu Asp Cys Ile His Asp
545                 550                 555                 560

Ile Arg Arg Arg Ser Lys Asn Arg Ile Ala Ala Gln Arg Cys Arg Lys
                565                 570                 575

Arg Lys Leu Asp Cys Ile Gln Asn Leu Glu Ser Glu Ile Glu Lys Leu
            580                 585                 590

Gln Ser Glu Lys Glu Ser Leu Leu Lys Glu Arg Asp His Ile Leu Ser
        595                 600                 605

Thr Leu Gly Glu Thr Lys Gln Asn Leu Thr Gly Leu Cys Gln Lys Val
```

```
            610                 615                 620
Cys Lys Glu Ala Ala Leu Ser Gln Glu Gln Ile Gln Ile Leu Ala Lys
625                 630                 635                 640

Tyr Ser Ala Ala Asp Cys Pro Leu Ser Phe Leu Ile Ser Glu Lys Asp
                645                 650                 655

Lys Ser Thr Pro Asp Gly Glu Leu Ala Leu Pro Ser Ile Phe Ser Leu
            660                 665                 670

Ser Asp Arg Pro Pro Ala Val Leu Pro Pro Cys Ala Arg Gly Asn Ser
        675                 680                 685

Glu Pro Gly Tyr Ala Arg Gly Gln Ser Gln Met Ser Thr Ala
    690                 695                 700

Thr Ser Glu Gln Ala Gly Pro Ala Glu Gln Cys Arg Gln Ser Gly Gly
705                 710                 715                 720

Ile Ser Asp Phe Cys Gln Gln Met Thr Asp Lys Cys Thr Thr Asp Glu
                725                 730                 735
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caccgaagga gacagtgaat cc                                              22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctgttctgg agtaagcttg tgc                                             23

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttctcctct gtcattcggt ca                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccagatgtc tgtcgcttag at                                              22

<210> SEQ ID NO 20
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 20
ccagagttgc atacagacca at                                              22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccattaaat accgtagagc cct                                             23

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcccacgcag gtgttcttc                                                  19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaccgctg ctcacaaagt                                                 20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagcgcctag agcacagtg                                                  19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccagactct gtcaacctag t                                               21

<210> SEQ ID NO 26
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
gggcagcatt ctgctctcc                                              19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccaactgat ttgcacgaac t                                           21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cacatggccc gctccatac                                              19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtgccgccgt ttttcagatt c                                           21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caccgtcgtg tgatgcactt                                             20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cggctatcat tcggttgtcc t                                           21

<210> SEQ ID NO 32
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 32
gtcacgttct gccattactg c                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtggttgac aacatatcgc c                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccacagaaga tggggcctat g                                              21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tccagacagg tacaagtaca tga                                            23

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttcgcaagg tctacgacca g                                              21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaatagtgg tagtagcctc ctc                                            23

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gtgtgtagac cccctggcta                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgtagccag ccatccagtt                                               20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggtagcatc ccgtaatttt gc                                            22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
attcggcgta cagtctgcat c                                             21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagaggcgct ttcactggac                                               20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
actaaccttg tatgccccat ca                                            22

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttgggaggtt ccgacctgt                                                    19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caaccactcg actgtcactt g                                                 21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cctgaagact tactcccagg t                                                 21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcgatgttgg cgattagtgc                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gccagccaag ctcatcaatg                                                   20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gaggcagtcg gacatgctc                                                    19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
ggtggggcct ttacgatgg                                                19

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gccctggttt taatagctgt ca                                            22

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tcacttcatg gagttatgtt ggg                                           23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agacaatttt cagtgcgaga gtc                                           23

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgttttgctg acctcgttac c                                             21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gacggagtca tagaggccga t                                             21

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```
ggggcacaag tgctattgc                                                19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gttgtccagc aggctaacc                                                19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaggaagcct ggtcagctc                                                19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cagggaagac ccagcttgt                                                19

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aactggagtc ccaaaaggcc                                               20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaagtagagc ggaggtggtg                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62 tgggacagggg atgagtgatt                                              20

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgtctgcttt gttttcattt gc                                            22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
actgttgatg actgaaaagc ca                                            22

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aaaagccacc actgttccca                                               20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gccaggtcga tgggaaaca                                                19

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
catggtcaag gaagccggt                                                19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agcccatacc tctgtagcca                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cccgtgctga acaagagtca                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaagctctgc ctaagaccgc                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccatccagga gcgacagaaa                                              20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gttgggatgg aggttgaatg a                                            21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtgtgtatct ctgtgcctgt g                                            21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aacaagggca gcttggaagt                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75 gtgaggggt gagtcagttc                                                    20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgcacacaag ggaccttcag                                                   20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tcgaccttgg gaggaaatgc                                                   20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acacaaacgt cacagaggca                                                   20

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gagtcggttg ctgcacgta                                                    19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggcttgggtt tcctgtctgt                                                   20

-continued

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agcgggtcac attctcagtg                                                 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgggacaggg atgagtgatt                                                 20

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgtctgcttt gttttcattt gc                                              22

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaggaagcct ggtcagctc                                                  19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cagggaagac ccagcttgt                                                  19

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gttgggatgg aggttgaatg a                                               21

<210> SEQ ID NO 87

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtgtgtatct ctgtgcctgt g                                              21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
aactggagtc ccaaaaggcc                                                20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaagtagagc ggaggtggtg                                                20

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gccaggtcga tgggaaaca                                                 19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
catggtcaag gaagccggt                                                 19

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aaagctctgc ctaagaccgc                                                20

<210> SEQ ID NO 93
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccatccagga gcgacagaaa                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agcccatacc tctgtagcca                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cccgtgctga acaagagtca                                               20

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
actgttgatg actgaaaagc ca                                            22

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aaaagccacc actgttccca                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aacaagggca gcttggaagt                                               20

<210> SEQ ID NO 99
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 99
gtgagggggt gagtcagttc                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tgcacacaag ggaccttcag                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tcgaccttgg gaggaaatgc                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acacaaacgt cacagaggca                                              20

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gagtcggttg ctgcacgta                                               19

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggcttgggtt tcctgtctgt                                              20

<210> SEQ ID NO 105
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 105
agcgggtcac attctcagtg                                                    20

<210> SEQ ID NO 106
<211> LENGTH: 11
<212> TYPE: DNA
<213> ORGANISM: Unknown
<220> FEATURE:
<223> OTHER INFORMATION: Description of Unknown:
      MAF recognition element

<400> SEQUENCE: 106
tgctgastca y                                                             11
```

METHODS AND COMPOSITIONS FOR TREATING CANCER

This application claims the benefit of priority to U.S. Provisional Patent Application Ser. No. 62/517,626, filed Jun. 9, 2017, hereby incorporated by reference in its entirety.

This invention was made with government support under Grant Number CA184494 awarded by The National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jul. 26, 2018, is named ARCD_P0634US_1001031380_SL.txt and is 30,452 bytes in size.

BACKGROUND

1. Field of the Invention

Embodiments are directed generally to biology and medicine. In certain aspects methods involve treating cancer patients and determining an optimal therapeutic regimen for the cancer patient. In additional embodiments there are therapeutic compositions and the use of such compositions for the treatment of breast cancer.

2. Description of Related Art

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002).

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE DISCLOSURE

The current disclosure fulfills the aforementioned need in the art by providing improved therapeutic methods for treating cancer patients. Accordingly, certain aspects of the disclosure relate to a method for treating cancer in a subject comprising administering an effective amount of a i) BACH1 inhibitor and ii) an ETC inhibitor to the subject. Further aspects relate to a method for treating cancer in a subject comprising administering an effective amount of a i) BACH1 inhibitor and ii) an ETC inhibitor and/or a chemotherapeutic agent to the subject. Yet further aspects relate to a method for treating cancer in a subject comprising administering an effective amount of a i) BACH1 inhibitor and ii) a chemotherapeutic agent to the subject.

Further aspects of the disclosure relate to a method for treating cancer in a subject comprising: administering a first therapeutic regimen comprising an ETC inhibitor to the subject after a biological sample from the subject was determined to have a decreased or substantially the same level of expression of BACH1 relative to a control sample or to a cut-off value; wherein the first therapeutic regimen excludes a BACH1 inhibitor; or administering a second therapeutic regimen comprising a BACH1 inhibitor and an ETC inhibitor to the subject after a biological sample from the subject was determined to have an increased level of expression of BACH1 relative to a control sample or a cut-off value.

Further aspects of the disclosure relate to a method for treating cancer in a subject comprising: administering a first therapeutic regimen comprising an ETC inhibitor and/or chemotherapeutic agent to the subject after a biological sample from the subject was determined to have a decreased or substantially the same level of expression of BACH1 relative to a control sample or to a cut-off value; wherein the first therapeutic regimen excludes a BACH1 inhibitor; or administering a second therapeutic regimen comprising i) BACH1 inhibitor and ii) an ETC inhibitor and/or a chemotherapeutic agent to the subject after a biological sample from the subject was determined to have an increased level of expression of BACH1 relative to a control sample or a cut-off value.

Further aspects of the disclosure relate to a method for treating cancer in a subject comprising: administering a first therapeutic regimen comprising an ETC inhibitor and/or chemotherapeutic agent to the subject after a biological sample from the subject was determined to have a decreased or substantially the same level of expression of BACH1 relative to a control sample or to a cut-off value; wherein the first therapeutic regimen excludes a BACH1 inhibitor; or administering a second therapeutic regimen comprising i) BACH1 inhibitor and ii) a chemotherapeutic agent to the subject after a biological sample from the subject was determined to have an increased level of expression of BACH1 relative to a control sample or a cut-off value.

Further aspects of the disclosure relate to a method for predicting a subject's response to an ETC inhibitor, the method comprising: determining that the subject will be responsive to an ETC inhibitor after a biological sample from the subject was determined to have a decreased or substantially the same level of expression of BACH1 relative to a control sample or cut-off value; or determining that the subject will not be responsive to an ETC inhibitor after a biological sample from the subject was determined to have an increased level of expression of BACH1 relative to a control sample or cut-off value. In some embodiments, the method further comprises treating the subject determined to not be responsive to an ETC inhibitor with a therapeutic regimen comprising a BACH1 inhibitor and an ETC inhibitor that is effective in sensitizing the cancer treatment to the ETC inhibitor.

Further aspects of the disclosure relate to a method for predicting a subject's response to a chemotherapeutic agent, the method comprising: determining that the subject will be responsive to a chemotherapeutic agent after a biological sample from the subject was determined to have a decreased or substantially the same level of expression of BACH1 relative to a control sample or cut-off value; or determining that the subject will not be responsive to a chemotherapeutic agent after a biological sample from the subject was determined to have an increased level of expression of BACH1 relative to a control sample or cut-off value. In some embodiments, the method further comprises treating the subject determined to not be responsive to a chemotherapeutic agent with a therapeutic regimen comprising a BACH1 inhibitor and a chemotherapeutic agent that is effective in sensitizing the cancer treatment to the chemotherapeutic agent.

In some embodiments, the BACH1 inhibitor comprises a nucleic acid inhibitor, a polypeptide inhibitor, or a molecular inhibitor. In some embodiments, the molecular inhibitor comprises a porphyrin derivative. In some embodiments, the molecular inhibitor comprises hemin. In some embodiments, the molecular inhibitor comprises panhematin. In some embodiments, the polypeptide inhibitor comprises an antibody. In some embodiments, the nucleic acid inhibitor comprises a shRNA, an antisense molecule, or a siRNA.

In some embodiments, the ETC inhibitor comprises metformin, metformin derivatives, rotenone, antimycin A, or a biguanide. In some embodiments, the ETC inhibitor comprises a ETC inhibitor described herein.

In some embodiments, the chemotherapeutic agent comprises capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), albumin-bound paclitaxel, thiotepa, vincristine, liposomal doxorubicin, and/or vinorelbine.

In some embodiments, the BACH1 inhibitor is administered at the same time as the ETC inhibitor. In some embodiments, the BACH1 inhibitor and the ETC inhibitor are administered in the same composition. In some embodiments, the BACH1 inhibitor is administered prior to the ETC inhibitor. In some embodiments, at least one dose of the BACH1 inhibitor is administered at least one week prior to the administration of the ETC inhibitor. In some embodiments, at least 1, 2, 3, 4, 5, 6, 7, 8, 9, or 10 doses (or any derivable range therein) are administered at least, or at most, or exactly 1, 2, 3, 4, 8, 16, or 24 hours or 2, 3, 4, 5, 6, or 7 days, or 1, 2, 3, 4, 5, 6, 7, 8, 9, or 10 weeks (or any derivable range therein) prior to the administration of the ETC inhibitor.

In some embodiments, the BACH1 inhibitor is administered at the same time as the ETC inhibitor and/or the chemotherapeutic agent. In some embodiments, the BACH1 inhibitor and the ETC inhibitor and/or chemotherapeutic agent are administered in the same composition. In some embodiments, the BACH1 inhibitor is administered prior to the ETC inhibitor and/or chemotherapeutic agent. In some embodiments, at least one dose of the BACH1 inhibitor is administered at least one week prior to the administration of the ETC inhibitor and/or chemotherapeutic agent. In some embodiments, at least 1, 2, 3, 4, 5, 6, 7, 8, 9, or 10 doses (or any derivable range therein) are administered at least, or at most, or exactly 1, 2, 3, 4, 8, 16, or 24 hours or 2, 3, 4, 5, 6, or 7 days, or 1, 2, 3, 4, 5, 6, 7, 8, 9, or 10 weeks (or any derivable range therein) prior to the administration of the ETC inhibitor and/or chemotherapeutic agent.

In some embodiments, the administration comprises intratumoral, intravenous, peri-tumoral, oral, or sub-cutaneous. In some embodiments, the mode of administration is a mode described herein. In some embodiments, the cancer comprises breast cancer, colon cancer, prostate cancer, melanoma, ovarian cancer, liver cancer, or pancreatic cancer. In some embodiments, the cancer comprises a cancer described herein. In some embodiments, the cancer comprises breast cancer. In some embodiments, the breast cancer comprises triple negative breast cancer (TNBC).

In some embodiments, the subject has been determined to have an increased expression of BACH in a biological sample from the subject compared to a control. In some embodiments, the subject has been determined to have an increased expression of BACH1 in a biological sample from the subject based on a cut-off value. In some embodiments, the control comprises the level of expression of BACH1 in a non-cancerous biological sample. In some embodiments, the cut-off value or control level of expression is based on the expression of or average expression of BACH1 in patients that have cancer and are susceptible or not susceptible to an ETC inhibitor. In some embodiments, the cut-off value or control level of expression is based on the expression of or average expression of BACH1 in patients that have cancer and are susceptible or not susceptible to a chemotherapeutic agent. For example, the patient may be classified as having low expression of BACH1 when the expression level of BACH1 is similar to, not significantly different, or within 1, 2, 3, or 4 standard deviations of the expression level of or average expression level of BACH1 in patients that have been determined to be responders to ETC inhibitor therapy or chemotherapy. Similarly, the patient may be classified as having high expression of BACH1 when the expression level of BACH1 is similar to, not significantly different, or within 1, 2, 3, or 4 standard deviations of the expression level of or average expression level of BACH1 in patients that have been determined to be unresponsive or poorly responsive to ETC therapy or chemotherapy. Methods for determining expression levels, parsing patient populations, and determining cut-off values are known in the art and may include, for example, a Receiver Operating Characteristic (ROC) curve analysis.

In some embodiments, the increased expression comprises an increase in the BACH1 protein, an increase in the BACH1 mRNA, and/or an increased genomic copy number of the BACH1 gene. In some embodiments, the increased expression comprises an increased genomic copy number of the BACH1 gene. In some embodiments, the copy number of BACH1 in a biological sample from the subject is determined to be three or more. In some embodiments, the copy number of BACH1 in a biological sample from the subject is determined to be at least, at most, or exactly 3, 4, 5, 6, 7, 8, 9, or more (or any derivable range therein).

In some embodiments, the subject has previously been treated for the cancer. In some embodiments, the subject was determined to be resistant to the previous cancer treatment. In some embodiments, the previous treatment comprises an ETC inhibitor. In some embodiments, the previous treatment comprises a chemotherapeutic agent. In some embodiments, the subject has been diagnosed with cancer.

In some embodiments, the method further comprises determining the level of BACH1 in a biological sample from the subject. In some embodiments, determining the level of expression comprises determining the genomic copy number of BACH1 in a biological sample from the subject. In some embodiments, determining the level of BACH1 expression in a biological sample from the subject comprises determining the mRNA or protein expression of the BACH1 gene. In some embodiments, determining the level of expression comprises performing fluorescence in situ hybridization (FISH), enzyme-linked immunosorbent assay (ELISA), comparative genomic hybridization (CGH), real time PCR, southern blot, western blot analysis, microarray analysis, or immunohistochemistry. In some embodiments, the method further comprises an assay or detection method described herein.

In some embodiments, the method further comprises determining the level of expression or activity of the Electron Transport Chain (ETC) or the expression or activity of a complex or protein that is part of the ETC in a biological sample from the subject. In some embodiments, determining the level of expression comprises determining the level of ETC (or complex/gene associated therewith) expression in a biological sample from the subject comprises determining the mRNA or protein expression of the ETC. In some embodiments, determining the level of expression comprises performing fluorescence in situ hybridization (FISH), enzyme-linked immunosorbent assay (ELISA), comparative genomic hybridization (CGH), real time PCR, southern blot, western blot analysis, microarray analysis, or immunohistochemistry. In some embodiments, the method further comprises an assay or detection method described herein.

In some embodiments, the method further comprises administration of a further therapeutic agent. In some embodiments, the further therapeutic agent comprises a Bcl2 inhibitor. In some embodiments, the further therapeutic agent is a therapeutic agent described herein.

In some embodiments, the further therapeutic agent comprises an iron chelator treatment. In some embodiments, the iron chelator treatment comprises desferrioxamine. In some embodiments, the iron chelator treatment comprises deferasirox.

Further aspects of the disclosure relate to a composition comprising a BACH1 inhibitor and an ETC inhibitor. Further aspects of the disclosure relate to a composition comprising a BACH1 inhibitor and a chemotherapeutic agent. In some embodiments, the BACH1 inhibitor comprises a nucleic acid inhibitor, a polypeptide inhibitor, or a molecular inhibitor. In some embodiments, the molecular inhibitor comprises porphyrin derivatives. In some embodiments, the polypeptide inhibitor comprises an antibody. In some embodiments, the nucleic acid inhibitor comprises a shRNA, an antisense molecule, or a siRNA. In some embodiments, the ETC inhibitor comprises metformin, metformin derivatives, rotenone, antimycin A, or a biguanide. In some embodiments, the composition is formulated for intra-tumoral, intravenous, peri-tumoral, oral, or sub-cutaneous administration. In some embodiments, the composition is formulated for a route of administration described herein. In some embodiments, the composition further comprises an additional therapeutic agent. In some embodiments, the additional therapeutic agent comprises a Bcl2 inhibitor.

In some embodiments of the above disclosed aspects, the method further comprises recording the expression level or the prognosis score in a tangible medium. In some embodiments, the method further comprises reporting the expression level or the prognosis score to the patient, a health care payer, a physician, an insurance agent, or an electronic system. In some embodiments, the method further comprises monitoring the patient for cancer recurrence or metastasis or prescribing a treatment that excludes the previously prescribed treatment. The treatment may be any treatment described herein.

Certain methods may involve the use of a normalized sample or control that is based on one or more cancer samples that are not from the patient being tested. Methods may also involve obtaining a biological sample comprising cancer cells from the patient or obtaining a cancer sample.

Methods may further comprise assaying nucleic acids or testing protein expression in the cancer sample. In some embodiments, assaying nucleic acids comprises the use of PCR, microarray analysis, next generation RNA sequencing, any methods known in the art, or a combination thereof. In further embodiments, testing protein expression comprises ELISA, RIA, FACS, dot blot, Western Blot, immunohistochemistry, antibody-based radioimaging, mass spectroscopy, any methods known in the art, or a combination thereof.

In some embodiments, the expression level is elevated or reduced relative to a control level of expression, such as a non-metastatic cancer or non-cancerous tissue. In some embodiments, the control level is a mean, an average, a normalized value, or a cut-off value. In some embodiments, the control level of expression is the level of expression in non-metastatic breast cancer. In some embodiments, the control level of expression is the level of expression in non-cancerous tissue. In some embodiments, the control is a cancerous tissue or a metastatic breast cancer tissue, and one skilled in the art would understand that a patient would be predicted to have metastatic breast cancer when the expression level of the measured genes in the patient sample is the same, or not significantly different, or within 1 or 2 standard deviations from a control that represents a level in metastatic breast cancer tissues.

In some embodiments, the expression or activity level of a protein is determined or has been from a biological sample from a patient or a control. In certain embodiments the sample is obtained from a biopsy from the tissue by any of the biopsy methods described herein or known in the art. In other embodiments the sample may be obtained from any of the tissues provided herein that include but are not limited to gall bladder, skin, heart, lung, pancreas, liver, muscle, kidney, smooth muscle, bladder, intestine, brain, prostate, esophagus, or thyroid tissue. Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample. In some embodiments, the biological sample may be from a tumor, a cyst, or neoplastic tissue.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of polypeptides described herein, such as BACH1 or ETC genes.

In certain embodiments, a microarray may be used to measure or assay the level of protein expression in a sample. The methods may further comprise recording the expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of one or more genes, meaning that the expression or activity level of a gene is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a gene or protein.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene or protein in a sample from a patient; and b) determining a difference value in the expression or activity levels using the information corresponding to the expression or activity levels in the sample compared to a control or reference expression or activity level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for cancer, administering the same treatment as the first treatment to the patient if the patient does not have increased expression or activity level; administering a different treatment from the first treatment to the patient if the patient has increased expression or activity level.

In some embodiments, receiving information comprises receiving from a tangible data storage device information corresponding to the expression or activity levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional therapy if the patient does not have expression or activity levels, and/or or treating the patient with an alternative therapy if the patient has increased expression or activity levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a thymidylate synthase inhibitor to a patient that is determined to have a decreased expression or activity level.

It is contemplated that any method or composition described herein can be implemented with respect to any other method or composition described herein and that different embodiments may be combined.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-E. BACH1 is enriched and negatively correlates with oxidative phosphorylation in breast cancer. A, BACH1 expression (RNA-seq) in the TNBC subset of breast cancer patients compared to non-TNBC patients using TCGA (provisional n=1105, left), METABRIC (n=2509, middle) and Pam50 categories of TCGA (right). P-values by two-tailed student's t-test. B, BACH1 protein blots using cell line lysates from primary human mammary epithelial cells (HMPEC), MCF10A, T47D, SUM159PT, MDA-MB468 (MB468), Hs578T, BM1, MDA-MB436 (MB436), MDA-MB157 (MB157), and BT549. C, KEGG pathways demonstrating the negative correlation between BACH1 expression and oxidative phosphorylation in all breast cancer patients (left) and TNBC patients (right). FDR values ($-\log_{10}$ FDR) shown. D, BACH1 protein blots of BM1-shBACH1 and control cells. Representative images of more than 5 independent assays are shown (top). Gene ontology (GO) terms for cell components that are positively correlated with BACH1 depletion based on microarray analysis of transcripts from BM1-shBACH1 cells as determined by Gene Set Analysis (p<0.05, FDR<5%). E, Plots of gene set enrichment analysis (GSEA) of BACH1-regulated genes, and a heat-map depicting changes in gene expression levels involved in "mitochondrial inner membrane" based on microarray data from BM1-shBACH1 and control cells (n=3/cell lines). Each column represents a biological replicate.

FIG. 2A-H. BACH1 transcriptionally regulates mitochondrial electron transport genes and mitochondrial respiration in TNBC. A, Plot of relative mRNA levels of mitochondrial inner membrane genes in BM1-shBACH1 cells (#1, 2 refer to two distinct shBACH1 vectors) compared to the wild type control (BM1-shCont) by qRT-PCR (left). Protein blots of BACH1 in BM1-shBACH1 cell lysates using antibodies to BACH1 or alpha-TUBULIN (a-TUB) (right). B, Protein blots of ETC genes using BM1-shBACH1 (#1) and control cell lysates. Samples were probed with antibodies to proteins as indicated. Protein blots (in A, B) are representative images of more than 3 independent assays. C, BACH1 and H3K27Me3 recruitment to the promoter regions of ETC genes compared to IgG binding using BM1 and MB468 cells. D, Measurement of metabolic phenotypes of BACH1-depleted breast cancer cells for OCR (left) treated with oligomycin (2 μM) and ECAR (right) fueled with glucose (10 mM). Values represent mean±s.d of 6 biological replicates with p-values (p<0.01, *p<0.001) determined by two-tailed student's t-test. E, Relative abundance of 13C labeled metabolites derived from 13C-glucose in BM1-shBACH1 compared to control cells. F, Fractional abundance of 13C metabolites relative to total metabolites (12C and 13C) of BM1-shBACH1 and control cells. Metabolomics values in E and F are mean±s.e.m from n=5/cell lines with p-values (*p<0.05, ***p<0.001) by two-tailed student's t-test. G, Plot of relative mRNA of PDK and PDH genes and blots of protein levels of PDK, PDH, and phosphorylated PDH (Ser293) in BM1-shBACH1 (#1) and its control cells. Protein blots are representative images of three independent assays. H, Relative BACH1 and RNA Polymerase II enrichment in the promoter regions of PDK genes compared to IgG binding using BM1 and MB468 cells. In A, C, G, and H, values are mean±s.e.m of three independent assays with p-values (*p<0.05, p<0.01, *p<0.001, ****p<0.0001) determined by two-tailed student's t-test.

FIG. 3A-D. BACH1 confers resistance to mitochondrial respiratory inhibitors in TNBC. A, Plots of viability (%) of BM1-shBACH1 or control cells (shCont) when treated with metformin, rotenone, or antimycin A, as indicated, for 48 hours. Cells were assayed by staining with CaAM (1 uM). Values are mean±s.e.m of 6 biological replicates with p-values (*p<0.05, **p<0.01) determined by two-tailed Student's t-test B, Plots of NAD+/NADH ratios measured after addition of pyruvate (2.5 mM) to shBACH1 cells. Values are mean±s.e.m of 3 biological replicates with p-values (*p<0.05) determined by two-tailed Student's t-test. C, Viability (%) of BM1-shBACH1 and control cells when treated with metformin in growth media containing 2.5 mM glucose and supplemented with pyruvate (2.5 mM). D, Plot of % confluence of BM1-shBACH1 cells transfected with siRNA for COX15 or UQCRC1 and treated with metformin (10 mM). Cell viability was monitored and shown as growth (%). For viability assays in C, D, values are mean±s.e.m of 6 biological replicates with p-values (NS=not significant, ****p<0.0001) determined by two-tailed paired Student's t-test.

FIG. 4A-I. Pharmacological BACH1 degradation by hemin in TNBC. A, Plot of relative mRNA levels of mitochondrial inner membrane genes in BM1 and MB436 cells treated with hemin (20 μM) for 48 hours. The 4 bars shown for each membrane gene represent (from left to right) BM1-vehicle, MB436-Vehicle, BM1-Hemin, and MB436-Hemin. Values are mean±s.e.m of three independent assays with p-value (*p<0.05, **p<0.01) determined by two-tailed student's t-test. B, Protein blots of ETC genes using lysates from BM1 and MB436 cells treated with hemin. Representative blots of at least three independent assays are shown. C, Measurement of OCR (left) and ECAR (right) of BM1 cells pre-treated with hemin or control overnight. Values are mean±s.e.m of 8 biological replicates with p-values (*p<0.05, p<0.01) determined by two-tailed Student's t-test. D, Plots of viability (%) of BM1 cells treated with hemin and ETC inhibitors (metformin, rotenone, and antimycinA) as indicated for 48 hours. E, MB468 cells transfected with BACH1 (pCDH-BACH1) overnight were plated in 96 well plates and treated with metformin and/or hemin. After 48 hours of treatment, cells were stained with CaAM for viability. F, Protein blots of BACH1 using cell lysates. Representative images of 3 independent assays are shown. G, Plots of viability (%) of BM1-shBACH1 cells transfected with mut Bach1 (100 ng) and treated with hemin for 48 hours. H, Protein blots for BACH and alpha-tubulin using cell lysates. Representative images of 3 independent assays are shown. I, Relative HMOX1 mRNA levels of BM1-shBACH1 and control cells transfected with mut Bach1 and treated with hemin. Values are mean±s.e.m of 3 independent assays with p-values (*p<0.001) assessed by two-tailed student's t-test. For viability assay in D, E, H, values are mean±s.e.m. of 6 biological replicates. P-values (*p<0.05, **p<0.01) are determined by two-tailed Student's t-test in D, or by two-tailed paired Student's t-test in E and H.

FIG. 5A-J. Combination treatment with hemin and metformin suppresses growth of TNBC tumors. A, Plot of tumor volume of mice (n=6-7 mice/group) orthotopically injected with MB436-shBACH1 or shCont cells and treated with metformin (200 mg/kg) in drinking water ad libidum. Tumor sizes are mean±s.e.m with p-value (**p<0.0001) determined by two-tailed paired t-test. B, Protein blots of phosphorylated PDH (Ser293) and PDH using tumor lysates from representative MB436-xenograft mice (n=3/group). Representative images from two independent assays are shown. C, Plot of primary tumor-free (%) mice indicates the ratio of mice that lost tumors upon metformin treatment compared to the total number of mice per treatment group at the end of experiment. D, Plot of lung metastases of mice injected with MB436-shBACH1 or shCont and treated with metformin. Fixed and sliced lungs (n=5 mice/group) were stained with H&E and assessed for metastasis. Lung metastases per stained slide (n=6) are shown as mean±s.e.m with p-value (*p<0.0001, ****p<0.00001) determined by two-tailed paired student's t-test. E, BACH1 protein blots using tumor lysates from representative mice of different TNBC models using α-TUBULIN as a loading control. F, Plot of tumor volume of C3(1)-TAg mice, a transgenic mouse TNBC model. After 10 days of mice developed palpable tumors at age of 15 weeks, mice (n=5/group) were treated with metformin (200 mg/kg/day) until the end of experiment. Tumor volumes are mean±s.e.m with p-value (*p<0.05) by one-tailed student's t-test. G, Plot of tumor volume of MB436 xenograft tumors (n=9/group) injected with MB436 cells ($2 \times 10^6$ cells) and started to treat with hemin (50 mg/kg/day, i.p) and metformin (200 mg/kg/day) at days 14 and 21, respectively. Tumor volumes are mean±s.e.m with p-value (**p<0.01) by two-tailed paired student's t-test. H, Plot of tumor volume of patient-derived xenograft (PDX) that are treated with hemin (50 mg/kg/day) and metformin (300 mg/kg) at day 21 and monitored. Tumor volumes are mean±s.e.m with p-values; *p<0.05, p<0.01, *p<0.001, ****p<0.0001, n.s=not significant, determined by two tailed paired t-test (n=9-10/group). I, Protein blots of phosphorylated PDH (Ser293) and PDH using tumor lysates from representative PDX mice (n=3/group). Representative images from two independent assays are shown. J, Proposed schematic model summarizing BACH1 regulation of metabolic pathways by inhibiting ETC gene expression and activating PDH by inducing PDK1 expression; targets of combination therapy by metformin (ETC) and hemin (BACH1) are shown.

FIG. 6A-H. Inverse correlation between BACH1 and ETC genes in cancer patients. A, Expression plots showing a correlation UQCRC1 or ATP5D with BACH1 based on TCGA breast cancer (n=1105) and TNBC (n=119) patient data. Pearson's and Spearman's correlations are shown. B-D, Expression of ETC genes (COX15, ATP5D, ATP5G2) in TNBC compared to non-TNBC patients using multiple patient data sets; (B) METABRIC (n=2509), (C) GSE2034 (n=286), and (D) GSE11121 (n=200). Red bar indicates mean value with p-value by two-tailed student's t-test. E, Oncoprint analysis demonstrating expression status of BACH1 and ETC genes for each patient in breast cancer (TCGA provisional dataset: n=1105). Genes with expression z-scores are shown. F, Frequency (%) of patient tumors with overexpression of BACH1 compared to their matched normal tissues across multiple TCGA cancer types. Number of patients are indicated in the plot. G, Heat-map showing FDR values ($-\log_{10}$ FDR) of KEGG pathways that are negatively correlated with BACH1 across major TCGA cancer types. Only those KEGG pathways commonly enriched to all cancer types studied were displayed on the heat-map. H, Coexpression of UQCRC1 and BACH1 in TCGA cancers (skin, prostate, colorectal, pancreas, lung and liver). Pearson's (<-0.3) and Spearman's (<-0.3) correlations are shown.

FIG. 7A-B. BACH1 expression is enriched in basal-like breast cancer. A, BACH1 expression levels (RNA-seq) with respect to DNA copy-number alterations observed in all TCGA breast cancer cases (patients n=1105) (left). BACH1 expression in basal-like breast cancer patients as indicated by Pam50 classification compared to the non-basal patients (right). P-value (p=0.0035) by two-tailed t-test. B, Gene ontology (GO) terms for biological processes that are positively correlated with BACH1 depletion based on microarray analysis of transcripts from BM1-shBACH1 cells as determined by Gene Set Analysis (p<0.05, FDR<5%).

FIG. 8A-F. BACH1 binds to the promoter regions of ETC genes as a suppressor in TNBC. A, Plot of relative mRNA levels of mitochondrial inner membrane ETC genes in MB436-shBACH1 cells (#1,2 refer to two distinct shBACH1 vectors) compared to the wild type control (MB436-shCont) by qRT-PCR. Values represent mean of three independent assays±s.e.m. with p-value (*p<0.05) determined by two-tailed student's t-test. B, Protein blots of ETC genes and a-TUBULIN using MB436-shBACH1 cell lysates. Representative images of more than three independent assays are shown. C, Relative mRNA levels of mitochondrial inner membrane genes in MDA-MB231 cells expressing siBACH1 or control siRNA by qRT-PCR. Values represent mean of three biological replicates±s.e.m with p-value (*p<0.05, **p<0.01) determined by two-tailed student's t-test. BACH1 knockdown by siRNA is shown in protein blot (right). Protein blots of two independent assays are shown. D, Schematic diagram showing proximal BACH1 binding on the promoter regions of ETC genes and PDK genes. TSS indicates transcriptional start site. Arrows indicate primers used for ChIP-PCR. E, Plots of ChIP assays showing fold enrichment of BACH1 recruitment to the HMOX1 promoter using BACH1-depleted TNBC (BM1 and MB436; right bar above IgG and BACH1) or control cells (left bar above IgG and BACH1). F, Plots of ChIP assays showing fold enrichment of BACH1 recruitment to ETC genes in MB436 cells and MB468 cells. For ChIP assays in e and f, values represent mean of three biological replicates±s.e.m. with p-value (*p<0.05, p<0.01, *p<0.001) determined by two-tailed student's t-test.

FIG. 9A-I. BACH1 depletion activates mitochondrial oxidative phosphorylation in TNBC. A, Measurement of metabolic phenotypes, OCR and ECAR, of TNBC cells expressing control or shBACH1. For OCR analysis, cells in mito-stress test base medium (10 mM Glucose, 2 mM Glutamine, 1 mM Pyruvate, pH 7.4) were monitored 3 times every 3 minutes by diffusing inhibitors such as 2 µM of oligomycin, 2 µM of FCCP, and 0.5 µM of Rotenone/AntimycinA (left). For ECAR analysis, cells in medium (2 mM Glutamine, pH 7.35) were monitored 3 times every 3 minutes by diffusing 10 mM of glucose followed by inhibitors such as 1 µM of oligomycin and 50 mM of 2-DG (right). Values represent mean of six biological replicates±s.e.m; *p<0.05, **p<0.01 determined by two-tailed student's t-test. B, Measurement of lactate levels (µM) in growth media produced by BM1 and MB436 cells stably expressing control shRNA or shBACH1 overnight in 6 well plate. Values represent mean of three biological replicates±s.e.m; *p<0.05 determined by two-tailed student's t-test. C, Relative abundance of 13C glucose-derived labeled metabolites, glycerol 3-phosphate and phosphoribosyl pyrophosphate (PRPP) in BM1-shBACH1 compared to control cells. D, Steady state metabolomics of BM1-shBACH1 and control cells cultured under high glucose (25 mM) DMEM using Mass spectrometry. Metabolites involved in the TCA cycle and antioxidants are shown. E, Steady state metabolomics involved in glycolysis pathways of BM1-shBACH1 and control cells cultured under low glucose (10 mM) DMEM using Mass spectrometry. For all metabolomics data (in c-e), values are mean of five replicates±s.e.m; *$p<0.05$, **$p<0.01$ by two-tailed student's t-test .F, Plot of NAD+/NADH ratios in BM1 or MB436 cells expressing control or shBACH. Values are mean±s.e.m of 3 biological replicates with p-values (*$p<0.05$) by two-tailed student's t-test. G, Relative mRNA levels of pyruvate carboxylase (PC) in shBACH1 cells compared to control. Values are mean±s.e.m of 3 biological replicates with NS indicates not significant by two-tailed student's t-test. H, Left; Protein blots of PDK, PDH, and phosphorylated PDH (Ser293) in MB436-shBACH1 cells compared to controls. Representative blots of more than three independent assays are shown. Right; Relative mRNA levels of PDH and PDK genes in MB436-shBACH1 cells compared to wild type control. Values represent mean of three biological replicates±s.e.m. with *$p<0.05$ determined by two-tailed student's t-test. I, Plots of ChIP assays showing fold enrichment of BACH1 recruitment to PDK genes using MB436 and MB468 cells. Values represent mean of three independent assays s.e.m; *$p<0.05$, **$p<0.01$ determined by two-tailed student's t-test.

FIG. 10A-D. BACH1 levels determine responses to ETC inhibitors in TNBC. A, Plot showing real time cellular growth as measured by confluency (%) of BM1-shBACH1 and BM1-shCont cells treated with metformin. After 20 hours of plating cells, metformin (0.25, 0.5, and 1 mM) was added in the growth media. B, Cell viability (%) measured by CaAM staining of MB436-shBACH1 and control cells treated with metformin, rotenone, or antimyinA as indicated for 48 hours. C, Plot showing real time cellular growth as measured by confluency (%) of MB436-shBACH1 and MB436-shCont cells treated with rotenone, antimycin A or metformin, as indicated. D, Plots of cell viability measured by CaAM staining of non malignant mammary epithelial cells (MCF10A, top, and 184A1, bottom) treated with metformin, rotenone, or antimycin A as indicated for 48 hours. For viability assays, values represent mean of six biological replicates±s.e.m. with p-values (*$p<0.05$, $p<0.01$, *$p<0.001$, ****$p<0.0001$) determined by paired two-tailed student's t-test in a and c, or by two-tailed t-test in b.

FIG. 11A-H. BACH1 levels in cells determine resistance to metformin treatment in TNBC. A, Protein blots of BACH1 and a-TUBULIN in MB468, MB436 and BM1 cells. Representative images of more than 3 independent assays are shown. B, Plot showing real time cellular growth as measured by confluency (%) of MB468, MB436, and BM1 cells treated with metformin (1 mM) after 24 hours of plating cells. C, Plots of cell viability measured by CaAM staining of MB468, MB436, and BM1 cells treated with metformin (1,3,5.10 mM) for 48 hours. Values represent mean of six biological replicates±s.e.m.; *$p<0.05$, $p<0.01$, *$p<0.001$, determined by two-tailed student's t-test. D-E, Relative mRNA levels of OCT1, PPARg and PCG1α in BM1-shBACH1 cells and control cells. F, Relative mRNA expression of COX15 and UQCRC1 in BM1-shBACH1 transfected with siRNA for COX15 or UQCRC1. For qRT-PCR analysis in d-f, values represent mean of three biological replicates±s.e.m. with p-value ($p<0.01$, *$p<0.001$) by two-tailed student's t-test. G, Protein blots of COX15 and a-TUBULIN and mRNA gene expression in BM1-shBACH1 cells transfected with siCOX15 (150 nM) or siUQCRC1 (150 nM) for 72 hours. Representative images from 2 independent assays are shown. H, Plot of growth of BM1-shBACH1 cells transfected with siCOX15 and siUQCRC1. Metformin (10 mM) was added 18 hours after plating of cells. For viability assays in B and H, values represent mean of six biological replicates±s.e.m. with non-significant (NS), *$p<0.001$, and **$p<0.0001$ determined by paired two-tailed student's t-test.

FIG. 12A-N. Pharmacological suppression of BACH1 using hemin. A, Plot of growth as measured by confluency (%) of BM1 cells treated with hemin (10, 20, 40, or 80 μM). Hemin was treated after 24 hours as indicated as an arrow. Values represent mean of six biological replicates±s.e.m. B, Protein blots of BACH1 levels in BM1 and MB436 cells treated with Hemin for 4 or 24 hours. Representative images of more than 4 independent assays are shown. C, HMOX1 mRNA levels in BM1 cells treated with hemin (10 or 20 μM) or vehicle as indicated. Values represent mean of three biological replicates±s.e.m. D, Measurement of OCR and ECAR of BM1 cells treated with hemin. For OCR analysis, cells in mito-stress test base medium (10 mM Glucose, 2 mM Glutamine, 1 mM Pyruvate, pH 7.4) were monitored 3 times every 3 minutes by diffusing inhibitors such as 2 μM of oligomycin, 2 μM of FCCP, and 0.5 μM of Rotenone/AntimycinA (left). For ECAR analysis, cells in medium (2 mM Glutamine, pH 7.35) were monitored 3 times every 3 minutes by diffusing 10 mM of glucose followed by inhibitors such as 1 μM of oligomycin and 50 mM of 2-DG (right). Values represent mean of six biological replicates±s.e.m.; *$p<0.05$ determined by two-tailed student's t-test. E, Plot of growth by confluency (%) of BM1 cells treated with hemin (20 μM) and metformin (5.10 mM). Values represent mean of six biological replicates±s.e.m.; **$p<0.0001$ by paired two-tailed student's t-test. F, Cell viability with CaAM (left) and cell growth as measured by % confluency (right) of MB436 cells treated with hemin (20 μM) and metformin (1,3,5.10 mM) are shown. Values represent mean of six biological replicates s.e.m.; *$p<0.001$, ****$p<0.0001$ by paired two-tailed student's t-test. G, Protein blots of BACH1, UQCRC1 and α-TUBULIN in BT549 cells treated with hemin (20 μM) for 48 hours. Relative mRNA levels of mitochondrial inner membrane genes in BT549 cells treated with hemin (20 μM; right bar above each gene) or vehicle (left bar above each gene) for 48 hours. Values represent mean of three independent biological assays s.e.m.; *$p<0.05$, $p<0.01$ by paired two-tailed student's t-test. H, Cell viability of BT549 cells with CaAM treated with hemin (20 μM) and metformin (1,3,5.10 mM) are shown. Values represent mean of six biological replicates±s.e.m.; $p<0.01$ by two-tailed student's t-test. I, Plot of % confluency of BT549 cells treated with hemin (20 μM) and metformin (3 mM). Values represent mean of six biological replicates±s.e.m.; ****$p<0.0001$ by paired two-tailed student's t-test. J, Plot of % viability of MB436-shBACH1 cells transfected with wt BACH1 (pCDH-BACH1). After transient transfection of BACH1, cells were treated with hemin (20 μM) and metformin (0.25, 0.5 and 1 mM) for 48 hours for CaAM staining. Values represent mean of six biological replicates±s.e.m.; *$p<0.05$ by paired two-tailed student's t-test. K, Expression of BACH1 is shown in protein blots. Representative blot images of 3 independent assays are shown. L, Plot of % viability of MB436-shBACH1 cells transfected with mutant Bach1 (pCDH-Bach1 mut) transiently and treated with metformin (0.25, 0.5 and 1 mM) for 48 hours. Values represent mean of six biological replicates±s.e.m. NS indicates not significant. M, Protein blots of BACH1 levels in MB436 cells transfected with Bach1 mut and treated with hemin (20 μM) for 48 hours. Representative images of more than 4 independent assays are shown. N, Plot of growth of BM1-shBACH1 cells transiently transfected with Bach1 mut and treated with metformin (0.5, 1, and 5 mM) and measured by confluency (%). Values represent mean of six biological replicates±s.e.m. NS indicates not significant.

FIG. 13A-E. BACH1-depleted xenograft breast tumors respond to metformin treatment. A, Enlarged plots of inboxed from FIG. 5a showing reduction of MB436-shBACH1 tumor volume with metformin from week 2. B, Xenograft tumor weights from mice injected with MB436-shBACH1 or MB436-shCont (n=6-7/group). P-values (*p<0.05, p<0.01, *p<0.001) determined by two tailed student's t-test. C, Representative tumor images from each treatment group. Bar=2 cm. D, Tumor volumes and weight of xenografts (n=4/vehicle, n=6/metformin) injected with BM1-shBACH1 cells (2×106 cells) and treated with metformin (300 mg/kg/day) for 6 weeks. Values represent mean±s.e.m.; *p<0.05 and **p<0.01 by paired two-tailed student's t-test. Representative tumor images are shown. E, Expression of PDK and PDH mRNA in MB436-shBACH1 xenograft tumors (n=4/group) by qRT-PCR. Values represent mean of 4 tumors s.e.m.; *p<0.05 and **p<0.01 by two-tailed student's t-test.

FIG. 14A-G. Combination treatment using hemin and metformin decreases BACH1 levels and breast tumor growth. A, Expression levels of BACH1 protein from xenograft tumor treated with hemin. Mice injected with BM1 cells (2×106 cells) for 4 weeks were treated with 25 mg/kg or 50 mg/kg of hemin for the indicated times. Tumor lysates were analyzed by western blots using antibodies against BACH1 and a-TUBULIN. B, Expression of HMOX1 mRNA in xenograft tumors treated with hemin as indicated. C, Top: Schematics showing experimental plan for injection of hemin and metformin for a MB436 xenograft model. Bottom: Tumor weight measured at the end of treatment of metformin and hemin (n=8-9/group). Individual weights are plotted and shown as mean±s.e.m.; p<0.01 and *p<0.001 by two-tailed paired student's t-test. D, Representative tumors images from each treatment group are shown (bar=1 cm). E, Top: Schematic showing experimental time plan for injection of hemin and metformin for a PDX model. Bottom: Weight of PDX tumors measured at the end of treatment of metformin and hemin (n=9/vehicle, n=8/hemin, n=9/metformin, n=7/combination of hemin and metformin). Individual weights are plotted and shown as mean±s.e.m.; NS: non-significant, p<0.01 and *p<0.001 by two-tailed student's t-test. F, Representative images of MB436 xenograft tumors treated are shown. (bar=2 cm). G, Body weights of all the mice monitored before and during the treatment of hemin and metformin. All treatment group showed no changes of body weights during or after hemin and metformin treatment.

FIG. 15A-C. BACH1 expression is high in TNBC compared to non-TNBC patients (METABRIC, GSE2034, and GSE11121 data sets). A-C, BACH1 expression in TNBC compared to non-TNBC using METABRIC (n=2509), GSE2034 (n=286), and GSE11121 (n=200). Red bar indicates mean with p-value determined by two-tailed student's t-test.

DESCRIPTION OF ILLUSTRATIVE EMBODIMENTS

Figure 10C:
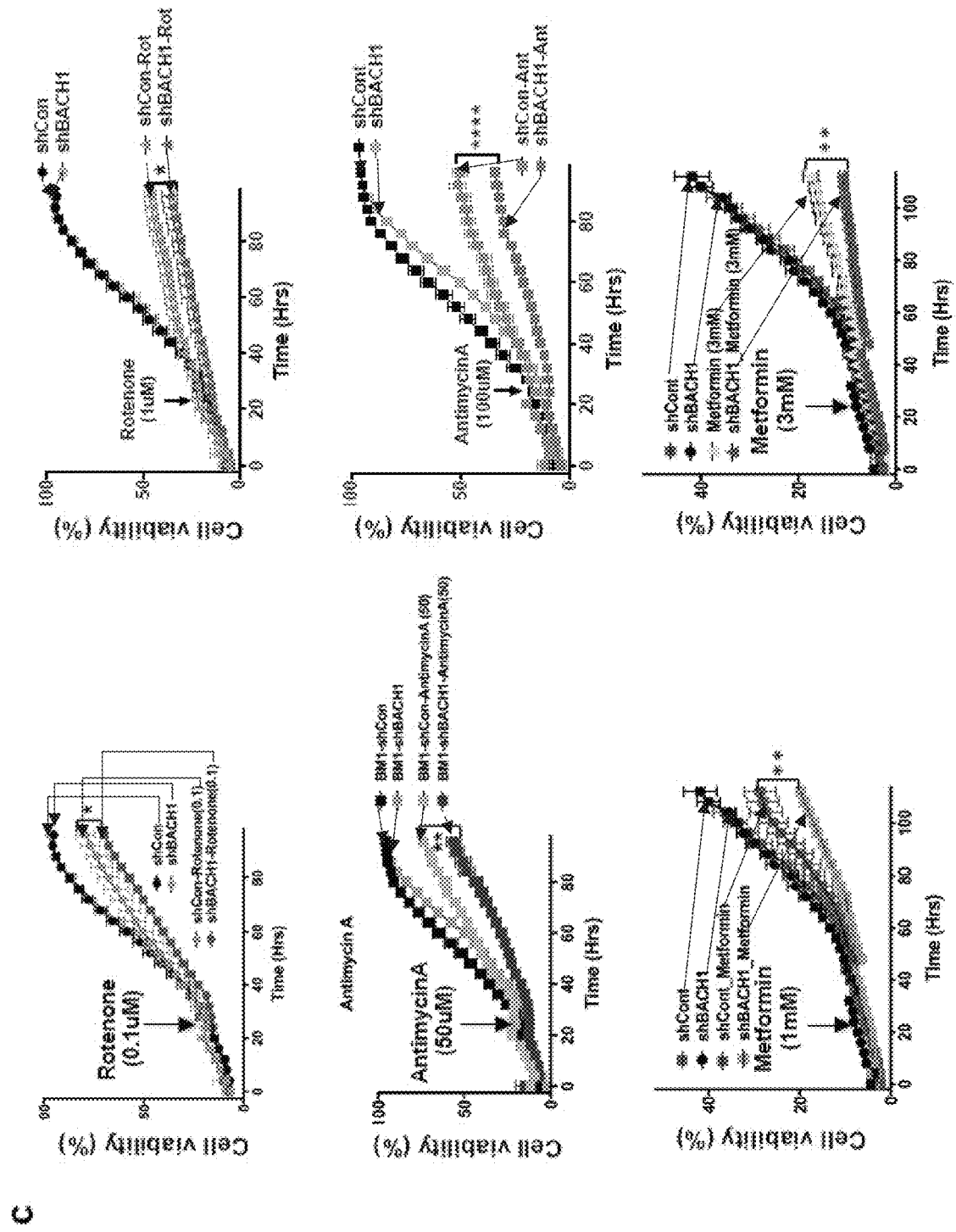

Aerobic glycolysis, as a major source of energy and biosynthetic precursors in tumors, represents a potential target that can be exploited for the treatment of cancer. Reprogramming metabolic pathways by controlling the balance between glycolysis and oxidative phosphorylation could improve the ability of metabolic inhibitors to suppress cancers with limited treatment options like triple negative breast cancer (TNBC). The inventors found that BACH1, a heme-binding transcription factor whose expression is enriched in patients with TNBC, enhances glycolysis and inhibits oxidative phosphorylation.

BACH1 is inhibited by the metastasis suppressor Raf Kinase Inhibitory Protein (RKIP) through a signaling pathway involving MAP kinase and let-7[12]. The BACH1 pathway metastasis gene signature (BPMS) is associated with poor outcome of TNBC patients.[15] As a member of the cap'n'collar (CNC) family of transcription factors, BACH1 plays numerous roles in controlling cellular stress responses including oxidative, xenobiotic, endoplasmic reticulum and inflammatory (reviewed[16]). A regulator of cellular redox states, BACH1 maintains heme homeostasis through a negative feedback loop[17,18]. Heme binding to BACH1 induces nuclear export and ubiquitin-dependent degradation of BACH1 in the cytoplasm[19]. BACH1 depletion results in de-repression of HMOX1, an enzyme that breaks down heme to CO, $Fe^{2+}$ and biliverdin[19]. Thus, BACH1 regulates cancer progression in multiple ways The inventors also found out that knockdown of BACH1 increases both tricarboxylic acid (TCA) cycle metabolites and gene expression of components in the electron transport chain (ETC) through loss of BACH1 binding to their promoters. Treatment of cells with an ETC inhibitor (e.g. hematin—aka hemin), which induces BACH1 degradation, mimics BACH1 depletion with shRNA. Since BACH1 depletion causes cellular dependence upon oxidative phosphorylation, the inventors determined the effect of BACH1 loss on tumor sensitivity to ETC inhibitors such as metformin, an anti-diabetic drug. Pretreatment of TNBC tumors with BACH1 shRNA or an ETC inhibitor such as hemin overcame metformin resistance and abolished the growth of both cell line and patient-derived tumor xenografts. Furthermore, an inverse correlation between BACH1 and ETC gene expression was observed in breast cancer patients as well as other tumor types raising the possibility that this relationship is clinically significant. The current disclosure is based, at least in part, on the discovery that the metabolic balance of cancer cells represents an Achilles heel that can be exploited through targeting BACH1 to sensitize breast cancer and potentially other tumor tissues to mitochondrial inhibitors.

I. DEFINITIONS

As used herein, the term "antibody" encompasses antibodies and antibody fragments thereof, derived from any antibody-producing mammal (e.g., mouse, rat, rabbit, and primate including human), that specifically bind to an antigenic polypeptide. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

The term substantially the same or not significantly different refers to a level of expression that is not significantly different than what it is compared to. Alternatively, or in conjunction, the term substantially the same refers to a level of expression that is less than 2, 1.5, or 1.25 fold different than the expression or activity level it is compared to.

A "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets. Also intended to be included as a subject are any subjects involved in clinical research trials not showing any clinical sign of disease, or subjects involved in epidemiological studies, or subjects used as controls.

The term "primer" or "probe" as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression," "increased level of expression," "elevated expression," "decreased expression," or "decreased level of expression" refers to an expression level of a biomarker in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that a numerical value discussed herein may be used with the term "about" or "approximately."

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The terms "protein", "polypeptide" and "peptide" are used interchangeably herein when referring to a gene product or functional protein.

The terms "ameliorating," "inhibiting," or "reducing," or any variation of these terms, when used in the claims and/or the specification includes any measurable decrease or complete inhibition to achieve a desired result.

The term "inhibitor" refers to a therapeutic agent that indirectly or directly inhibits the activity or expression of a protein, process (e.g. metabolic process), or biochemical pathway.

A person of ordinary skill in the art understands that an expression level from a test subject may be determined to have an elevated level of expression, a similar level of expression or a decreased level of expression compared to a reference level.

As used herein, "treating," "treatment" or "therapy" is an approach for obtaining beneficial or desired clinical results. This includes: reduce the alleviation of symptoms, the reduction of inflammation, the inhibition of cancer cell growth, and/or the reduction of tumor size. In some embodiments, the term treatment refers to the inhibition or reduction of cancer cell proliferation in a subject having cancer. Furthermore, these terms are intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21(7):1404-1411.

The term "therapeutically effective amount" refers to an amount of the drug that treats or inhibits cancer in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of BACH1 or ETC activity or expression.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

II. THERAPEUTIC AGENTS

A BACH1 inhibitor may inhibit at least 10, 15, 20, 25, 30, 35, 40, 45, 50, 55, 60, 65, 70, 75, 80, 85, 90, 95, or 100% of the protein's activity or expression. The inhibitor may directly interact with BACH1 or indirectly, by, for example, activating a BACH1 repressor or inhibiting a BACH1 activator. Inhibitors of BACH1 are known in the art.

A. BACH1 Molecular Inhibitors

In some embodiments, the inhibitor of BACH1 is a molecular inhibitor. Molecular inhibitors include molecules and small molecules that inhibit BACH1 expression and/or activity. Examples include: HPP971 (vTv Therapeutics), HPP-4382 (High Point Pharmaceuticals, LLC), BACH1 inhibitors described in WO 2016/089648, which is specifically incorporated by reference, porphyrin derivatives, hemin (panhematin—Chloro[3,7,12,17-tetramethyl-8,13-divinylporphyrin-2,18-dipropanoato(2-)]iron(III) CAS NO: 16009-13-5).

Porphyrin derivatives include, for example, Trapoxin B; ketones such as 2-amino-8-oxo-9,10-epoxy-decanoyl; propenamides such as 3-(4-aroyl-1H-pyrrol-2-yl)-N-hydroxy-2-propenamide, and hemin. Further porphyrin derivatives include 5,10-Diphenyl-15,20-di(N-methyl-3-pyridyl)-porphyrin; 5,10-Diphenyl-15,20-di(N-methyl-4-pyridyl)-porphyrin; 5,15-Diphenyl-10,20-di(N-methyl-3-pyridyl)-porphyrin; Protoporphyrin; Tetra(N-methyl-4-pyridyl)-porphyrin; Mesotetraphenylporphine; Protoporphyrin IX dimethyl ester; Tetra-(4-carboxyphenyl)-porphyrin; Tetra-(4-methylphenyl)-porphyrin; Tetra-(3-methylphenyl)porphyrin; Tetra-(4-hydroxyphenyl)-porphyrin; Fe(II)-tetraphenyl-porphyrin; Tetra-(4-chlorophenyl)-porphyrin; Fe(III)-tetra-(4-methylphenyl)-porphyrin; Fe(III)-tetra-(N-methyl-4-pyridyl)-porphyrin; and Fe(III)-mu-oxo-dimer of tetraphenylporphyrin.

Further examples of BACH1 inhibitors include: -Methyl-2-(6-trifluoromethoxy-benzothiazol-2-ylamino)-H-benzoimidazole-5-carboxylic acid methyl amide; 1-Methyl-2-(6-trifluoromethoxy-benzothiazol-2-ylamino)-1H-benzoimidazole-5-carboxylic acid methyl ester; 1-Methyl-2-(6-trifluoromethoxy-benzothiazol-2-ylamino)-1H-benzoimidazole-5-carboxylic acid; 1-Methyl-2-(6-trifluoromethoxy-benzothiazol-2-ylamino)-1H-benzoimidazole-5-carboxylic acid (2-ethoxy-ethyl)-amide; 1-Methyl-2-(6-trifluoromethoxy-benzothiazol-2-ylamino)-1H-benzoimidazole-5-carboxylic acid cyclopropylmethyl-amide; 1-Methyl-2-(6-trifluoromethoxy-benzothiazol-2-ylamino)-1H-benzoimidazole-5-carboxylic acid ethylamide; [1-Methyl-2-(6-trifluoromethoxy-benzothiazol-2-ylamino)-1H-benzoimidazol-5-yl]-pyrrolidin-1-yl-methanone; 1-Methyl-2-(6-trifluoromethoxy-benzothiazol-2-ylamino)-1H-benzoimidazole-5-carboxylic acid (2-methoxy-ethyl)-amide; 1-Methyl-2-(6-trifluoromethoxy-benzothiazol-2-ylamino)-1H-benzoimidazole-5-carboxylic acid (2-fluoro-ethyl)-amide; 1-Methyl-2-(6-trifluoromethoxy-benzothiazol-2-ylamino)-1H-benzoimidazole-5-carboxylic acid (2-hydroxy-ethyl)-amide; 1-Methyl-2-(6-trifluoromethoxy-benzothiazol-2-ylamino)-1H-benzoimidazole-5-carboxylic acid (3-pyrazol-1-yl-propyl)-amide; 1-Methyl-2-(6-trifluoromethoxy-benzothiazol-2-ylamino)-1H-benzoimidazole-5-carboxylic acid propylamide; 1-Methyl-2-(6-trifluoromethoxy-benzothiazol-2-ylamino)-1H-benzoimidazole-5-carboxylic acid (3-hydroxy-propyl)-amide; 1-Methyl-2-(6-trifluoromethoxy-benzothiazol-2-ylamino)-1H-benzoimidazole-5-carboxylic acid (3-ethoxy-propyl)-amide; 1-Methyl-2-(6-trifluoromethoxy-benzothiazol-2-ylamino)-1H-benzoimidazole-5-carboxylic acid morpholin-4-ylamide; 1-Methyl-2-(6-trifluoromethoxy-benzothiazol-2-ylamino)-1H-benzoimidazole-5-carboxylic acid (2,2,2-trifluoro-ethyl)-amide; 1-Methyl-2-(6-trifluoromethoxy-benzothiazol-2-ylamino)-1H-benzoimidazole-5-carboxylic acid (tetrahydro-pyran-4-ylmethyl)-amide; 1-Methyl-2-(6-trifluoromethoxy-benzothiazol-2-ylamino)-1H-benzoimidazole-5-carboxylic acid (tetrahydro-furan-2-ylmethyl)-amide; 1-Methyl-2-(6-trifluoromethoxy-benzothiazol-2-ylamino)-1H-benzoimidazole-5-carboxylic acid (3-methoxy-propyl)-amide; 1-Methyl-2-(6-trifluoromethoxy-benzothiazol-2-ylamino)-1H-benzoimidazole-5-carboxylic acid (2-methoxy-1-methyl-ethyl)-amide; 1-Methyl-2-(6-trifluoromethoxy-benzothiazol-2-ylamino)-1H-benzoimidazole-5-carboxylic acid (2-hydroxy-propyl)-amide; 1-Methyl-2-(6-trifluoromethoxy-benzothiazol-2-ylamino)-1H-benzoimidazole-5-carboxylic acid (2-methoxy-2-methyl-propyl)-amide; 1-Methyl-2-(6-trifluoromethyl-benzothiazol-2-ylamino)-1H-benzoimidazole-5-carboxylic acid methylester; 1-Methyl-2-(6-trifluoromethyl-benzothiazol-2-ylamino)-1H-benzoimidazole-5-carboxylic acid; 1-Methyl-2-(6-trifluoromethyl-benzothiazol-2-ylamino)-1H-benzoimidazole-5-carboxylic acid (2-methoxy-ethyl)-amide; 1-Methyl-2-(6-trifluoromethyl-benzothiazol-2-ylamino)-1H-benzoimidazole-5-carboxylic acid ethylamide; 1-Methyl-2-(6-trifluoromethyl-benzothiazol-2-ylamino)-1H-benzoimidazole-5-carboxylic acid (2-hydroxy-ethyl)-amide; 2-(6-Chloro-benzothiazol-2-ylamino)-1-methyl-1H-benzoimidazole-5-carboxylic acid methyl ester; 2-(6-Chloro-benzothiazol-2-ylamino)-1-methyl-1H-benzoimidazole-5-carboxylic acid; 2-(6-Chloro-benzothiazol-2-ylamino)-1-methyl-1H-benzoimidazole-5-carboxylic acid (2-hydroxy-ethyl)-amide; 2-(6-Chloro-benzothiazol-2-ylamino)-1-methyl-1H-benzoimidazole-5-carboxylic acid (2-methoxy-ethyl)-amide; 2-(6-Chloro-benzothiazol-2-ylamino)-1-methyl-1H-benzoimidazole-5-carboxylic acid ethylamide; 2-(5,6-Difluoro-benzothiazol-2-ylamino)-1-methyl-1H-benzoimidazole-5-carboxylic acid methyl ester; 2-(5,6-Difluoro-benzothiazol-2-ylamino)-1-methyl-1H-benzoimidazole-5-carboxylic acid; 2-(5,6-Difluoro-benzothiazol-2-ylamino)-1-methyl-1H-benzoimidazole-5-carboxylic acid ethylamide; 2-(5,6-Difluoro-benzothiazol-2-ylamino)-2-(6-Chloro-benzothiazol-2-ylamino)-1-methyl-1H-benzoimidazole-5-carboxylic acid ethylamide, 2-(5,6-Difluoro-benzothiazol-2-ylamino)-1-methyl-1H-benzoimidazole-5-carboxylic acid methyl ester; 2-(5,6-Difluoro-benzothiazol-2-ylamino)-1-methyl-1H-benzoimidazole-5-carboxylic acid; 2-(5,6-Difluoro-benzothiazol-2-ylamino)-1-methyl-1H-benzoimidazole-5-carboxylic acid ethylamide; 2-(5,6-Difluoro-benzothiazol-2-ylamino)-1-methyl-1H-benzoimidazole-5-carboxylic acid (2-hydroxy-ethyl)-amide; 2-(5,6-Difluoro-benzothiazol-2-ylamino)-1-methyl-1H-benzoimidazole-5-carboxylic acid (2-methoxy-ethyl)-amide; 3-Methyl-2-(6-trifluoromethoxy-benzothiazol-2-ylamino)-3H-benzoimidazole-5-carboxylic acid methylamide; 6-Fluoro-1-methyl-2-(6-trifluoromethoxybenzothiazol-2-ylamino)-1H-benzoimidazole-5-carboxylic acid (2-methoxy-ethyl)-amide; 6-Fluoro-1-methyl-2-(6-trifluoromethoxy-benzothiazol-2-ylamino)-1H-benzoimidazole-5-carboxylic acid methyl ester; 6-Fluoro-1-methyl-2-(6-trifluoromethoxy-benzothiazol-2-ylamino)-1H-benzoimidazole-5-carboxylic acid; 6-Fluoro-1-methyl-2-(6-trifluoromethoxy-benzothiazol-2-ylamino)-1H-benzoimidazole-5-carboxylic acid ethylamide; 1-Methyl-2-(6-trifluoromethoxy-benzothiazol-2-ylamino)-1H-benzoimidazole-5-carboxylic acid (2-morpholin-4-yl-ethyl)-amide; 1-Methyl-2-(6-trifluoromethoxy-benzothiazol-2-ylamino)-1H-benzoimidazole-5-carboxylic acid (2-trifluoromethoxy-ethyl)-amide; 1-Methyl-2-(6-trifluoromethoxy-benzothiazol-2-ylamino)-1H-benzoimidazole-5-carboxylic acid (2-hydroxy-2-methyl-propyl)-amide; 1-Methyl-2-(6-trifluoromethoxy-benzothiazol-2-ylamino)-1H-benzoimidazole-5-carboxylic acid [2-(2-hydroxy-ethoxy)-ethyl]-amide; 1-Methyl-2-(6-trifluoromethoxy-benzothiazol-2-ylamino)-1H-benzoimidazole-5-carboxylic acid [2-(2-fluoro-ethoxy)-ethyl]-amide; I-Methyl-2-(6-trifluoromethoxy-benzothiazol-2-ylamino)-1H-benzoimidazole-5-carboxylic acid (furan-2-ylmethyl)-amide; 1-Methyl-2-(6-trifluoromethoxy-benzothiazol-2-ylamino)-1H-benzoimidazole-5-carboxylic acid ([1,4]dioxan-2-ylmethyl)-amide; 1-Methyl-2-(6-trifluoromethoxy-benzothiazol-2-ylamino)-1H-benzoimidazole-5-carboxylic acid ((S)-2-hydroxy-propyl)-amide; 1-Methyl-2-(6-trifluoromethoxy-benzothiazol-2-ylamino)-1H-benzoimidazole-5-carboxylic acid ((R)-2-hydroxy-propyl)-amide; 1-Methyl-2-(6-trifluoromethoxy-benzothiazol-2-ylamino)-1H-benzoimidazole-5-carboxylic acid (trans-4-hydroxy-cyclohexyl)-amide; 1-Methyl-2-(6-trifluoromethoxy-benzothiazol-2-ylamino)-1H-benzoimidazole-5-carboxylic acid [2-(tetrahydro-furan-2-ylmethoxy)-ethyl]-amide; 1-Methyl-2-(6-trifluoromethoxy-benzothiazol-2-ylamino)-1H-benzoimidazole-5-carboxylic acid (2-ethoxy-propyl)-amide; 2-({[1-Methyl-2-(6-trifluoromethoxy-benzothiazol-2-ylamino)-1H-benzoimidazole-5-carbonyl]-amino}-methyl)-morpholine-4-carboxylic acid tert-butyl ester; 1-Methyl-2-(6-trifluoromethoxy-benzothiazol-2-ylamino)-1H-benzoimidazole-5-carboxylic acid (morpholin-2-ylmethyl)-amide hydrochloride; 6-Fluoro-1-methyl-2-(6-trifluoromethoxy-benzothiazol-2-ylamino)-1H-benzoimidazole-5-carboxylic acid (2-ethoxy-ethyl)-amide; 6-Fluoro-1-methyl-2-(6-trifluoromethoxy-benzothiazol-2-ylamino)-1H-benzoimidazole-5-carboxylic acid dimethylcarbamoylmethyl-amide; 6-Fluoro-1-methyl-2-(6-trifluoromethoxy-benzothiazol-2-ylamino)-1H-benzoimidazole-5-carboxylic acid (2-morpholin-4-yl-ethyl)-amide; 6-Fluoro-1-methyl-2-(6-trifluoromethoxy-benzothiazol-2-ylamino)-1H-benzoimidazole-5-carboxylic acid (2-hydroxy-propyl)-amide; 6-Methoxy-1-methyl-2-(6-trifluoromethoxy-benzothiazol-2-ylamino)-1H-benzoimidazole-5-carboxylic acid methyl ester; 6-Methoxy-1-methyl-2-(6-trifluoromethoxy-benzothiazol-2-ylamino)-1H-benzoimidazole-5-carboxylic acid; 6-Methoxy-1-methyl-2-(6-trifluoromethoxy-benzothiazol-2-ylamino)-1H-benzoimidazole-5-carboxylic acid dimethylcarbamoylmethyl-amide; 6-Methoxy-1-methyl-2-(6-trifluoromethoxy-benzothiazol-2-ylamino)-1H-benzoimidazole-5-carboxylic acid ethylamide; 6-Methoxy-1-methyl-2-(6-trifluoromethoxy-benzothiazol-2-ylamino)-1H-benzoimidazole-5-carboxylic acid (2-ethoxy-ethyl)-amide; 6-Methoxy-1-methyl-2-(6-trifluoromethoxy-benzothiazol-2-ylamino)-1H-benzoimidazole-5-carboxylic acid (2-morpholin-4-yl-ethyl)-amide; 6-Methoxy-1-methyl-2-(6-trifluoromethoxy-benzothiazol-2-ylamino)-1H-benzoimidazole-5-carboxylic acid (2-methoxy-ethyl)-amide; 6-Methoxy-1-methyl-2-(6-trifluoromethoxy-benzothiazol-2-ylamino)-1H-benzoimidazole-5-carboxylic acid (2-hydroxy-propyl)-amide; 6-Diethylamino-1-methyl-2-(6-trifluoromethoxy-benzothiazol-2-ylamino)-1H-benzoimidazole-5-carboxylic acid methyl ester; 6-Diethylamino-1-methyl-2-(6-trifluoromethoxy-benzothiazol-2-ylamino)-1H-benzoimidazole-5-carboxylic acid; 3-Methyl-2-(6-trifluoromethoxy-benzothiazol-2-ylamino)-3H-imidazo[4,5-b]pyridine-6-carboxylic acid ethyl ester; 3-Methyl-2-(6-trifluoromethoxy-benzothiazol-2-ylamino)-3H-imidazo[4,5-b]pyridine-6-carboxylic acid; 3-Methyl-2-(6-trifluoromethoxy-benzothiazol-2-ylamino)-3H-imidazo[4,5-b]pyridine-6-carboxylic acid (2-methoxy-ethyl)-amide; 3-Methyl-2-(6-trifluoromethoxy-benzothiazol-2-ylamino)-3H-imidazo[4,5-b]pyridine-6-carboxylic acid dimethylcarbamoylmethyl-amide; 3-Methyl-2-(6-trifluoromethoxy-benzothiazol-2-ylamino)-3H-imidazo[4,5-b]pyridine-6-carboxylic acid (2-ethoxy-ethyl)-amide; 3-Methyl-2-(6-trifluoromethoxy-benzothiazol-2-ylamino)-3H-imidazo[4,5-b]pyridine-6-carboxylic acid ethylamide; 3-Methyl-2-(6-trifluoromethoxy-benzothiazol-2-ylamino)-3H-imidazo[4,5-b]pyridine-6-carboxylic acid (2-morpholin-4-yl-ethyl)-amide; 3-Methyl-2-(6-trifluoromethoxy-benzothiazol-2-ylamino)-3H-imidazo[4,5-b]pyridine-6-carboxylic acid (2-hydroxy-propyl)-amide; {[1-Methyl-2-(6-trifluoromethoxy-benzothiazol-2-ylamino)-1H-benzoimidazole-5-carbonyl]-amino}-acetic acid methyl ester; -Methyl-2-(6-trifluoromethoxy-benzothiazol-2-ylamino)-1H-benzoimidazole-5-carboxylic acid dimethylcarbamoylmethyl-amide; 1-Methyl-2-(6-trifluoromethoxy-benzothiazol-2-ylamino)-1H-benzoimidazole-5-carboxylic acid ((S)-1-ethylcarbamoyl-ethyl)-amide; 1-Methyl-2-(6-trifluoromethoxy-benzothiazol-2-ylamino)-1H-benzoimidazole-5-carboxylic acid (2-dimethylamino-ethyl)-amide; {[1-Methyl-2-(6-trifluoromethoxy-benzothiazol-2-ylamino)-1H-benzoimidazole-5-carbonyl]-amino}-acetic acid; 1-Methyl-2-(6-trifluoromethyl-benzothiazol-2-ylamino)-1H-benzoimidazole-5-carboxylic acid methylamide; I-Methyl-2-(6-trifluoromethyl-benzothiazol-2-ylamino)-1H-benzoimidazole-5-carboxylic acid (2-ethoxy-ethyl)-amide; 2-(5,6-Difluoro-benzothiazol-2-ylamino)-1-methyl-1H-benzoimidazole-5-carboxylic acid methylamide; 2-(5,6-Difluoro-benzothiazol-2-ylamino)-1-methyl-1H-benzoimidazole-5-carboxylic acid (2-ethoxy-ethyl)-amide; 2-(6-Chloro-benzothiazol-2-ylamino)-1-methyl-1H-benzoimidazole-5-carboxylic acid methylamide; 2-(6-Chloro-benzothiazol-2-ylamino)-1-methyl-1H-benzoimidazole-5-carboxylic acid (2-ethoxy-ethyl)-amide; 1-Methyl-2-(6-trifluoromethoxy-benzothiazol-2-ylamino)-1H-benzoimidazole-5-carboxylic acid (1-methanesulfonyl-piperidin-4-yl)-amide; {[1-Methyl-2-(6-trifluoromethoxy-benzothiazol-2-ylamino)-1H-benzoimidazole-5-carbonyl]-amino}-acetic acid tert-butyl ester; 4-{[1-Methyl-2-(6-trifluoromethoxy-benzothiazol-2-ylamino)-1H-benzoimidazole-5-carbonyl]-amino}-piperidine-1-carboxylic acid tert-butyl ester; 1-Methyl-2-(6-trifluoromethoxy-benzothiazol-2-ylamino)-1H-benzoimidazole-5-carboxylic acid piperidin-4-ylamide hydrochloride; 3-{[1-Methyl-2-(6-trifluoromethoxy-benzothiazol-2-ylamino)-1H-benzoimidazole-5-carbonyl]-amino}-piperidine-1-carboxylic acid tert-butyl ester; 1-Methyl-2-(6-trifluoromethoxy-benzothiazol-2-ylamino)-1H-benzoimidazole-5-carboxylic acid piperidin-3-ylamide hydrochloride; 1-Methyl-2-(6-trifluoromethoxy-benzothiazol-2-ylamino)-1H-benzoimidazole-5-carboxylic acid (thiazol-2-ylmethyl)-amide; 3-{[1-Methyl-2-(6-trifluoromethoxy-benzothiazol-2-ylamino)-1H-benzoimidazole-5- carbonyl]-amino}-propionic acid methyl ester; 3-{[2-(6-Trifluoromethoxy-benzothiazol-2-ylamino)-1-methyl-1H-benzimidazole-5-carbonyl]-amino}-propionic acid; 1-Methyl-2-(5-trifluoromethoxy-benzothiazol-2-ylamino)-1H-benzoimidazole-5-carboxylic acid methyl ester; 1-Methyl-2-(6-trifluoromethoxy-benzothiazol-2-ylamino)-1H-benzoimidazole-5-carboxylic acid (2-acetylamino-ethyl)-amide; 1-Methyl-2-(6-trifluoromethoxy-benzothiazol-2-ylamino)-1H-benzoimidazole-5-carboxylic acid (2-methylsulfanyl-ethyl)-amide; 1-Methyl-2-(6-trifluoromethoxy-benzothiazol-2-ylamino)-1H-benzoimidazole-5-carboxylic acid (2-methanesulfonyl-ethyl)-amide; (2-{[1-Methyl-2-(6-trifluoromethoxy-benzothiazol-2-ylamino)-1H-benzoimidazole-5-carbonyl]-amino}-ethyl)-carbamic acid tert-butyl ester; 1-Methyl-2-(6-trifluoromethoxy-benzothiazol-2-ylamino)-1H-benzoimidazole-5-carboxylic acid (2-amino-ethyl)-amide hydrochloride; 1-Methyl-2-(6-trifluoromethoxy-benzothiazol-2-ylamino)-1H-benzoimidazole-5-carboxylic acid (2-methylamino-ethyl)-amide; 1-Methyl-2-(6-trifluoromethoxy-benzothiazol-2-ylamino)-1H-benzoimidazole-5-carboxylic acid trimethylhydrazide; 1-Methyl-2-(6-trifluoromethoxy-benzothiazol-2-ylamino)-1H-benzoimidazole-5-carboxylic acid (2-ethylsulfanyl-ethyl)-amide; 1-Methyl-2-(6-trifluoromethoxy-benzothiazol-2-ylamino)-1H-benzoimidazole-5-carboxylic acid (3-methylsulfanyl-propyl)-amide; 1-Methyl-2-(6-trifluoromethoxy-benzothiazol-2-ylamino)-1H-benzoimidazole-5-carboxylic acid (2-ethanesulfonyl-ethyl)-amide; 1-Methyl-2-(6-trifluoromethoxy-benzothiazol-2-ylamino)-1H-benzimidazole-5-carboxylic acid (3-methanesulfonyl-propyl)-amide; 2-(5-Fluoro-benzothiazol-2-ylamino)-1-methyl-1H-benzoimidazole-5-carboxylic acid methyl ester; 2-(6-Fluoro-benzothiazol-2-ylamino)-1-methyl-1H-benzoimidazole-5-carboxylic acid methyl ester; 2-(6-Methanesulfonyl-benzothiazol-2-ylamino)-1-methyl-1H-benzoimidazole-5-carboxylic acid methyl ester; I-Methyl-2-(6-methyl-benzothiazol-2-ylamino)-H-benzoimidazole-5-carboxylic acid methyl ester; 1-Methyl-2-(5-trifluoromethoxy-benzothiazol-2-ylamino)-1H-benzimidazole-5-carboxylic acid methylamide; 1-Methyl-2-(5-trifluoromethoxy-benzothiazol-2-ylamino)-1H-benzimidazole-5-carboxylic acid (2-methoxy-ethyl)-amide; 2-(5-Fluoro-benzothiazol-2-ylamino)-1-methyl-1H-benzimidazole-5-carboxylic acid; 2-(6-Fluoro-benzothiazol-2-ylamino)-1-methyl-1H-benzimidazole-5-carboxylic acid; 2-(6-Methanesulfonyl-benzothiazol-2-ylamino)-1-methyl-1H-benzimidazole-5-carboxylic acid; 1-Methyl-2-(6-methyl-benzothiazol-2-ylamino)-1H-benzoimidazole-5-carboxylic acid; 1-Methyl-2-(6-trifluoromethoxy-benzothiazol-2-ylamino)-1H-benzimidazole-5-carboxylic acid (1,1-dioxo-tetrahydro-1^-thiophen-3-yl)-amide; 2-(5-Fluoro-benzothiazol-2-ylamino)-1-methyl-1H-benzimidazole-5-carboxylic acid methylamide; 2-(5-Fluoro-benzothiazol-2-ylamino)-1-methyl-1H-benzimidazole-5-carboxylic acid (2-methoxy-ethyl)-amide; 2-(6-Fluoro-benzothiazol-2-ylamino)-1-methyl-1H-benzimidazole-5-carboxylic acid methylamide; 2-(6-Fluoro-benzothiazol-2-ylamino)-1-methyl-1H-benzimidazole-5-carboxylic acid (2-methoxy-ethyl)-amide; 2-(6-Methanesulfonyl-benzothiazol-2-ylamino)-1-methyl-1H-benzimidazole-5-carboxylic acid methylamide; 2-(6-Methanesulfonyl-benzothiazol-2-ylamino)-1-methyl-1H-benzimidazole-5-carboxylic acid (2-methoxy-ethyl)-amide; 2-(6-Methyl-benzothiazol-2-ylamino)-1-methyl-1H-benzimidazole-5-carboxylic acid methylamide; 2-(6-Methyl-benzothiazol-2-ylamino)-1-methyl-1H-benzimidazole-5-carboxylic acid (2-methoxy-ethyl)-amide; 2-(6-Methanesulfonyl-benzothiazol-2-ylamino)-1-methyl-1H-benzimidazole-5-carboxylic acid (2-methylsulfanyl-ethyl)-amide; 2-(6-Methanesulfonyl-benzothiazol-2-ylamino)-1-methyl-1H-benzimidazole-5-carboxylic acid (2-methylsulfonyl-ethyl)-amide; I-Methyl-2-(6-trifluoromethylsulfanyl-benzothiazol-2-ylamino)-H-benzoimidazole-5-carboxylic acid methyl ester; 2-(6-Chloro-benzothiazol-2-ylamino)-1-methyl-1H-benzimidazole-5-carboxylic acid dimethylcarbamoylmethyl-amide; 1-Methyl-2-(6-trifluoromethyl-benzothiazol-2-ylamino)-1H-benzimidazole-5-carboxylic acid dimethylcarbamoylmethyl-amide; 1-Methyl-2-(6-trifluoromethoxy-benzothiazol-2-ylamino)-1H-benzimidazole-5-carboxylic acid (2-dimethylcarbamoyl-ethyl)-amide; 3-{[1-Methyl-2-(6-trifluoromethoxy-benzothiazol-2-ylamino)-1H-benzimidazole-5-carbonyl]-amino}-propionic acid tert-butyl ester; 1-Methyl-2-(6-trifluoromethoxy-benzothiazol-2-ylamino)-1H-benzimidazole-5-carboxylic acid [2-(4-methyl-piperazin-1-yl)-2-oxo-ethyl]-amide; 1-Methyl-2-(6-trifluoromethoxy-benzothiazol-2-ylamino)-1H-benzimidazole-5-carboxylic acid (2-morpholin-4-yl-2-oxo-ethyl)-amide; 1-Methyl-2-(6-trifluoromethoxy-benzothiazol-2-ylamino)-1H-benzimidazole-5-carboxylic acid methylcarbamoylmethyl-amide; 1-Methyl-2-(6-trifluoromethoxy-benzothiazol-2-ylamino)-1H-benzimidazole-5-carboxylic acid diethylcarbamoylmethyl-amide; 1-Methyl-2-(6-trifluoromethoxy-benzothiazol-2-ylamino)-1H-benzimidazole-5-carboxylic acid (2-oxo-2-pyrrolidin-1-yl-ethyl)-amide; 4-(2-{[1-Methyl-2-(6-trifluoromethoxy-benzothiazol-2-ylamino)-1H-benzimidazole-5-carbonyl]-amino}-acetyl)-piperazine-1-carboxylic acid tert-butyl ester; (S)-2-{[1-Methyl-2-(6-trifluoromethoxy-benzothiazol-2-ylamino)-1H-benzoimidazole-5-carbonyl]-amino}-propionic acid methyl ester; 1-{[1-Methyl-2-(6-trifluoromethoxy-benzothiazol-2-ylamino)-1H-benzimidazole-5-carbonyl]-amino}-eye lopropanecarboxylic acid ethyl ester; 2-Methyl-2-{[1-methyl-2-(6-trifluoromethoxy-benzothiazol-2-ylamino)-1H-benzimidazole-5-carbonyl]-amino}-propionic acid methyl ester; (S)-2-([1-Methyl-2-(6-trifluoromethoxy-benzothiazol-2-ylamino)-1H-benzoimidazole-5-carbonyl]-amino)-propionic acid; 1-{[1-Methyl-2-(6-trifluoromethoxy-benzothiazol-2-ylamino)-1H-benzimidazole-5-carbonyl]-amino}-cyclopropanecarboxylic acid; 2-Methyl-2-{[1-methyl-2-(6-trifluoromethoxy-benzothiazol-2-ylamino)-1H-benzimidazole-5-carbonyl]-amino}-propionic acid; 1-Methyl-2-(6-trifluoromethoxy-benzothiazol-2-ylamino)-1H-benzoimidazole-5-carboxylic acid ((S)-1-dimethylcarbamoyl-ethyl)-amide; 1-Methyl-2-(6-trifluoromethoxy-benzothiazol-2-ylamino)-1H-benzimidazole-5-carboxylic acid (1-dimethylcarbamoyl-cyclopropyl)-amide; 1-Methyl-2-(6-trifluoromethoxy-benzothiazol-2-ylamino)-1H-benzimidazole-5-carboxylic acid (1-dimethylcarbamoyl-1-methyl-ethyl)-amide; 1-Methyl-2-(6-trifluoromethoxy-benzothiazol-2-ylamino)-1H-benzimidazole-5-carboxylic acid (2-oxo-2-piperazin-1-yl-ethyl)-amide hydrochloride; 1-Ethyl-2-(6-trifluoromethoxy-benzothiazol-2-ylamino)-1H-benzoimidazole-5-carboxylic acid methyl ester; 1-Ethyl-2-(6-trifluoromethoxy-benzothiazol-2-ylamino)-1H-benzoimidazole-5-carboxylic acid; 1-Ethyl-2-(6-trifluoromethoxy-benzothiazol-2-ylamino)-1H-benzoimidazole-5-carboxylic acid methylamide; 1-Ethyl-2-(6-trifluoromethoxy-benzothiazol-2-ylamino)-1H-benzoimidazole-5-carboxylic acid ethylamide; 1-Ethyl-2-(6-trifluoromethoxy-benzothiazol-2-ylamino)-1H-benzoimidazole-5-carboxylic acid (2-ethoxy-ethyl)-amide; 1-Isopropyl-2-(6-trifluoromethoxy-benzothiazol-2-ylamino)-1H benzoimidazole-5-carboxylic acid methyl ester; 1-Isopropyl-2-(6-trifluoromethoxy-benzothiazol-2-ylamino)-1H-benzoimidazole-5-carboxylic acid; 1-Isopropyl-2-(6-trifluoromethoxy-benzothiazol-2-ylamino)-1H-benzoimidazole-5-carboxylic acid methylamide; 1-Isopropyl-2-(6-trifluoromethoxy-benzothiazol-2-ylamino)-1H-benzoimidazole-5-carboxylic acid ethylamide; 1-Isobutyl-2-(6-trifluoromethoxy-benzothiazol-2-ylamino)-1H-benzoimidazole-5-carboxylic acid methyl ester; 1-Isobutyl-2-(6-trifluoromethoxy-benzothiazol-2-ylamino)-1H-benzoimidazole-5-carboxylic acid; 1-Isobutyl-2-(6-trifluoromethoxy-benzothiazol-2-ylamino)-1H-benzoimidazole-5-carboxylic acid methylamide; 1-Isobutyl-2-(6-trifluoromethoxy-benzothiazol-2-ylamino)-1H-benzoimidazole-5-carboxylic acid ethylamide; 1-(2-Methoxy-ethyl)-2-(6-trifluoromethoxy-benzothiazol-2-ylamino)-1H-benzoimidazole-5-carboxylic acid; 1-(2-Methoxy-ethyl)-2-(6-trifluoromethoxy-benzothiazol-2-ylamino)-1H-benzoimidazole-5-carboxylic acid methylamide; 1-(2-Methoxy-ethyl)-2-(6-trifluoromethoxy-benzothiazol-2-ylamino)-1H-benzoimidazole-5-carboxylic acid (2-methoxy-ethyl)-amide; 1-(2-Methoxy-ethyl)-2-(6-trifluoromethoxy-benzothiazol-2-ylamino)-1H-benzoimidazole-5-carboxylic acid (2-ethoxy-ethyl)-amide; 1-(2-Fluoro-ethyl)-2-(6-trifluoromethoxy-benzothiazol-2-ylamino)-1H-benzoimidazole-5-carboxylic acid methylamide; 1-(2-Fluoro-ethyl)-2-(6-trifluoromethoxy-benzothiazol-2-ylamino)-1H-benzoimidazole-5-carboxylic acid (2-methoxy-ethyl)-amide; 1-(2-Fluoro-ethyl)-2-(6-trifluoromethoxy-benzothiazol-2-ylamino)-1H-benzoimidazole-5-carboxylic acid (2-ethoxy-ethyl)-amide; 1-(2-Amino-ethyl)-2-(6-trifluoromethoxy-benzothiazol-2-ylamino)-1H-benzoimidazole-5-carboxylic acid methylamide hydrochloride; 2-(6-Chloro-benzothiazol-2-ylamino)-1-ethyl-1H-benzoimidazole-5-carboxylic acid methylamide; 2-(6-Chloro-benzothiazol-2-ylamino)-1-ethyl-1H-benzoimidazole-5-carboxylic acid ethylamide; 2-(6-Chloro-benzothiazol-2-ylamino)-1-ethyl-1H-benzoimidazole-5-carboxylic acid (2-fluoro-ethyl)-amide; 2-(6-Chloro-benzothiazol-2-ylamino)-1-ethyl-1H-benzoimidazole-5-carboxylic acid (2-methoxy-ethyl)-amide; 2-(6-Chloro-benzothiazol-2-ylamino)-1-ethyl-1H-benzoimidazole-5-carboxylic acid (2-methoxy-2-methyl-propyl)-amide; 2-(6-Chloro-benzothiazol-2-ylamino)-1-ethyl-1H-benzoimidazole-5-carboxylic acid (2-ethoxy-ethyl)-amide; 1-Ethyl-2-(6-trifluoromethyl-benzothiazol-2-ylamino)-1H-benzoimidazole-5-carboxylic acid methylamide; 1-Ethyl-2-(6-trifluoromethyl-benzothiazol-2-ylamino)-H-benzoimidazole-5-carboxylic acid ethylamide; 1-Ethyl-2-(6-trifluoromethyl-benzothiazol-2-ylamino)-1H-benzoimidazole-5-carboxylic acid (2-methoxy-ethyl)-amide; 1-Ethyl-2-(6-trifluoromethyl-benzothiazol-2-ylamino)-1H-benzoimidazole-5-carboxylic acid (2-ethoxy-ethyl)-amide; 1-Ethyl-2-(6-trifluoromethyl-benzothiazol-2-ylamino)-1H-benzoimidazole-5-carboxylic acid (2-methoxy-2-methyl-propyl)-amide; 1-Ethyl-2-(6-trifluoromethyl-benzothiazol-2-ylamino)-1H-benzoimidazole-5-carboxylic acid (2-methylsulfanyl-ethyl)-amide; 1-Ethyl-2-(6-trifluoromethoxy-benzothiazol-2-ylamino)-H-benzoimidazole-5-carboxylic acid dimethylcarbamoylmethyl-amide; 1-Ethyl-2-(6-trifluoromethyl-benzothiazol-2-ylamino)-1H-benzoimidazole-5-carboxylic acid dimethylcarbamoylmethyl-amide; 1-(2-Methoxy-ethyl)-2-(6-trifluoromethoxy-benzothiazol-2-ylamino)-1H-benzoimidazole-5-carboxylic acid dimethylcarbamoylmethyl-amide; 1-(2-Methoxy-ethyl)-2-(6-trifluoromethoxy-benzothiazol-2-ylamino)-1H-benzoimidazole-5-carboxylic acid [2-(4-methyl-piperazin-1-yl)-2-oxo-ethyl]-amide; 1-Ethyl-2-(6-trifluoromethoxy-benzothiazol-2-ylamino)-1H-benzoimidazole-5-carboxylic acid [2-(4-methyl-piperazin-1-yl)-2-oxo-ethyl]-amide; 1-Ethyl-2-[6-(pyridin-3-yloxy)-benzothiazol-2-ylamino]-H-benzoimidazole-5-carboxylic acid (2-methoxy-ethyl)-amide; 1-Methyl-2-(6-trifluoromethoxy-benzothiazol-2-ylamino)-1H-benzoimidazole-5-carboxylic acid [2-(4-hydroxy-piperidin-1-yl)-ethyl]-amide; 1-Methyl-2-(6-trifluoromethoxy-benzothiazol-2-ylamino)-1H-benzoimidazole-5-carboxylic acid [2-(3-hydroxy-piperidin-1-yl)-ethyl]-amide; 1-Methyl-2-(6-trifluoromethoxy-benzothiazol-2-ylamino)-1H-benzoimidazole-5-carbonitrile; 1-Methyl-2-(6-trifluoromethoxy-benzothiazol-2-ylamino)-1H-benzoimidazole-6-carbonitrile; [5-(1H-Imidazol-2-yl)-1-methyl-1H-benzimidazol-2-yl]-(6-trifluoromethoxy-benzothiazol-2-yl)-amine; [1-Methyl-6-(1H-1,2,4-triazol-3-yl)-1H-benzimidazol-2-yl]-(6-trifluoromethoxy-benzothiazol-2-yl)-amine; [1-Methyl-6-(5-methyl-1H-1,2,4-triazol-3-yl)-1H-benzimidazol-2-yl]-(5-trifluoromethoxy-benzothiazol-2-yl)-amine; (1-Ethyl-5-trifluoromethanesulfonyl-1H-benzoimidazol-2-yl)-(6-trifluoromethoxy-benzothiazol-2-yl)-amine; 1-[1-Methyl-2-(6-trifluoromethoxy-benzothiazol-2-ylamino)-1H-benzoimidazol-5-yl]-ethanone; (5-Methanesulfonyl-1-methyl-1H-benzoimidazol-2-yl)-(6-trifluoromethoxy-benzothiazol-2-yl)-amine; 2-[1-Methyl-2-(6-trifluoromethoxy-benzothiazol-2-ylamino)-1H-benzoimidazol-6-yl]-acetamide; 2-(6-Chloro-benzothiazol-2-ylamino)-1-methyl-1H-benzoimidazole-5-carboxylic acid ((R)-2-hydroxy-propyl)-amide; 2-(6-Chloro-benzothiazol-2-ylamino)-1-methyl-1H-benzoimidazole-5-carboxylic acid ((S)-2-hydroxy-propyl)-amide; 1-Methyl-2-(6-trifluoromethyl-benzothiazol-2-ylamino)-1H-benzoimidazole-5-carboxylic acid ((R)-2-hydroxy-propyl)-amide; 1-Methyl-2-(6-trifluoromethyl-benzothiazol-2-ylamino)-1H-benzoimidazole-5-carboxylic acid ((S)-2-hydroxy-propyl)-amide; 2-(6-Chloro-benzothiazol-2-ylamino)-1-methyl-1H-benzoimidazole-5-carboxylic acid (2-methoxy-2-methyl-propyl)-amide; 1-Methyl-2-(6-trifluoromethyl-benzothiazol-2-ylamino)-1H-benzoimidazole-5-carboxylic acid (2-methoxy-2-methyl-propyl)-amide; 2-(6-Chloro-benzothiazol-2-ylamino)-1-methyl-1H-benzoimidazole-5-carboxylic acid (2-fluoro-ethyl)-amide; 1-Methyl-2-(6-trifluoromethyl-benzothiazol-2-ylamino)-1H-benzoimidazole-5-carboxylic acid (2-fluoro-ethyl)-amide; 1-Methyl-2-(6-trifluoromethoxy-benzothiazol-2-ylamino)-1H-benzoimidazole-5-carboxylic acid cyanomethyl-amide; 1-Methyl-2-(6-trifluoromethoxy-benzothiazol-2-ylamino)-1H-benzoimidazole-5-carboxylic acid (2-cyano-ethyl)-amide; 2-(6-Chloro-benzothiazol-2-ylamino)-1-methyl-1H-benzoimidazole-5-carboxylic acid (2-cyano-ethyl)-amide; 2-(6-Chloro-benzothiazol-2-ylamino)-1-methyl-1H-benzoimidazole-5-carboxylic acid (3-hydroxy-propyl)-amide; 2-(6-Chloro-benzothiazol-2-ylamino)-1-methyl-1H-benzoimidazole-5-carboxylic acid (3-hydroxy-butyl)-amide; 1-Methyl-2-(6-trifluoromethyl-benzothiazol-2-ylamino)-1H-benzoimidazole-5-carboxylic acid (3-hydroxy-butyl)-amide; 1-Methyl-2-(6-trifluoromethoxy-benzothiazol-2-ylamino)-1H-benzoimidazole-5-carboxylic acid (3-hydroxy-2,2-dimethyl-propyl)-amide; 2-(6-Chloro-benzothiazol-2-ylamino)-1-methyl-1H-benzoimidazole-5-carboxylic acid (3-hydroxy-2,2-dimethyl-propyl)-amide; 1-Methyl-2-(6-trifluoromethoxy-benzothiazol-2-ylamino)-1H-benzoimidazole-5-carboxylic acid (4-hydroxy-butyl)-amide; 2-(6-Chloro-1H-benzoimidazol-2-ylamino)-1-methyl-1H-benzoimidazole-5-carboxylic acid (4-hydroxy-butyl)-amide; 1-Methyl-2-(6-trifluoromethyl-benzothiazol- 2-ylamino)-1H-benzoimidazole-5-carboxylic acid (4-hydroxy-butyl)-amide; 6-Fluoro-1-methyl-2-(6-trifluoromethoxy-benzothiazol-2-ylamino)-1H-benzoimidazole-5-carboxylic acid (4-hydroxy-butyl)-amide; 1-Methyl-2-(6-trifluoromethoxy-benzothiazol-2-ylamino)-1H-benzoimidazole-5-carboxylic acid ((R)-4-hydroxy-3-methyl-butyl)-amide; 2-(6-Chloro-benzothiazol-2-ylamino)-1-methyl-1H-benzoimidazole-5-carboxylic acid ((R)-4-hydroxy-3-methyl-butyl)-amide; 2-(6-Chloro-benzothiazol-2-ylamino)-1-methyl-1H-benzoimidazole-5-carboxylic acid (trans-4-hydroxy-cyclohexyl)-amide; 1-Methyl-2-(6-trifluoromethoxy-benzothiazol-2-ylamino)-1H-benzoimidazole-5-carboxylic acid (5-hydroxy-pentyl)-amide; 2-(6-Chloro-benzothiazol-2-ylamino)-1-methyl-1H-benzoimidazole-5-carboxylic acid (5-hydroxy-pentyl)-amide; I-Methyl-2-(6-trifluoromethyl-benzothiazol-2-ylamino)-1H-benzoimidazole-5-carboxylic acid (5-hydroxy-pentyl)-amide; 1-Methyl-2-(6-trifluoromethoxy-benzothiazol-2-ylamino)-1H-benzoimidazole-5-carboxylic acid (5-hydroxy-4,4-dimethyl-pentyl)-amide; 1-Methyl-2-(6-trifluoromethoxy-benzothiazol-2-ylamino)-1H-benzoimidazole-5-carboxylic acid 4-hydroxy-benzyl-amide; 1-Methyl-2-(6-trifluoromethoxy-benzothiazol-2-ylamino)-1H-benzoimidazole-5-carboxylic acid 3-hydroxy-4-methoxy-benzylamide; 1-Methyl-2-(6-trifluoromethoxy-benzothiazol-2-ylamino)-1H-benzoimidazole-5-carboxylic acid (trans-4-hydroxy-cyclohexylmethyl)-amide; 2-(6-Chloro-benzothiazol-2-ylamino)-1-methyl-1H-benzoimidazole-5-carboxylic acid (trans-4-hydroxy-cyclohexylmethyl)-amide; 1-Methyl-2-(6-trifluoromethyl-benzothiazol-2-ylamino)-1H-benzoimidazole-5-carboxylic acid (trans-4-hydroxy-cyclohexylmethyl)-amide; 2-(6-Chloro-benzothiazol-2-ylamino)-1-methyl-1H-benzoimidazole-5-carboxylic acid [2-(2-hydroxy-ethoxy)-ethyl]-amide; 1-Methyl-2-(6-trifluoromethyl-benzothiazol-2-ylamino)-1H-benzoimidazole-5-carboxylic acid [2-(2-hydroxy-ethoxy)-ethyl]-amide; 6-Fluoro-1-methyl-2-(6-trifluoromethoxy-benzothiazol-2-ylamino)-1H-benzoimidazole-5-carboxylic acid [2-(2-hydroxy-ethoxy)-ethyl]-amide; 3-Methyl-2-(6-trifluoromethoxy-benzothiazol-2-ylamino)-3H-imidazo[4,5-b]pyridine-6-carboxylic acid [2-(2-hydroxy-ethoxy)-ethyl]-amide; 1-(2-Methylamino-ethyl)-2-(6-trifluoromethoxy-benzothiazol-2 ylamino)-1H-benzoimidazole-5-carboxylic acid[2-(2-hydroxy-ethoxy)-ethyl]-amide hydrochloride; 2-(6-Chloro-benzothiazol-2-ylamino)-1-(2-methylamino-ethyl)-1H-benzoimidazole-5-carboxylic acid [2-(2-hydroxy-ethoxy)-ethyl]-amide hydrochloride; 1-(2-Methoxy-ethyl)-2-(6-trifluoromethoxy-benzothiazol-2-ylamino)-1H-benzoimidazole-5-carboxylic acid [2-(2-hydroxy-ethoxy)-ethyl]-amide; 1-Methyl-2-(6-trifluoromethoxy-benzothiazol-2-ylamino)-1H-benzoimidazole-5-carboxylic acid [2-((R)-2-hydroxy-1-methyl-ethoxy)-ethyl]-amide; 2-(6-Chloro-benzothiazol-2-ylamino)-1-methyl-1H-benzoimidazole-5-carboxylic acid [2-((R)-2-hydroxy-1-methyl-ethoxy)-ethyl]-amide; 1-Methyl-2-(6-trifluoromethoxy-benzothiazol-2-ylamino)-1H-benzoimidazole-5-carboxylic acid [2-(2-hydroxy-propoxy)-ethyl]-amide; 1-Methyl-2-(6-trifluoromethoxy-benzothiazol-2-ylamino)-1H-benzoimidazole-5-carboxylic acid [2-(2-hydroxy-2-methyl-propoxy)-ethyl]-amide; 1-Methyl-2-(6-trifluoromethoxy-benzothiazol-2-ylamino)-1H-benzoimidazole-5-carboxylic acid [2-(3-hydroxy-propoxy)-ethyl]-amide; 1-Methyl-2-(6-trifluoromethoxy-benzothiazol-2-ylamino)-1H-benzoimidazole-5-carboxylic acid [2-(3-fluoro-propoxy)-ethyl]-amide; 2-(6-Chloro-benzothiazol-2-ylamino)-1-methyl-1H-benzoimidazole-5-carboxylic acid [2-(3-hydroxy-propoxy)-ethyl]-amide; 2-(6-Chloro-benzothiazol-2-ylamino)-1-methyl-1H-benzoimidazole-5-carboxylic acid [2-(3-fluoro-propoxy)-ethyl]-amide; 1-Methyl-2-(6-trifluoromethoxy-benzothiazol-2-ylamino)-1H-benzoimidazole-5-carboxylic acid [3-(2-hydroxy-ethoxy)-propyl]-amide; 1-Methyl-2-(6-trifluoromethoxy-benzothiazol-2-ylamino)-1H-benzoimidazole-5-carboxylic acid [2-(4-hydroxy-phenyl)-ethyl]-amide; 1-Methyl-2-(6-trifluoromethoxy-benzothiazol-2-ylamino)-1H-benzoimidazole-5-carboxylic acid [2-(3-hydroxy-phenyl)-ethyl]-amide; 1-Methyl-2-(6-trifluoromethoxy-benzothiazol-2-ylamino)-1H-benzoimidazole-5-carboxylic acid [2-(4-hydroxy-cyclohexyl)-ethyl]-amide; 1-Methyl-2-(6-trifluoromethoxy-benzothiazol-2-ylamino)-1H-benzoimidazole-5-carboxylic acid (trans-4-hydroxymethyl-cyclohexyl-methyl)-amide; 2-(6-Chloro-benzothiazol-2-ylamino)-1-methyl-1H-benzoimidazole-5-carboxylic acid (trans-4-hydroxymethyl-cyclohexylmethyl)-amide; 1-Methyl-2-(6-trifluoromethoxy-benzothiazol-2-ylamino)-1H-benzoimidazole-5-carboxylic acid (2-[2-(2-hydroxy-ethoxy)-ethoxy]-ethyl)-amide; 1-Methyl-2-(6-trifluoromethyl-benzothiazol-2-ylamino)-1H-benzoimidazole-5-carboxylic acid [2-(2-fluoro-ethoxy)-ethyl]-amide; 1-Methyl-2-(6-trifluoromethoxy-benzothiazol-2-ylamino)-1H-benzoimidazole-5-carboxylic acid [2-(2,2-difluoro-ethoxy)-ethyl]-amide; 2-(6-Chloro-benzothiazol-2-ylamino)-1-methyl-1H-benzoimidazole-5-carboxylic acid [2-(2,2-difluoro-ethoxy)-ethyl]-amide; 1-Methyl-2-(6-trifluoromethoxy-benzothiazol-2-ylamino)-1H-benzoimidazole-5-carboxylic acid [2-(2-methoxy-ethoxy)-ethyl]-amide; 2-(6-Chloro-benzothiazol-2-ylamino)-1-methyl-1H-benzoimidazole-5-carboxylic acid [2-(2-methoxy-ethoxy)-ethyl]-amide; 1-Methyl-2-(6-trifluoromethyl-benzothiazol-2-ylamino)-1H-benzoimidazole-5-carboxylic acid [2-(2-methoxy-ethoxy)-ethyl]-amide; 1-Methyl-2-(6-trifluoromethoxy-benzothiazol-2-ylamino)-1H-benzoimidazole-5-carboxylic acid [2-(tetrahydro-pyran-2-yl)-ethyl]-amide; 1-Methyl-2-(6-trifluoromethoxy-benzothiazol-2-ylamino)-1H-benzoimidazole-5-carboxylic acid [2-(tetrahydro-pyran-4-yl)-ethyl]-amide; 1-Methyl-2-(6-trifluoromethoxy-benzothiazol-2-ylamino)-1H-benzoimidazole-5-carboxylic acid [2-(2-cyano-ethoxy)-ethyl]-amide; 2-(6-Chloro-benzothiazol-2-ylamino)-1-methyl-1H-benzoimidazole-5-carboxylic acid [2-(2-cyano-ethoxy)-ethyl]-amide; 1-Methyl-2-(6-trifluoromethoxy-benzothiazol-2-ylamino)-1H-benzoimidazole-5-carboxylic acid (2-carbamoylmethoxy-ethyl)-amide; 1-Methyl-2-(6-trifluoromethoxy-benzothiazol-2-ylamino)-1H benzoimidazole-5-carboxylic acid [2-(2-amino-ethoxy)-ethyl]-amide; 2-(6-Chloro-benzothiazol-2-ylamino)-1-methyl-1H-benzoimidazole-5-carboxylic acid [2-(2-amino-ethoxy)-ethyl]-amide; 2-(4-Chloro-benzothiazol-2-ylamino)-1-methyl-1H benzoimidazole-5-carboxylic acid [2-(2-amino-ethoxy)-ethyl]-amide; 1-Methyl-2-(6-trifluoromethoxy-benzothiazol-2-ylamino)-1H-benzoimidazole-5-carboxylic acid [2-(2-methylamino-ethoxy)-ethyl]-amide hydrochloride; 2-(6-Chloro-benzothiazol-2-ylamino)-1-methyl-1H-benzoimidazole-5-carboxylic acid [2-(2-methylamino-ethoxy)-ethyl]-amide hydrochloride; 1-Methyl-2-(6-trifluoromethoxy-benzothiazol-2-ylamino)-1H-benzoimidazole-5-carboxylic acid [2-(2-dimethylamino-ethoxy)-ethyl]-amide; 2-(6-Chloro-benzothiazol-2-ylamino)-1-methyl-1H-benzoimidazole-5-carboxylic acid [2-(2-dimethylamino-ethoxy)-ethyl]-amide; 1-Methyl-2-(6-trifluoromethoxy-benzothiazol-2-ylamino)-1H-benzoimidazole-5-carboxylic acid [2-(2-acetylamino-ethoxy)-ethyl]-amide; 1-Methyl-2-(6-trifluoromethoxy-benzothiazol-2-ylamino)-1H-benzoimidazole-5-carboxylic acid [2-(2- methanesulfonylamino-ethoxy)-ethyl]-amide; 2-(6-Chloro-benzothiazol-2-ylamino)-1-methyl-1H-benzoimidazole-5-carboxylic acid (2-ethanesulfonyl-ethyl)-amide; 2-(6-Chloro-benzothiazol-2-ylamino)-1-methyl-1H-benzoimidazole-5-carboxylic acid [2-(2-hydroxy-ethanesulfonyl)-ethyl]-amide; 2-(6-Chloro-benzothiazol-2-ylamino)-1-methyl-1H-benzoimidazole-5-carboxylic acid [2-(2-fluoro-ethylamino)-ethyl]-amide hydrochloride; 1-Methyl-2-(6-trifluoromethoxy-benzothiazol-2-ylamino)-1H-benzoimidazole-5-carboxylic acid ((S)-2,3-dihydroxy-propyl)-amide; 1-Methyl-2-(6-trifluoromethoxy-benzothiazol-2-ylamino)-1H-benzoimidazole-5-carboxylic acid ((R)-2,3-dihydroxy-propyl)-amide; 1-Methyl-2-(6-trifluoromethoxy-benzothiazol-2-ylamino)-1H-benzoimidazole-5-carboxylic acid ((1R,2S,3R,4R)-2,3-dihydroxy-4-hydroxymethyl-cyclopentyl)-amide; 1-Methyl-2-(6-trifluoromethoxy-benzothiazol-2-ylamino)-1H-benzoimidazole-5-carboxylic acid ((2S,3R,4R,5S,6R)-2,4,5-trihydroxy-6-hydroxymethyl-tetrahydro-pyran-3-yl)-amide; 1-Methyl-2-(6-trifluoromethoxy-benzothiazol-2-ylamino)-1H-benzoimidazole-5-carboxylic acid bis-(2-hydroxy-ethyl)-amide; 1-Methyl-2-(6-trifluoromethoxy-benzothiazol-2-ylamino)-1H-benzoimidazole-5-carboxylic acid (4-hydroxy-butyl)-amide; 1-Methyl-2-(6-trifluoromethoxy-benzothiazol-2-ylamino)-1H-benzoimidazole-5-carboxylic acid [2-(2-hydroxy-ethoxy)-ethyl]-amide; 2-(6-Chloro-benzothiazol-2-ylamino)-1-methyl-1H-benzoimidazole-5-carboxylic acid (4-hydroxy-butyl)-amide; 2-(6-Chloro-benzothiazol-2-ylamino)-1-methyl-1H-benzoimidazole-5-carboxylic acid [2-(2-hydroxy-ethoxy)-ethyl]-amide; 1-Methyl-2-(6-trifluoromethoxy-benzothiazol-2-ylamino)-1H-benzoimidazole-5-carboxylic acid pyrrolidin-3-ylamide hydrochloride; 2-(6-Chloro-benzothiazol-2-ylamino)-1-methyl-1H-benzoimidazole-5-carboxylic acid (R)-pyrrolidin-3-ylamide hydrochloride; 2-(6-Chloro-benzothiazol-2-ylamino)-1-methyl-1H-benzoimidazole-5-carboxylic acid (S)-pyrrolidin-3-ylamide hydrochloride; 2-(6-Chloro-benzothiazol-2-ylamino)-1-methyl-1H-benzoimidazole-5-carboxylic acid [(R)-1-(2-hydroxy-ethyl)-pyrrolidin-3-yl]-amide; 2-(6-Chloro-benzothiazol-2-ylamino)-1-methyl-1H-benzoimidazole-5-carboxylic acid [(S)-1-(2-hydroxy-ethyl)-pyrrolidin-3-yl]-amide; 1-Methyl-2-(6-trifluoromethoxy-benzothiazol-2-ylamino)-1H-benzoimidazole-5-carboxylic acid [1-((R)-2-hydroxy-propyl)-pyrrolidin-3-yl]-amide; 2-(6-Chloro-benzothiazol-2-ylamino)-1-methyl-1H-benzoimidazole-5-carboxylic acid [(R)-1-((S)-2-hydroxy-propionyl)-pyrrolidin-3-yl]-amide; 2-(6-Chloro-benzothiazol-2-ylamino)-1-methyl-1H-benzoimidazole-5-carboxylic acid [(R)-1-((R)-2-hydroxy-propyl)-pyrrolidin-3-yl]-amide; 1-Methyl-2-(6-trifluoromethyl-benzothiazol-2-ylamino)-1H-benzoimidazole-5-carboxylic acid [(R)-1-((R)-2-hydroxy-propyl)-pyrrolidin-3-yl]-amide; 1-Methyl-2-(6-trifluoromethoxy-benzothiazol-2-ylamino)-1H-benzoimidazole-5-carboxylic acid [1-(2-hydroxy-2-methyl-propyl)-pyrrolidin-3-yl]-amide; 3-(3-{[2-(6-Chloro-benzothiazol-2-ylamino)-1-methyl-1H-benzoimidazole-5-carbonyl]-amino}-pyrrolidin-1-yl)-propionic acid; 2-(6-Chloro-benzothiazol-2-ylamino)-1-methyl-1H-benzoimidazole-5-carboxylic acid [1-(2-methanesulfonylamino-ethyl)-pyrrolidin-3-yl]-amide; 2-(6-Chloro-benzothiazol-2-ylamino)-1-(2-methoxy-ethyl)-1H-benzoimidazole-5-carboxylic acid [1-(2-hydroxy-ethyl)-piperidin-4-yl]-amide; 2-(6-Chloro-benzothiazol-2-ylamino)-1-methyl-1H-benzoimidazole-5-carboxylic acid (piperidin-4-ylmethyl)-amide hydrochloride; 2-(6-Chloro-benzothiazol-2-ylamino)-1-methyl-1H-benzoimidazole-5-carboxylic acid [1-(2-hydroxy-ethyl)-piperidin-4-ylmethyl]-amide; 2-(6-Chloro-benzothiazol-2-ylamino)-1-(2-methoxy-ethyl)-1H-benzoimidazole-5-carboxylic acid [1-(2-hydroxy-ethyl)-piperidin-4-ylmethyl]-amide; [4-(2-Hydroxy-ethyl)-piperazin-1-yl]-[1-methyl-2-(6-trifluoromethoxy-benzothiazol-2-ylamino)-H-benzoimidazol-5-yl]-methanone; [2-(6-Chloro-benzothiazol-2-ylamino)-1-methyl-1H-benzoimidazol-5-yl]-[4-(2-hydroxy-ethyl)-piperazin-1-yl]-methanone; [4-(3-Hydroxy-propyl)-piperidin-1-yl]-[1-methyl-2-(6-trifluoromethoxy-benzothiazol-2-ylamino)-1H benzoimidazol-5-yl]-methanone; 2-(6-Chloro-benzothiazol-2-ylamino)-1-methyl-1H-benzoimidazole-5-carboxylic acid [(R)-1-(2-dimethylamino-acetyl)-pyrrolidin-3-yl]-amide; 2-(6-Chloro-benzothiazol-2-ylamino)-1-methyl-1H-benzoimidazole-5-carboxylic acid (R)-piperidin-3-ylamide hydrochloride; 2-(6-Chloro-benzothiazol-2-ylamino)-1-methyl-1H-benzoimidazole-5-carboxylic acid (S)-piperidin-3-ylamide hydrochloride; 2-(6-Chloro-benzothiazol-2-ylamino)-1-methyl-1H-benzoimidazole-5-carboxylic acid [(R)-1-(2-dimethylamino-acetyl)-piperidin-3-yl]-amide; 2-(6-Chloro-benzothiazol-2-ylamino)-1-methyl-1H-benzoimidazole-5-carboxylic acid [(S)-1-(2-dimethylamino-acetyl)-piperidin-3-yl]-amide; 2-(6-Chloro-benzothiazol-2-ylamino)-1-methyl-1H-benzoimidazole-5-carboxylic acid [1-(2-dimethylamino-acetyl)-piperidin-4-yl]-amide; 2-(6-Chloro-benzothiazol-2-ylamino)-1-methyl-1H-benzoimidazole-5-carboxylic acid [1-(2-dimethylamino-acetyl)-piperidin-4-ylmethyl]-amide; 2-(6-Chloro-benzothiazol-2-ylamino)-1-(2-methoxy-ethyl)-1H-benzoimidazole-5-carboxylic acid [1-(2-dimethylamino-acetyl)-piperidin-4-ylmethyl]-amide; 2-(6-Chloro-benzothiazol-2-ylamino)-1-methyl-1H benzoimidazole-5-carboxylic acid ((R)-1-methyl-pyrrolidin-3-yl)-amide; 2-(6-Chloro-benzothiazol-2 ylamino)-1-methyl-1H-benzoimidazole-5-carboxylic acid ((S)-1-methyl-pyrrolidin-3-yl)-amide; 2-(6-Chloro-benzothiazol-2-ylamino)-1-methyl-1H-benzoimidazole-5-carboxylic acid (1-methyl-piperidin-2-ylmethyl)-amide; 2-(6-Chloro-benzothiazol-2-ylamino)-1-methyl-1H-benzoimidazole-5-carboxylic acid (1-methyl-piperidin-4-yl)-amide; 2-(6-Chloro-benzothiazol-2-ylamino)-1-methyl-1H-benzoimidazole-5-carboxylic acid (1-methanesulfonyl-piperidin-4-yl)-amide; 2-(6-Chloro-benzothiazol-2-ylamino)-1-methyl-1H-benzoimidazole-5-carboxylic acid morpholin-4-ylamide; 1-Methyl-2-(6-trifluoromethoxy-benzothiazol-2-ylamino)-1H-benzoimidazole-5-carboxylic acid (2-methanesulfonylamino-ethyl)-amide; 1-Methyl-2-(6-trifluoromethoxy-benzothiazol-2-ylamino)-1H-benzoimidazole-5-carboxylic acid [2-(2-dimethylamino-acetylamino)-ethyl]-amide; 2-(6-Chloro-benzothiazol-2-ylamino)-1-methyl-1H-benzoimidazole-5-carboxylic acid [2-(2-dimethylamino-acetylamino)-ethyl]-amide; 1-Methyl-2-(6-trifluoromethoxy-benzothiazol-2-ylamino)-1H-benzoimidazole-5-carboxylic acid [2-(2-hydroxy-acetylamino)-ethyl]-amide; 1-Methyl-2-(6-trifluoromethoxy-benzothiazol-2-ylamino)-1H-benzoimidazole-5-carboxylic acid [2-((S)-2-hydroxy-propionylamino)-ethyl]-amide; 1-Methyl-2-(6-trifluoromethoxy-benzothiazol-2-ylamino)-1H-benzoimidazole-5-carboxylic acid (2-imidazol-1-yl-ethyl)-amide; 1-Methyl-2-(6-trifluoromethoxy-benzothiazol-2-ylamino)-1H-benzoimidazole-5-carboxylic acid (2-pyrazol-1-yl-ethyl)-amide; 1-Methyl-2-(6-trifluoromethoxy-benzothiazol-2-ylamino)-1H-benzoimidazole-5-carboxylic acid [2-(2-oxo-pyrrolidin-1-yl)-ethyl]-amide; 1-Methyl-2-(6-trifluoromethoxy-benzothiazol-2-ylamino)-1H-benzoimidazole-5-carboxylic acid [2-(2-oxo-imidazolidin-1-yl)-ethyl]-amide; 2-(6-Chloro-benzothiazol-2-ylamino)-1-methyl-1H-benzoimidazole-5-carboxylic acid

[2-(3-oxo-piperazin-1-yl)-ethyl]-amide; 2-(6-Chloro-benzothiazol-2-ylamino)-1-(2-methoxy-ethyl)-1H-benzoimidazole-5-carboxylic acid [2-(3-oxo-piperazin-1-yl)-ethyl]-amide; 1-Methyl-2-(6-trifluoromethoxy-benzothiazol-2-ylamino)-1H-benzoimidazole-5-carboxylic acid (2-piperidin-1-yl-ethyl)-amide; 2-(6-Chloro-benzothiazol-2-ylamino)-1-methyl-1H-benzoimidazole-5-carboxylic acid (2-piperidin-1-yl-ethyl)-amide; 2-(6-Chloro-benzothiazol-2-ylamino)-1-methyl-1H-benzoimidazole-5-carboxylic acid [2-(4,4-difluoro-piperidin-1-yl)-ethyl]-amide; 2-(6-Chloro-benzothiazol-2-ylamino)-1-methyl-1H-benzoimidazole-5-carboxylic acid [2-(3,3-difluoro-piperidin-1-yl)-ethyl]-amide; 1-Methyl-2-(6-trifluoromethoxy-benzothiazol-2-ylamino)-1H-benzoimidazole-5-carboxylic acid [2-(4-methyl-piperazin-1-yl)-ethyl]-amide; 2-(6-Chloro-benzothiazol-2-ylamino)-1-methyl-1H-benzoimidazole-5-carboxylic acid [2-(4-methyl-piperazin-1-yl)-ethyl]-amide; 2-(6-Chloro-benzothiazol-2-ylamino)-1-methyl-1H-benzoimidazole-5-carboxylic acid (2-piperazin-1-yl-ethyl)-amide hydrochloride; 2-(6-Chloro-benzothiazol-2-ylamino)-1-methyl-1H-benzoimidazole-5-carboxylic acid (2-morpholin-4-yl-ethyl)-amide; 1-Methyl-2-(6-trifluoromethyl-benzothiazol-2-ylamino)-1H-benzoimidazole-5-carboxylic acid (2-morpholin-4-yl-ethyl)-amide; 1-Methyl-2-(6-trifluoromethoxy-benzothiazol-2-ylamino)-1H-benzoimidazole-5-carboxylic acid [2-(1,1-dioxo-thiomorpholin-4-yl)-ethyl]-amide; 2-(6-Chloro-benzothiazol-2-ylamino)-1-methyl-1H-benzoimidazole-5-carboxylic acid (2-amino-ethyl)-amide hydrochloride; 1-Methyl-2-(6-trifluoromethoxy-benzothiazol-2-ylamino)-1H-benzoimidazole-5-carboxylic acid (3-amino-propyl)-amide hydrochloride; 2-(6-Chloro-benzothiazol-2-ylamino)-1-methyl-1H-benzoimidazole-5-carboxylic acid (3-amino-propyl)-amide hydrochloride; 1-Methyl-2-(6-trifluoromethoxy-benzothiazol-2-ylamino)-1H-benzoimidazole-5-carboxylic acid (4-amino-butyl)-amide hydrochloride; 2-(6-Chloro-benzothiazol-2-ylamino)-1-methyl-1H-benzoimidazole-5-carboxylic acid (4-amino-butyl)-amide hydrochloride; 1-Methyl-2-(6-trifluoromethoxy-benzothiazol-2-ylamino)-1H-benzoimidazole-5-carboxylic acid (3-dimethylamino-propyl)-amide; 2-(6-Chloro-benzothiazol-2-ylamino)-1-methyl-1H-benzoimidazole-5-carboxylic acid (3-dimethylamino-propyl)-amide; 1-Methyl-2-(6-trifluoromethyl-benzothiazol-2-ylamino)-1H-benzoimidazole-5-carboxylic acid (3-dimethylamino-propyl)-amide; 1-Methyl-2-(6-trifluoromethoxy-benzothiazol-2-ylamino)-1H-benzoimidazole-5-carboxylic acid (3-diethylamino-propyl)-amide; 2-(6-Chloro-benzothiazol-2-ylamino)-1-methyl-1H-benzoimidazole-5-carboxylic acid (3-diethylamino-propyl)-amide; 1-Methyl-2-(6-trifluoromethyl-benzothiazol-2-ylamino)-1H-benzoimidazole-5-carboxylic acid (3-diethylamino-propyl)-amide; 2-(6-Chloro-benzothiazol-2-ylamino)-1-methyl-1H-benzoimidazole-5-carboxylic acid (3-pyrrolidin-1-yl-propyl)-amide; 1-Methyl-2-(6-trifluoromethoxy-benzothiazol-2-ylamino)-1H-benzoimidazole-5-carboxylic acid [3-(4-methyl-piperazin-1-yl)-propyl]-amide; 2-(6-Chloro-benzothiazol-2-ylamino)-1-methyl-1H-benzoimidazole-5-carboxylic acid [3-(4-methyl-piperazin-1-yl)-propyl]-amide; 1-Methyl-2-(6-trifluoromethyl-benzothiazol-2-ylamino)-1H-benzoimidazole-5-carboxylic acid [3-(4-methyl-piperazin-1-yl)-propyl]-amide; 1-Methyl-2-(6-trifluoromethoxy-benzothiazol-2-ylamino)-1H-benzoimidazole-5-carboxylic acid (3-morpholin-4-yl-propyl)-amide; 2-(6-Chloro-benzothiazol-2-ylamino)-1-methyl-1H-benzoimidazole-5-carboxylic acid (3-morpholin-4-yl-propyl)-amide; 1-Methyl-2-(6-trifluoromethoxy-benzothiazol-2-ylamino)-1H-benzoimidazole-5-carboxylic acid (4-diethylamino-butyl)-amide; 6-Diethylamino-1-methyl-2-(6-trifluoromethoxy-benzothiazol-2-ylamino)-1H-benzoimidazole-5-carboxylic acid dimethylcarbamoylmethyl-amide; 6-Diethylamino-1-methyl-2-(6-trifluoromethoxy-benzothiazol-2-ylamino)-1H-benzoimidazole-5-carboxylic acid (2-morpholin-4-yl-ethyl)-amide; 1-Methyl-2-(6-methyl-benzothiazol-2-ylamino)-1H-benzoimidazole-5-carboxylic acid dimethylcarbamoylmethyl-amide; 2-(6-Ethoxy-benzothiazol-2-ylamino)-1-methyl-1H-benzoimidazole-5-carboxylic acid dimethylcarbamoylmethyl-amide; 2-(6-Isopropyl-benzothiazol-2-ylamino)-1-methyl-1H-benzoimidazole-5-carboxylic acid dimethylcarbamoylmethyl-amide; 2-(6-Chloro-benzothiazol-2-ylamino)-1-(2-methoxy-ethyl)-1H-benzoimidazole-5-carboxylic acid dimethylcarbamoylmethyl-amide; 2-(6-Chloro-benzothiazol-2-ylamino)-1-(2-methylamino-ethyl)-1H-benzoimidazole-5-carboxylic acid dimethylcarbamoylmethyl-amide hydrochloride; 1-Methyl-2-(6-trifluoromethoxy-benzothiazol-2-ylamino)-1H-benzoimidazole-5-carboxylic acid ((S)-1-dimethylcarbamoyl-2-hydroxy-ethyl)-amide; 1-Methyl-2-(6-trifluoromethyl-benzothiazol-2-ylamino)-1H-benzoimidazole-5-carboxylic acid ((S)-5-amino-1-dimethylcarbamoyl-pentyl)-amide hydrochloride; 1-Methyl-2-(6-trifluoromethyl-benzothiazol-2-ylamino)-1H-benzoimidazole-5-carboxylic acid ((S)-5-dimethylamino-1-dimethylcarbamoyl-pentyl)-amide; 2-(6-Chloro-benzothiazol-2-ylamino)-1-methyl-1H-benzoimidazole-5-carboxylic acid (2-dimethylcarbamoyl-ethyl)-amide; 1-Methyl-2-(6-trifluoromethyl-benzothiazol-2-ylamino)-1H-benzoimidazole-5-carboxylic acid (2-dimethylcarbamoyl-ethyl)-amide; 2-(6-Chloro-benzothiazol-2-ylamino)-1-methyl-1H-benzoimidazole-5-carboxylic acid (3-morpholin-4-yl-3-oxo-propyl)-amide; 1-Methyl-2-(6-trifluoromethyl-benzothiazol-2-ylamino)-1H-benzoimidazole-5-carboxylic acid (3-morpholin-4-yl-3-oxo-propyl)-amide; 1-Methyl-2-(6-trifluoromethyl-benzothiazol-2-ylamino)-1H-benzoimidazole-5-carboxylic acid [3-(4-methyl-piperazin-1-yl)-3-oxo-propyl]-amide; 2-(6-Chloro-benzothiazol-2-ylamino)-1-methyl-1H-benzoimidazole-5-carboxylic acid (3-dimethylcarbamoyl-propyl)-amide; 2-(6-Chloro-benzothiazol-2-ylamino)-1-methyl-1H-benzoimidazole-5-carboxylic acid [4-(4-methyl-piperazin-1-yl)-4-oxo-butyl]-amide; 4-{[2-(6-Chloro-benzothiazol-2-ylamino)-1-methyl-1H-benzoimidazole-5-carbonyl]-amino}-trans-cyclohexanecarboxylic acid; 2-(6-Chloro-benzothiazol-2-ylamino)-1-methyl-1H-benzoimidazole-5-carboxylic acid (4-tra/7S-dimethylcarbamoyl-cyclohexyl)-amide; 2-(6-Chloro-benzothiazol-2-ylamino)-1-methyl-1H-benzoimidazole-5-carboxylic acid methylcarbamoylmethyl-amide; 1-Methyl-2-(6-trifluoromethyl-benzothiazol-2-ylamino)-1H-benzoimidazole-5-carboxylic acid methylcarbamoylmethyl-amide; 2-(6-Chloro-benzothiazol-2-ylamino)-1-methyl-1H-benzoimidazole-5-carboxylic acid [((R)-2-hydroxy-propylcarbamoyl)-methyl]-amide; 2-(6-Chloro-benzothiazol-2-ylamino)-1-methyl-1H-benzoimidazole-5-carboxylic acid[(2-methanesulfonyl-ethylcarbamoyl)-methyl]-amide; 2-(6-Chloro-benzothiazol-2-ylamino)-1-methyl-1H-benzoimidazole-5-carboxylic acid [(tetrahydro-furan-3-ylcarbamoyl)-methyl]-amide; 2-(6-Chloro-benzothiazol-2-ylamino)-1-methyl-1H-benzoimidazole-5-carboxylic acid [(tetrahydro-pyran-4-ylcarbamoyl)-methyl]-amide; 2-(6-Chloro-benzothiazol-2-ylamino)-1-methyl-1H-benzoimidazole-5-carboxylic acid [(1-methyl-piperidin-4-ylcarbamoyl)-methyl]-amide; 2-(6-Chloro-benzothiazol-2-ylamino)-1-methyl-1H-benzoimidazole-5-carboxylic acid ((R)-piperidin-3-ylcarbamoylmethyl)-amide hydrochloride;

2-(6-Chloro-benzothiazol-2-ylamino)-1-methyl-1H-benzo-imidazole-5-carboxylic acid [((R)-1-methyl-piperidin-3-yl-carbamoyl)-methyl]-amide; 1-Methyl-2-(6-trifluoromethoxy-benzothiazol-2-ylamino)-1H-benzoimidazole-5-carboxylic acid [(4-hydroxy-benzylcarbamoyl)-methyl]-amide; 1-Methyl-2-(6-trifluoromethoxy-benzothiazol-2-ylamino)-1H-benzoimidazole-5-carboxylic acid {[(2-hydroxy-ethyl)-methyl-carbamoyl]-methyl}-amide; 2-(6-Chloro-benzothiazol-2-ylamino)-1-methyl-1H-benzoimidazole-5-carboxylic acid {[(2-hydroxy-ethyl)-methyl-carbamoyl]-methyl}-amide; 1-Methyl-2-(6-trifluoromethoxy-benzothiazol-2-ylamino)-1H-benzoimidazole-5-carboxylic acid {[bis-(2-hydroxy-ethyl)-carbamoyl]-methyl}-amide; 2-(6-Chloro-benzothiazol-2-ylamino)-1-methyl-1H-benzoimidazole-5-carboxylic acid {[methyl-(tetrahydro-pyran-4-yl)-carbamoyl]-methyl}-amide; 2-(6-Chloro-benzothiazol-2-ylamino)-1-methyl-1H-benzoimidazole-5-carboxylic acid [(methyl-pyrrolidin-3-yl-carbamoyl)-methyl]-amide hydrochloride; 2-(6-Chloro-benzothiazol-2-ylamino)-1-methyl-1H-benzoimidazole-5-carboxylic acid {[methyl-(1-methyl-pyrrolidin-3-yl)-carbamoyl]-methyl}-amide; 2-(6-Chloro-benzothiazol-2-ylamino)-1-methyl-1H-benzoimidazole-5-carboxylic acid [(methyl-piperidin-3-yl-carbamoyl)-methyl]-amide hydrochloride; 2-(6-Chloro-benzothiazol-2-ylamino)-1-methyl-1H-benzoimidazole-5-carboxylic acid (2-oxo-2-pyrrolidin-1-yl-ethyl)-amide; 1-Methyl-2-(6-trifluoromethoxy-benzothiazol-2-ylamino)-1H-benzoimidazole-5-carboxylic acid [2-(3-hydroxy-pyrrolidin-1-yl)-2-oxo-ethyl]-amide; 2-(6-Chloro-benzothiazol-2-ylamino)-1-methyl-1H-benzo-imidazole-5-carboxylic acid [2-(3-hydroxy-pyrrolidin-1-yl)-2-oxo-ethyl]-amide; 2-(6-Chloro-benzothiazol-2-ylamino)-1-methyl-1H-benzoimidazole-5-carboxylic acid [2-((R)-3-hydroxy-pyrrolidin-1-yl)-2-oxo-ethyl]-amide; 2-(6-Chloro-benzothiazol-2-ylamino)-1-methyl-1H-benzoimidazole-5-carboxylic acid [2-((S)-3-hydroxy-pyrrolidin-1-yl)-2-oxo-ethyl]-amide; 1-Methyl-2-(6-trifluoromethyl-benzothiazol-2-ylamino)-1H-benzoimidazole-5-carboxylic acid [2-((R)-3-hydroxy-pyrrolidin-1-yl)-2-oxo-ethyl]-amide; 1-Methyl-2-(6-trifluoromethyl-benzothiazol-2-ylamino)-1H-benzoimidazole-5-carboxylic acid [2-((S)-3-hydroxy-pyrrolidin-1-yl)-2-oxo-ethyl]-amide; 2-(6-Chloro-benzothiazol-2-ylamino)-1-(2-methoxy-ethyl)-1H-benzoimidazole-1-carboxylic acid [2-((R)-3-hydroxy-pyrrolidin-1-yl)-2-oxo-ethyl]-amide; 2-(6-Chloro-benzothiazol-2-ylamino)-1-(2-methoxy-ethyl)-1H-benzoimidazole-5-carboxylic acid [2-((S)-3-hydroxy-pyrrolidin-1-yl)-2-oxo-ethyl]-amide; 1-Methyl-2-(6-trifluoromethoxy-benzothiazol-2-ylamino)-1H-benzoimidazole-5-carboxylic acid [2-((S)-2-hydroxymethyl-pyrrolidin-1-yl)-2-oxo-ethyl]-amide; 1-Methyl-2-(6-trifluoromethoxy-benzothiazol-2-ylamino)-1H-benzoimidazole-5-carboxylic acid [2-((3S,4S)-3,4-dihydroxy-pyrrolidin-1-yl)-2-oxo-ethyl]-amide; 2-(6-Chloro-benzothiazol-2-ylamino)-1-methyl-1H-benzoimidazole-5-carboxylic acid [2-((R)-3-methoxy-pyrrolidin-1-yl)-2-oxo-ethyl]-amide; 2-(6-Chloro-benzothiazol-2-ylamino)-1-methyl-1H-benzoimidazole-5-carboxylic acid [2-((S)-3-methoxy-pyrrolidin-1-yl)-2-oxo-ethyl]-amide; 1-Methyl-2-(6-trifluoromethyl-benzothiazol-2-ylamino)-1H-benzoimidazole-5-carboxylic acid [2-((S)-3-methoxy-pyrrolidin-1-yl)-2-oxo-ethyl]-amide; 2-(6-Chloro-benzothiazol-2-ylamino)-1-methyl-1H-benzoimidazole-5-carboxylic acid [2-((S)-3-amino-pyrrolidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-((S)-3-amino-pyrrolidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-((R)-3-methyl-amino-pyrrolidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-((S)-3-methyl-amino-pyrrolidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-((R)-3-dimethyl-amino-pyrrolidin-1-yl)-2-oxo-ethyl]-amide; 1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide; 2-(6-Chloro-benzothiazol-2-ylamino)-1-methyl-1H-benzoimidazole-5-carboxylic acid [2-((R)-3-dimethylamino-pyrrolidin-1-yl)-2-oxo-ethyl]-amide; 2-(6-Chloro-benzothiazol-2-ylamino)-1-methyl-1H-benzoimidazole-5-carboxylic acid [2-((S)-3-dimethylamino-pyrrolidin-1-yl)-2-oxo-ethyl]-amide; 2-(6-Chloro-benzothiazol-2-ylamino)-1-methyl-1H-benzoimidazole-5-carboxylic acid [2-((S)-2-dimethylcarbamoyl-pyrrolidin-1-yl)-2-oxo-ethyl]-amide; 3-Methyl-2-(6-trifluoromethoxy-benzothiazol-2-ylamino)-3H-imidazo[4,5-b]pyridine-6-carboxylic acid (2-morpholin-4-yl-2-oxo-ethyl)-amide; 2-(6-Chloro-benzothiazol-2-ylamino)-1-methyl-1H-benzoimidazole-5-carboxylic acid (2-morpholin-4-yl-2-oxo-ethyl)-amide; 1-Methyl-2-(6-trifluoromethyl-benzothiazol-2-ylamino)-1H-benzoimidazole-5-carboxylic acid (2-morpholin-4-yl-2-oxo-ethyl)-amide; 2-(6-Chloro-benzothiazol-2-ylamino)-1-methyl-1H-benzo-imidazole-5-carboxylic acid (2-oxo-2-thiomorpholin-4-yl-ethyl)-amide; 2-(6-Chloro-benzothiazol-2-ylamino)-1-methyl-1H-benzoimidazole-5-carboxylic acid [2-(1,1-dioxo-thiomorpholin-4-yl)-2-oxo-ethyl]-amide; 2-(6-Chloro-benzothiazol-2-ylamino)-1-methyl-1H-benzoimidazole-5-carboxylic acid (2-oxo-2-piperazin-1-yl-ethyl)-amide hydrochloride; 2-(6-Chloro-benzothiazol-2-ylamino)-1-methyl-1H-benzoimidazole-5-carboxylic acid [2-(4-methyl-piperazin-1-yl)-2-oxo-ethyl]-amide; 1-Methyl-2-(6-trifluoromethyl-benzothiazol-2-ylamino)-1H-benzoimidazole-5-carboxylic acid [2-(4-methyl-piperazin-1-yl)-2-oxo-ethyl]-amide; 2-(6-Chloro-benzothiazol-2-ylamino)-1-(2-methoxy-ethyl)-1H-benzoimidazole-5-carboxylic acid [2-(4-methyl-piperazin-1-yl)-2-oxo-ethyl]-amide; 2-(6-Chloro-benzothiazol-2-ylamino)-1-methyl-1H-benzoimidazole-5-carboxylic acid [2-(4-methanesulfonyl-piperazin-1-yl)-2-oxo-ethyl]-amide; 2-(6-Chloro-benzothiazol-2-ylamino)-1-methyl-1H-benzoimidazole-5-carboxylic acid [2-(4-dimethylsulfamoyl-piperazin-1-yl)-2-oxo-ethyl]-amide; 1-Methyl-2-(6-trifluoromethoxy-benzothiazol-2-ylamino)-1H-benzoimidazole-5-carboxylic acid [2-(3-hydroxy-piperidin-1-yl)-2-oxo-ethyl]-amide; 1-Methyl-2-(6-trifluoromethyl-benzothiazol-2-ylamino)-1H-benzoimidazole-5-carboxylic acid [2-((R)-3-hydroxy-piperidin-1-yl)-2-oxo-ethyl]-amide; 2-(6-Chloro-benzothiazol-2-ylamino)-1-methyl-1H-benzoimidazole-5-carboxylic acid [2-((S)-3-hydroxy-piperidin-1-yl)-2-oxo-ethyl]-amide; 1-Methyl-2-(6-trifluoromethyl-benzothiazol-2-ylamino)-1H-benzoimidazole-5-carboxylic acid [2-((S)-3-hydroxy-piperidin-1-yl)-2-oxo-ethyl]-amide; 1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide; 2-(6-Chloro-benzothiazol-2-ylamino)-1-methyl-1H-benzoimidazole-5-carboxylic acid [2-(4-hydroxy-piperidin-1-yl)-2-oxo-ethyl]-amide; 1-Methyl-2-(6-trifluoromethyl-benzothiazol-2-ylamino)-1H-benzoimidazole-5-carboxylic acid [2-(4-hydroxy-piperidin-1-yl)-2-oxo-ethyl]-amide;

2-(6-Chloro-benzothiazol-2-ylamino)-1-(2-methoxy-ethyl)-1H-benzoimidazole-5-carboxylic acid [2-(4-hydroxy-piperidin-1-yl)-2-oxo-ethyl]-amide; 1-Methyl-2-(6-trifluoromethoxy-benzothiazol-2-ylamino)-1H-benzoimidazole-5-carboxylic acid [2-(2-hydroxymethyl-piperidin-1-yl)-2-oxo-ethyl]-amide; 1-Methyl-2-(6-trifluoromethoxy-benzothiazol-2-ylamino)-1H-benzoimidazole-5-carboxylic acid [2-(3-hydroxymethyl-piperidin-1-yl)-2-oxo-ethyl]-amide; 1-Methyl-2-(6-trifluoromethyl-benzothiazol-2-ylamino)-1H-benzoimidazole-5-carboxylic acid [2-(4-hydroxymethyl-piperidin-1-yl)-2-oxo-ethyl]-amide; 2-(6-Chloro-benzothiazol-2-ylamino)-1-methyl-1H-benzoimidazole-5-carboxylic acid [2-(4-hydroxymethyl-piperidin-1-yl)-2-oxo-ethyl]-amide; 2-(6-Chloro-benzothiazol-2-ylamino)-1-(2-methoxy-ethyl)-1H-benzoimidazole-5-carboxylic acid [2-(4-hydroxymethyl-piperidin-1-yl)-2-oxo-ethyl]-amide; 2-(6-Chloro-benzothiazol-2-ylamino)-1-methyl-1H-benzoimidazole-5-carboxylic acid [2-((S)-3-methoxy-piperidin-1-yl)-2-oxo-ethyl]-amide; 1-Methyl-2-(6-trifluoromethyl-benzothiazol-2-ylamino)-1H-benzoimidazole-5-carboxylic acid [2-((S)-3-methoxy-piperidin-1-yl)-2-oxo-ethyl]-amide; 1-Methyl-2-(6-trifluoromethyl-benzothiazol-2-ylamino)-1H-benzoimidazole-5-carboxylic acid [2-((R)-3-methoxy-piperidin-1-yl)-2-oxo-ethyl]-amide; 1-Methyl-2-(6-trifluoromethoxy-benzothiazol-2-ylamino)-1H-benzoimidazole-5-carboxylic acid [2-(4-methoxymethyl-piperidin-1-yl)-2-oxo-ethyl]-amide; 1-Methyl-2-(6-trifluoromethoxy-benzothiazol-2-ylamino)-1H-benzoimidazole-5-carboxylic acid [2-(4-fluoromethyl-piperidin-1-yl)-2-oxo-ethyl]-amide; 1-Methyl-2-(6-trifluoromethoxy-benzothiazol-2-ylamino)-1H-benzoimidazole-5-carboxylic acid [2-oxo-2-(4-trifluoromethyl-piperidin-1-yl)-ethyl]-amide; 1-Methyl-2-(6-trifluoromethoxy-benzothiazol-2-ylamino)-1H-benzoimidazole-5-carboxylic acid [2-(4-cyano-piperidin-1-yl)-2-oxo-ethyl]-amide; 1-Methyl-2-(6-trifluoromethoxy-benzothiazol-2-ylamino)-1H-benzoimidazole-5-carboxylic acid [2-(4-carbamoyl-piperidin-1-yl)-2-oxo-ethyl]-amide; 1-Methyl-2-(6-trifluoromethoxy-benzothiazol-2-ylamino)-1H-benzoimidazole-5-carboxylic acid {2-oxo-2-[4-(pyrimidin-2-yloxy)-piperidin-1-yl]-ethyl}-amide l-Methyl-2-(6-trifluoromethoxy-benzothiazol-2-ylamino)-1H-benzoimidazole-5-carboxylic acid [2-(4-methylamino-piperidin-1-yl)-2-oxo-ethyl]-amide hydrochloride; 2-(6-Chloro-benzothiazol-2-ylamino-1-methyl-1H-benzoimidazole-5-carboxylic acid [2-(4-methylamino-piperidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-(4-dimethylamino-piperidin-1-yl)-2-oxo-ethyl]-amide; 2-(6-Chloro-benzothiazol-2-ylamino)-1-methyl-1H-benzoimidazole-5-carboxylic acid [2-(4-dimethylamino-piperidin-1-yl)-2-oxo-ethyl]-amide; 2-(6-Chloro-benzothiazol-2-ylamino)-1-methyl-1H-benzoimidazole-5-carboxylic acid [2-(4-methylaminomethyl-piperidin-1-yl)-2-oxo-ethyl]-amide hydrochloride; 1-Methyl-2-(6-trifluoromethoxy-benzothiazol-2-ylamino)-1H-benzoimidazole-5-carboxylic acid [2-(4-dimethylaminomethyl-piperidin-1-yl)-2-oxo-ethyl]-amide; 2-(6-Chloro-benzothiazol-2-ylamino)-1-methyl-1H-benzoimidazole-5-carboxylic acid [2-(4-dimethylaminomethyl-piperidin-1-yl)-2-oxo-ethyl]-amide; 2-(6-Chloro-benzothiazol-2-ylamino)-1-methyl-1H-benzoimidazole-5-carboxylic acid [2-(3-methylaminomethyl-piperidin-1-yl)-2-oxo-ethyl]-amid hydrochloride; 2-(6-Chloro-benzothiazol-2-ylamino)-1-methyl-1H-benzoimidazole-5-carboxylic acid [2-(3-dimethylaminomethyl-piperidin-1-yl)-2-oxo-ethyl]-amide; 2-(6-Chloro-benzothiazol-2-ylamino)-1-methyl-1H-benzoimidazole-5-carboxylic acid ((S)-1-dimethylcarbamoyl-ethyl)-amide; 1-Methyl-2-(6-trifluoromethyl-benzothiazol-2-ylamino)-1H-benzoimidazole-5-carboxylic acid ((S)-1-dimethylcarbamoyl-ethyl)-amide; 2-(6-Chloro-benzothiazol-2-ylamino)-1-methyl-1H-benzoimidazole-5-carboxylic acid [(S)-1-methyl-2-(4-methyl-piperazin-1-yl)-2-oxo-ethyl]-amide; 2-(6-Chloro-benzothiazol-2-ylamino)-1-methyl-1H-benzoimidazole-5-carboxylic acid ((S)-1-methyl-2-morpholin-4-yl-2-oxo-ethyl)-amide; 1-Methyl-2-(6-trifluoromethyl-benzothiazol-2-ylamino)-1H-benzoimidazole-5-carboxylic acid ((S)-1-methyl-2-morpholin-4-yl-2-oxo-ethyl)-amide; 2-(6-Chloro-benzothiazol-2-ylamino)-1-methyl-1H-benzoimidazole-5-carboxylic acid ((R)-1-dimethylcarbamoyl-ethyl)-amide; 1-Methyl-2-(6-trifluoromethyl-benzothiazol-2-ylamino)-1H-benzoimidazole-5-carboxylic acid ((R)-1-dimethylcarbamoyl-ethyl)-amide; 2-(6-Chloro-benzothiazol-2-ylamino)-1-methyl-1H-benzoimidazole-5-carboxylic acid [(R)-1-methyl-2-(4-methyl-piperazin-1-yl)-2-oxo-ethyl]-amide; 1-Methyl-2-(6-trifluoromethyl-benzothiazol-2-ylamino)-1H-benzoimidazole-5-carboxylic acid [(R)-1-methyl-2-(4-methyl-piperazin-1-yl)-2-oxo-ethyl]-amide; 2-(6-Chloro-benzothiazol-2-ylamino)-1-methyl-1H-benzoimidazole-5-carboxylic acid ((R)-1-methyl-2-morpholin-4-yl-2-oxo-ethyl)-amide; and 1-Methyl-2-(6-trifluoromethyl-benzothiazol-2-ylamino)-1H-benzoimidazole-5-carboxylic acid ((R)-1-methyl-2-morpholin-4-yl-2-oxo-ethyl)-amide.

Other exemplary BACH1 inhibitors useful in the compositions and methods of the disclosure include those disclosed as BACH1 inhibitors in US20130253007, which is herein incorporated by reference. Accordingly, in some embodiments, the BACH1 inhibitor is selected from the table below:

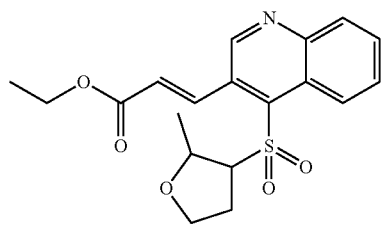 [SMILES: CCOC(=O)/C=C/c1cnc2ccccc2c1S(=O)(=O)C1CCOC1C]

(E)-3-[4-(2-Methyl-tetrahydro-furan-3-sulfonyl)-quinolin-3-yl]-acrylic acid ethyl ester

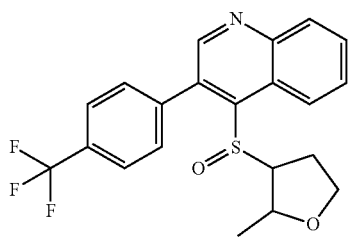 [SMILES: CC1OCCC1S(=O)c1c(-c2ccc(C(F)(F)F)cc2)cnc2ccccc12]

4-(2-Methyl-tetrahydro-furan-3-sulfinyl)-3-(4-trifluoromethyl-phenyl)-quinolone

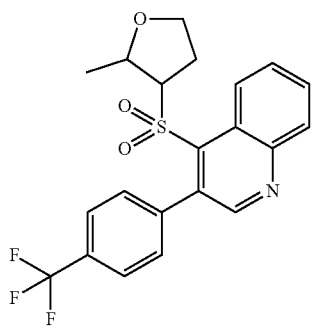 [SMILES: CC1OCCC1S(=O)(=O)c1c(-c2ccc(C(F)(F)F)cc2)cnc2ccccc12]

4-(2-Methyl-tetrahydro-furan-3-sulfonyl)-3-(4-trifluoromethyl-phenyl)-quinolone

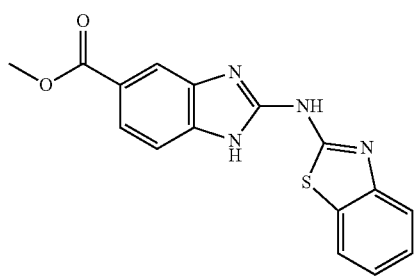 [SMILES: COC(=O)c1ccc2[nH]c(Nc3nc4ccccc4s3)nc2c1]

2-(Benzothiazol-2-ylamino)-1H-benzoimidazole-5-carboxylic acid methyl ester

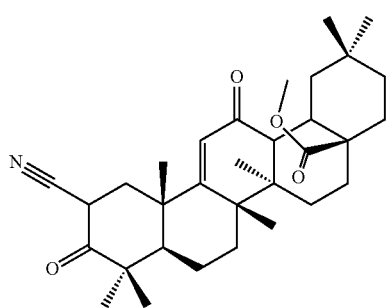

(4aS,6aR.,6bS,8aR,12aS)-11-Cyano-2,2,6a,6b,9,9,12a-heptamethyl-10,14-dioxo-1,3,4,5,6,6a,6b,7,8,8a,9,10,11,12,12a,14,14a,14b-octadecahydro-2H-picene-4a- carboxylic acid methyl ester

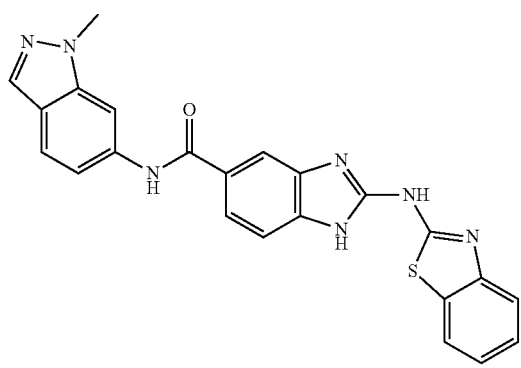 [SMILES: Cn1ncc2ccc(NC(=O)c3ccc4[nH]c(Nc5nc6ccccc6s5)nc4c3)cc21]

2-(Benzothiazol-2-ylatnino)-1H-benzoimidazole-5-carboxylic acid (1-methyl-1H-indazol-6-yl)-amide

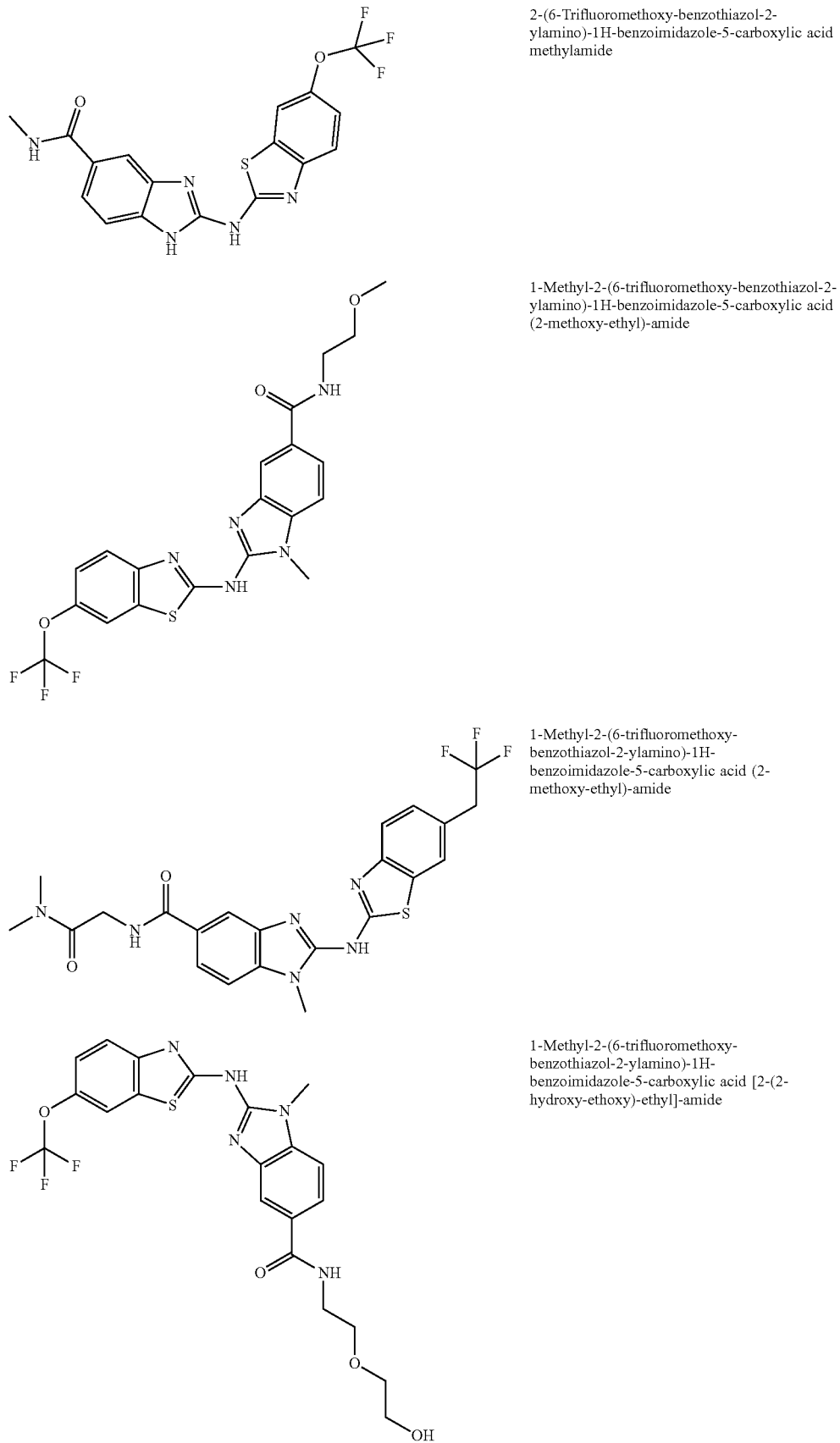

| | |
|---|---|
| | 2-(6-Trifluoromethoxy-benzothiazol-2-ylamino)-1H-benzoimidazole-5-carboxylic acid methylamide |
| | 1-Methyl-2-(6-trifluoromethoxy-benzothiazol-2-ylamino)-1H-benzoimidazole-5-carboxylic acid (2-methoxy-ethyl)-amide |
| | 1-Methyl-2-(6-trifluoromethoxy-benzothiazol-2-ylamino)-1H-benzoimidazole-5-carboxylic acid (2-methoxy-ethyl)-amide |
| | 1-Methyl-2-(6-trifluoromethoxy-benzothiazol-2-ylamino)-1H-benzoimidazole-5-carboxylic acid [2-(2-hydroxy-ethoxy)-ethyl]-amide |

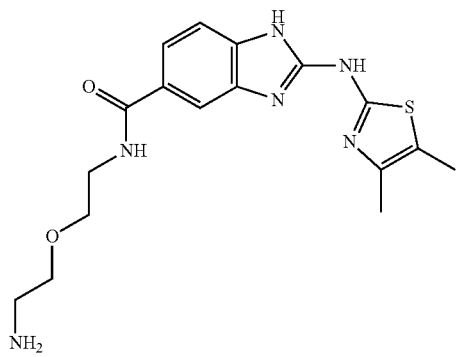 [SMILES: Cc1nc(Nc2nc3cc(C(=O)NCCOCCN)ccc3[nH]2)sc1C]
2-(4,5-Dimethyl-thiazol-2-ylamino)-1H-benzoimidazole-5-carboxylic acid [2-(2-amino-ethoxy)-ethyl]-amide
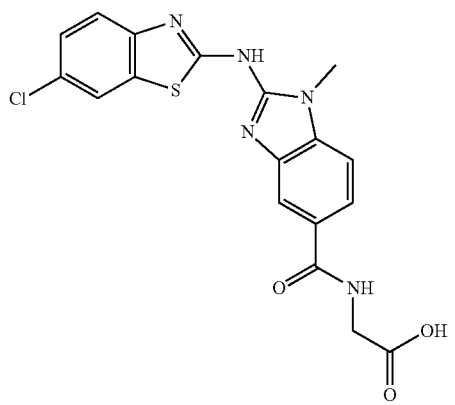 [SMILES: Cn1c(Nc2nc3ccc(Cl)cc3s2)nc2cc(C(=O)NCC(=O)O)ccc21]
{[2-(6-Chloro-benzothiazol-2-ylarnino)-1-methyl-1H-benzoimidazole-5-carbonyl]-amino}-acetic acid
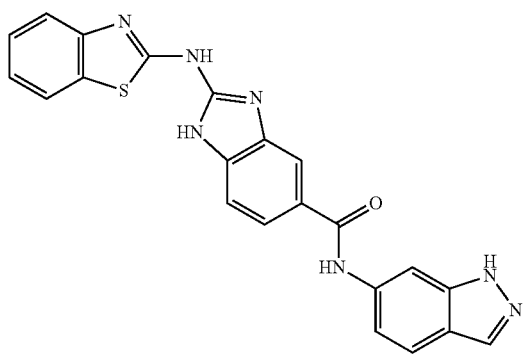 [SMILES: O=C(Nc1ccc2cn[nH]c2c1)c1ccc2[nH]c(Nc3nc4ccccc4s3)nc2c1]
2-(Benzothiazol-2-ylamino)-1H-benzoimidazole-5-carboxylic acid (1H-indazol-6-yl)-amide
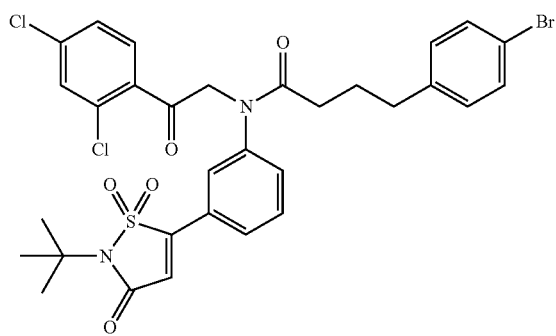 [SMILES: CC(C)(C)N1C(=O)C=C(c2cccc(N(CC(=O)c3ccc(Cl)cc3Cl)C(=O)CCCc3ccc(Br)cc3)c2)S1(=O)=O]
2-(4-Bromo-phenyl)-N-[3-(2-tert-butyl-1,1,3-trioxo-2,3-dihydro-1H-isothiazol-5-yl)-phenyl]-N-[2-(2,4-dichloro-phenyl)-2-oxo-ethyl]-acetamide

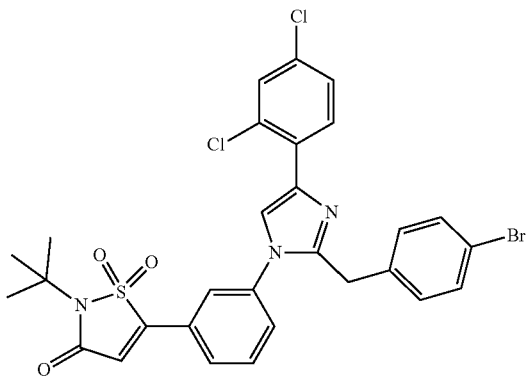 [SMILES: CC(C)(C)N1C(=O)C=C(c2cccc(-n3cc(-c4ccc(Cl)cc4Cl)nc3Cc3ccc(Br)cc3)c2)S1(=O)=O]

5-{3-[2-(4-Bromo-benzyl)-4-(2,4-dichloro-phenyl)-imidazol-1-yl]-phenyl}-2-tert-butyl-1,1-dioxo-1,2-dihydro-isothiazol-3-one In some embodiments, the BACH1 inhibitor comprises 2-(Benzothiazol-2-ylamino)-1H-benzoimidazole-5-carboxylic acid (1H-indazol-6-yl)-amide.

B. ETC Molecular Inhibitors

There are different "protein complexes" that comprise the electron transport chain. Electrons travel in sequence from their point of entry along the chain. The two points of entry along the electron transport chain are into Complex I and Complex II. NADH is oxidized at Complex I and $FADH_2$ is oxidized at Complex II.

Inhibitors of the Electron Transport Chain include substances that bind to some of the components of the ETC, blocking its ability to change in a reversible form from an oxidized state to a reduced state. Exemplary molecular ETC inhibitors are described below.

In some embodiments, the inhibitor is an inhibitor of complex I (NADH-coenzyme Q oxidoreductase), such as rotenone, chlorpromazine, piercidin A, amytal, metformin, or Demerol. In some embodiments, the inhibitor is an inhibitor of Complex II (succinate-Q oxidoreductase), such as 2-Thenoyltrifluroacetone, malonate, oxaloacetate, and Carboxin. In some embodiments, the inhibitor is an inhibitor of Complex III (Q-cytochrome c oxidoreductase), such as antimycin A1, napthoquinone, dimercaprol, phenformin, and myxothiazole. In some embodiments, the inhibitor is an inhibitor of Complex IV (cytochrome c oxidase), such as cyanide, azide, hydrogen sulfide, and carbon monoxide. In some embodiments, the inhibitor is an inhibitor of Complex V (ATP synthase) such as oligomycin A and diclyclohexylcarbodiimide. In some embodiments, the ETC inhibitor comprises a ATP/ADP translocase inhibitor such as atractyloside.

In some embodiments, the ETC inhibitor comprises metformin derivatives or a biguanide. Biguanides include, for example, N1-piperidine-N5-(3,5-dimethoxy)phenyl biguanide; N1-piperidine-N5-(4-fluoro-3-trifluoromethyl)phenyl biguanide; N1-piperidine-N5-(4-chloro-3-trifluoromethyl)phenyl biguanide; N1-pyrrolidine-N5-(3-fluoro-4-trifluoromethyl)phenyl biguanide; N1-piperidine-N5-(3-fluoro-4-trifluoromethyl)phenyl biguanide; N1-piperidine-N5-(4-fluoro-3-trifluoromethoxy)phenyl biguanide; N1-piperidine-N5-(4-chloro-3-trifluoromethoxy)phenyl biguanide; N1-azetidine-N5-(3-fluoro-4-trifluoromethoxy)phenyl biguanide; N1-pyrrolidine-N5-(3-fluoro-4-trifluoromethoxy)phenyl biguanide; N1-piperidine-N5-(3-fluoro-4-trifluoromethoxy)phenyl biguanide; N1-azetidine-N5-(3-chloro-4-trifluoromethoxy)phenyl biguanide; N1-pyrrolidine-N5-(3-chloro-4-trifluoromethoxy)phenyl biguanide; N1-piperidine-N5-(3-chloro-4-trifluoromethoxy)phenyl biguanide; N1-piperidine-N5-(2,4-difluoro)phenyl biguanide; N1-piperidine-N5-(3,4-difluoro)phenyl biguanide; N1-piperidine-N5-(3,5-difluoro)phenyl biguanide; N1-piperidine-N5-(3,5-dichloro)phenyl biguanide; N1-piperidine-N5-(2,4-dichloro)phenyl biguanide; N1-pyrrolidine-N5-(3,4-dichloro)phenyl biguanide; N1-piperidine-N5-(3,4-dichloro)phenyl biguanide; N1-piperidine-N5-(3-chloro-5-trifluoromethoxy)phenyl biguanide; N1-pyrrolidine-N5-(3-bromo-5-trifluoromethoxy)phenyl biguanide; N1-piperidine-N5-(3-bromo-5-trifluoromethoxy)phenyl biguanide; N1-piperidine-N5-(3,4,5-trifluoro)phenyl biguanide; or N1-piperidine-N5-(2,4,6-trifluoro)phenylbiguanide.

Exemplary metformin derivatives include N-(3,5-diimino-2-methyl-7-thia-2,4,6-triazanonan-9-yl)acetamide; 3,5-diimino-2,17,17-trimethyl-11,15-dioxo-7-thia-2,4,6,10,14-pentaazaoctadecane-16,18-diyl diacetate; and A/-(3,5-diimino-2-methyl-11-oxo-7-thia-2,4,6,10-tetraazatridecan-13-yl)-2,4-dihydroxy-3,3-dimethylbutanamide. In some embodiments, the ETC inhibitor comprises HL010183.

C. Inhibitory Antibodies

In certain embodiments, an antibody or a fragment thereof that binds to at least a portion of the BACH1 protein and inhibits BACH1 activity and/or function is used in the methods and compositions described herein.

In some compositions, the anti-BACH antibody is a monoclonal antibody or a polyclonal antibody. In some embodiments, the antibody is a chimeric antibody, an affinity matured antibody, a humanized antibody, or a human antibody. In some embodiments, the antibody is an antibody fragment. In some embodiments, the antibody is a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb"

fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with a BACH1 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g., mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091, 513, and 6,881,557, which are incorporated herein by this reference.

By known means as described herein, polyclonal or monoclonal antibodies, binding fragments and binding domains and CDRs (including engineered forms of any of the foregoing), may be created that are specific to BACH1 protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to BACH1 will have the ability to neutralize or counteract the effects of the BACH1 regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

In some embodiments, the inhibitor is a peptide, polypeptide, or protein inhibitor. In some embodiments, the inhibitor is an antagonistic antibody.

In some embodiments, the ETC inhibitor is a biogenesis inhibitor and/or is used in the place of an ETC inhibitor in the methods and compositions of the disclosure.

D. Nucleic Acid Inhibitors

Inhibitory nucleic acids or any ways of inhibiting gene expression of BACH1 known in the art are contemplated in certain embodiments. Examples of an inhibitory nucleic acid include but are not limited to siRNA (small interfering RNA), short hairpin RNA (shRNA), double-stranded RNA, an antisense oligonucleotide, a ribozyme, and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, a siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids for BACH1 are known in the art, such as those described in US20120016010, which is herein incorporated by reference. These include, for example, the following siRNAs: 5'-GGAAUCCUGCUUUCAGUUU-3' (SEQ ID NO:1); 5'-AAACUGAAAGCAGGAUUCC-3' (SEQ ID NO:2); 5'-GUCUGAGUGUCCGUGGUUA-3' (SEQ ID NO:3); 5'-UAACCACGGACACUCAGAC-3' (SEQ ID NO:4); 5'-GCAGUUACUUCCACUCAAG-3' (SEQ ID NO:5); 5'-CUUGAGUGGAAGUAACUGC-3' (SEQ ID NO:6); 5'-CUACACUGCUAAACUGAUU-3' (SEQ ID NO:7); 5'-AAUCAGUUUAGCAGUGUAG-3' (SEQ ID NO:8); 5'-GAUUUGCAGGUGAUGUUAA-3' (SEQ ID NO:9); 5"-UUAACAUCACCUGCAAAUC-3 (SEQ ID NO:10)'; 5'-AUUUGAACCUUUAAUUCAG-3' (SEQ ID NO:11); 5'-CUGAAUUAAAGGUUCAAAU-3' (SEQ ID NO:12); 5'-GUUAAAGGAUUUGAACCUU-3' (SEQ ID NO:13); and 5'-AAGGUUCAAAUCCUUUAAC-3' (SEQ ID NO:14). In some embodiments, the nucleic acid inhibitor is comprises a modification, such as a chemical modification or a modified base. In some embodiments, one or more (e.g., 1, 2, 3, 4, 5, 6, 7, 8, 9, 10, 11, 12, 13, 14, 15, 16, 17, 18, 19.20, 21, 22, 23, 24, 25, 26, 27, 28, 29, 30, 31, 32, 33, 34, 35, 36, 37, 38, 39, or 40 (or any derivable range therein) of the nucleotide positions in one or both strands of an siRNA molecule are modified. Modifications include nucleic acid sugar modifications, base modifications, backbone (internucleotide linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In other instances, at least one modified nucleotide is a 2'-deoxy-2'-fluoro nucleotide, a 2'-deoxy nucleotide, or a 2'-O-alkyl nucleotide. In certain embodiments, the siRNA molecule has 3' overhangs of one, two, three, or four nucleotide(s) on one or both of the strands. In other embodiments, the siRNA lacks overhangs (i.e., has blunt ends). The overhangs can be modified or unmodified. Examples of modified nucleotides in the overhangs include, but are not limited to, 2'-O-alkyl nucleotides, 2'-deoxy-2'-fluoro nucleotides, or 2'-deoxy nucleotides. The overhang nucleotides in the antisense strand can comprise nucleotides that are complementary to nucleotides in the Bach1 target sequence. Likewise, the overhangs in the sense stand can comprise nucleotides that are in the Bach1 target sequence. In certain instances, the siRNA molecules have two 3' overhang nucleotides on the antisense stand that are 2'-O-alkyl nucleotides and two 3' overhang nucleotides on the sense stand that are 2'-deoxy nucleotides.

Particularly, an inhibitory nucleic acid may be capable of decreasing the expression of BACH1 by at least 10%, 20%, 30%, or 40%, more particularly by at least 50%, 60%, or 70%, and most particularly by at least 75%, 80%, 90%, 95% or more or any range or value in between the foregoing.

In further embodiments, there are synthetic nucleic acids that are BACH1 inhibitors. An inhibitor may be between 17 to 25 nucleotides in length and comprises a 5' to 3' sequence that is at least 90% complementary to the 5' to 3' sequence of a mature BACH1 mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature BACH1 mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA. Nucleic acid inhibitors such as BACH1 siRNA, shRNA and lentiviral particle gene silencers are commercially available and are useful in the methods and compositions of the current disclosure. For example, BACH1 siRNA (Cat # sc-37064), BACH1 shRNA (Cat # sc-37064-SH), and BACH1 shRNA lentiviral particles (Cat # sc-37064-V) are all available commercially from Santa Cruz Biotechnology.

Since the sequence of BACH1 is known (the human sequence of BACH1 is provided below), one skilled in the art can easily design and test various nucleic acid inhibitors that are useful in the methods and compositions of the disclosure. The sequence for the human BACH1 protein is:

mslsensvfa yessvhstnv llslndqrkk dvlcdvtifv egqrfrahrs vlaacssyfh srivgqadge lnitlpeevt vkgfepliqf aytaklilsk envdevckcv eflsvhniee scfqflkfkf ldstadqqec prkkcfsshc qktdlklsll dqrdletdev eeflenknvq tpqcklrryq gnakaspplq dsasqtyesm clekdaalal pslcpkyrkf qkafgtdrvr tgessvkdih asvqpnerse neclggvpec rdlqvmlkcd esklamepee tkkdpasqcp teksevtpfp hnssidphgl yslsllhtyd qygdlnfagm qnttvltekp lsgtdvqekt fgesqdlplk sdlgtredss vassdrssve revaehlakg fwsdicstdt pcqmqlspav akdgseqisq krsecpwlgi risespepgq rtftlssvn cpfistlste gcssnleign ddyvsepqqe pcpyacvisl gdd-setdteg dsescsareq ecevklpfna qriissrnd fqsllkmhk tpeqldcihd irrrsknria aqrcrkrkld ciqnleseie klqsekesll ker-dhilstl getkqnltgl cqkvckeaal sqeqiqilak ysaadcplsf lisekdk-stp dgelalpsif slsdrppavl ppcargnsep gyargqesqq mstatseqag paeqcrqsgg isdfcqqmtd kcttde. (SEQ ID NO:15)

E. Chemotherapeutic Agents and Other Additional Therapeutic Agents

Certain embodiments of the disclosure relate to the administration of one or more additional therapeutics. The additional therapeutic may be an agent described herein or a treatment method described herein.

In some embodiments, the additional agent comprises a BCL2 inhibitor. Exemplary BCL2 inhibitors include, for example, ABT-737, ABT-263 (navitoclax), ABT-199 (venetoclax, RG7601, GDC-0199), Gambogic Acid, 2,3-DCPE, gossypol, (–)-Epigallocatechin Gallate, Nilotinib, AG 1024, HA14-1, Obatoclax Mesylate, Piperlongumine, TW-37, EM20-25, YC137, Genasense, and oblimersen sodium/

Further Bcl2 inhibitors include N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide; N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide; 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide; 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide; N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(H-indazol-4-yloxy)benzamide; N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide; 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide; N-((3-chloro-4-[(4-fluorotetrahydro-2H-pyran-4-yl)methoxy]phenyl)sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-[2-(4-chlorophenyl)-4,4-dimethylcyclohex-1-en-1-yl]methyl)piperazin-1-yl)-N-({5-fluoro-6-[(4-fluorotetrahydro-2H-pyran-4-yl)methoxy]pyridin-3-yl}sulfonyl)-2-(H-indazol-4-yloxy)benzamide; 4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide; Trans-2-[(6-amino-5-chloropyridin-3-yl)oxy]-4-(4-([2-(4-chlorophenyl)-4,4-dimethylcyclohex-1-en-1-yl]methyl)piperazin-1-yl)-N-({4-[(4-morpholin-4-ylcyclohexyl)amino]-3-nitrophenyl}sulfonyl)benzamide; 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(H-pyrrolo[2,3-b]pyridin-5-yloxy)benzamide; Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; N-((5-chloro-6-[(trans-4-hydroxycyclohexyl)methoxy]pyridin-3-yl)sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[trans-4-(morpholin-4-yl)cyclohexyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-({[(cis-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide; N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; 4-(4-([2-(4-chlorophenyl)-4,4-dimethylcyclohex-1-en-1-yl]methyl)piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino)-3-nitrophenyl)sulfonyl]-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide; N-((5-chloro-6-[(trans-4-hydroxy-4-methylcyclohexyl)methoxy]pyridin-3-yl)sulfonyl)-4-(4-([2-(4-chlorophenyl)-4,4-dimethylcyclohex-1-en-1-yl]methyl)piperazin-1-yl)-2-(H-indazol-4-yloxy)benzamide; N-({5-chloro-6-[(cis-1-fluoro-4-hydroxy-4-methylcyclohexyl)methoxy]pyridin-3-yl}sulfonyl)-4-(4-([2-(4-chlorophenyl)-4,4-dimethylcyclohex-1-en-1-yl]methyl)piperazin-1-yl)-2-(1H-indazol-4-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-([(4-methoxycyclohexyl)methyl]amino)-3-nitrophenyl)sulfonyl]benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-([2-(4-chlorophenyl)-4,4-dimethylcyclohex-1-en-1-yl]methyl)piperazin-1-yl)-N-[(4-([(trans-4-hydroxy-4-methylcyclohexyl)methyl]amino)-3-nitrophenyl)sulfonyl]-2-(1H-pyrrolo[2,3-b]pyridin-5-yloxy)benzamide; 2-[(3-amino-1H-indazol-4-yl)oxy]-4-(4-{[2-(4-chlorophenyl)-4,4-dimethylcyclohex-1-en-1-yl]methyl}piperazin-1-yl)-N-[(4-{[(trans-4-methoxycyclohexyl)methyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-44 {[4-(oxetan-3-yl)morpholin-2-yl]methyl}amino)phenyl]sulfonyl}benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-[0-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide; N-((5-chloro-6-[(trans-4-hydroxy-4-methylcyclohexyl)methoxy]pyridin-3-yl)sulfonyl)-2-[(3-chloro-1H-indazol-4-yl)oxy]-4-(4-([2-(4-chlorophenyl)-4,4-dimethylcyclohex-1-en-1-yl]methyl)piperazin-1-yl)benzamide; 4-[4-{[2-(4-chlorophenyl)-4,4-dimethylcyclohex-1-en-1-yl]methyl}(2H8)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({5-chloro-6-[(trans-1-fluoro-4-hydroxy-4-methylcyclohexyl)methoxy]pyridin-3-yl}sulfonyl)-4-(4-([2-(4-chlorophenyl)-4,4-dimethylcyclohex-1-en-1-yl]methyl)piperazin-1-yl)-2-(1H-pyrrolo[2,3-b]pyridin-5-yloxy)benzamide; 4-(4-([2-(4-chlorophenyl)-4,4-dimethylcyclohex-1-en-1-yl]methyl)piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide; 4-(4-([2-(4-chlorophenyl)-4,4-dimethylcyclohex-1-en-1-yl]methyl)piperazin-1-yl)-N-((5-nitro-6-[(tetrahydro-2H-pyran-4-ylmethyl)amino]pyridin-3-yl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide; and 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide.

The methods and compositions may include chemotherapy, therapeutic agents, hormonal therapy, surgical removal of the breast and/or ovaries, trastuzumab, and radiation therapy. In some aspects, the treatment regimen (treatment for patients having or predicted to have non-metastatic cancer) excludes one or more of chemotherapy, therapeutic agents, hormonal therapy, surgical removal of the breast and/or ovaries, trastuzumab, and radiation therapy.

Chemotherapeutic agents include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, famesyl-protein transferase inhibitors, transplatinum, 5-fluorouracil, vincristin, vinblastin and methotrexate, or any analog or derivative variant of the foregoing.

Suitable therapeutic agents include, for example, *vinca* alkaloids, agents that disrupt microtubule formation (such as colchicines and its derivatives), anti-angiogenic agents, therapeutic antibodies, RKIP pathway targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), albumin-bound paclitaxel, thiotepa, vincristine, liposomal doxorubicin, vinorelbine.

In some embodiments, the chemotherapeutic agent is any of (and in some embodiments selected from the group consisting of) aromatase inhibitor, toremifene, magestrol acetate, fluvestran, trastuzumab, docetaxel, liposomal doxorubicin, ixabepilone, albumin-bound paclitaxel, eribulin, adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, HERCEPTIN® (trastuzumab), vinorelbine, DOXIL® (doxorubicin), capecitabine, GLEEVEC® (imatinib), ALIMTA® (pemetrexed), AVASTIN® (bevacizumab) VELCADE® (bortezomib), TARCEVA® (erlotinib), NEULASTA® (pefilgrastim), Lapatinib, STI-571, ZD1839, IRESSA® (gefitinib), SH268, genistein, CEP2563, SU6668, SU11248, EMD121974, and Sorafenib.

In some embodiments, the treatment regimen is a combination of the one or more chemotherapeutic agents described herein. In some embodiments, the treatment regimen excludes one or more of the chemotherapeutic agents described herein.

In further embodiments a combination of therapeutic treatment agents is administered to cancer cells. The therapeutic agents may be administered serially (within minutes, hours, or days of each other) or in parallel; they also may be administered to the patient in a pre-mixed single composition. Combinations of cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol).

Various combinations of more than an anticancer modality, agent or compound (or a combination of such agents and/or compounds) may be employed, for example, a first anticancer modality, agent or compound is "A" and a second anticancer modality, agent or compound (or a combination of such modalities, agents and/or compounds) given as part of an anticancer therapy regime, is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Alternative cancer therapy include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy. A therapeutic polynucleotide may be administered before, after, or at the same time of a first cancer therapy. Delivery of a vector encoding a variety of proteins is encompassed in certain aspects. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with treatment methods described herein to improve the anti-hyperproliferative efficacy of the treatments. Inhibitors of cell adhesion are contemplated to improve the efficacy. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with treatment methods described herein to improve the treatment efficacy.

Hormonal therapy may also be used or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

III. METHODS OF TREATMENT

A. Treatment of Cancer

Certain embodiments are directed to methods of treating cancer, such as breast cancer, based on the expression level of BACH1. Any known treatments that are contemplated for treating a cancer, breast cancer, or TNBC can be used (for example, see Andre et al., 2012, which is incorporated herein by reference in its entirety)

In certain aspects, there may be provided methods for treating a subject determined to have cancer and with a predetermined expression profile of one or more biomarkers disclosed herein.

In a further aspect, biomarkers and related systems that can establish a prognosis of cancer patients can be used to identify patients who may get benefit of conventional single or combined modality therapy. In the same way, those patients who do not get much benefit from such conventional single or combined modality therapy can be identified and can be offered alternative treatment(s).

Approximately 60% of persons with cancer will undergo surgery of some type, which includes preventative, diagnostic or staging, curative and palliative surgery. Curative surgery is a cancer treatment that may be used in conjunction with other therapies, such as the treatment, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

In some embodiments, the methods may further comprise a therapy described herein such as those described below.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

The cancers amenable for treatment include, but are not limited to, tumors of all types, locations, sizes, and characteristics. In some embodiments, the cancer is a breast cancer. In some embodiments, the breast cancer is triple negative breast cancer (TNBC). The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma, squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

B. ROC Analysis

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1−specificity). The ROC curve is thus the sensitivity as a function of fall-out. In general, if the probability distributions for both detection and false alarm are known, the ROC curve can be generated by plotting the cumulative distribution function (area under the probability distribution from − infinity to + infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC curve was first developed by electrical engineers and radar engineers during World War II for detecting enemy objects in battlefields and was soon introduced to psychology to account for perceptual detection of stimuli. ROC analysis since then has been used in medicine, radiology, biometrics, and other areas for many decades and is increasingly used in machine learning and data mining research.

The ROC is also known as a relative operating characteristic curve, because it is a comparison of two operating characteristics (TPR and FPR) as the criterion changes. ROC analysis curves are known in the art and described in Metz C E (1978) Basic principles of ROC analysis. Seminars in Nuclear Medicine 8:283-298; Youden W J (1950) An index for rating diagnostic tests. Cancer 3:32-35; Zweig M H, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

ROC analysis is useful for determining cut-off values for expression levels, protein levels, or activity levels. Such cut-off values can be used to determine a patient's prognosis and to predict a patient's response to a particular therapy.

C. Biological Sample Preparation

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is breast tissue. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example breast) and one or more samples from another tissue may be obtained for diagnosis by the methods. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

IV. ANALYSIS OF GENE EXPRESSION

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous tissue cells or a heterogeneous population of cancers.

Comparison of multiple marker genes with a threshold level can be performed as follows: 1. The individual marker genes are compared to their respective threshold levels. 2. The number of marker genes, the expression level of which is above their respective threshold level, is determined. 3. If a marker genes is expressed above its respective threshold level, then the expression level of the marker gene is taken to be "above the threshold level".

In certain aspects, the determination of expression levels is on a gene chip, such as an Affymetrix™ gene chip. In another aspect, the determination of expression levels is done by kinetic real time PCR.

In certain aspects, the methods can relate to a system for performing such methods, the system comprising (a) apparatus or device for storing data on the receptors status (ER, AR, or PR, GR) or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second, third, fourth, $5^{th}$, $6^{th}$ or more marker gene or activity and for comparing with a corresponding predetermined threshold; and (e) computing apparatus or device programmed to provide a unfavorable or poor prognosis or favorable prognosis based on the comparisons.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different cancer biomarkers. Other suitable measures or indicators can also be employed for assessing the relationship or difference between different expression patterns.

The expression levels of cancer biomarkers can be compared to reference expression levels using various methods. These reference levels can be determined using expression levels of a reference based on all cancer patients. Alternatively, it can be based on an internal reference such as a gene that is expressed in all cells. In some embodiments, the reference is a gene expressed in cancer cells at a higher level than any biomarker. Any comparison can be performed using the fold change or the absolute difference between the expression levels to be compared. One or more cancer biomarkers can be used in the comparison. It is contemplated that 1, 2, 3, 4, 5, 6, 7, 8, 9, 10, and/or 11 biomarkers (or any range derivable therein) may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are with normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein. In some embodiments, the levels can be relative to a non-metastatic control or relative to a metastatic control.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments.

Any biological sample from the patient that contains cancer cells may be used to evaluate the expression pattern of any biomarker discussed herein. In some embodiments, a biological sample from a tumor is used. Evaluation of the sample may involve, though it need not involve, panning (enriching) for cancer cells or isolating the cancer cells.

A. Measurement of Gene Expression Using Nucleic Acids

Testing methods based on differentially expressed gene products are well known in the art. In accordance with one aspect, the differential expression patterns of cancer biomarkers can be determined by measuring the levels of RNA transcripts of these genes, or genes whose expression is modulated by the these genes, in the patient's cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding cancer biomarkers include those that are identical or complementary to all or part of the cancer biomarker genes described herein. These sequences are all nucleic acid sequences of cancer biomarkers.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used to increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene described herein. Particularly, each probe/primer has relatively high sequence complexity and does not have any ambiguous residue (undetermined "n" residues). The probes/primers can hybridize to the target gene, including its RNA transcripts, under stringent or highly stringent conditions. In some embodiments, because each of the biomarkers has more than one human sequence, it is contemplated that probes and primers may be designed for use with each of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable cDNAs may be normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of cancer biomarkers in cancer cells. The probes suitable for detecting the corresponding cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm2.

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods and the arrays are not limited in its utility with respect to any parameter except that the probes detect expression levels; consequently, methods and compositions may be used with a variety of different types of genes. In some examples, the microarray is a tissue microarray which contains many small representative tissue samples from hundreds of different cases assembled on a single histologic slide, and allows high throughput analysis of multiple specimens at the same time (Wilczynski Modern Surgical Pathology $2^{nd}$ Edition 2009).

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per cm2. The surface area of the array can be about or less than about 1, 1.6, 2, 3, 4, 5, 6, 7, 8, 9, or 10 cm2.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Measurement of Gene Expression Using Proteins and Polypeptides

In other embodiments, the differential expression patterns of cancer biomarkers can be determined by measuring the levels of polypeptides encoded by these genes in cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the cancer biomarker genes described herein.

One example of a method suitable for detecting the levels of target proteins in peripheral blood samples is ELISA. In an exemplifying ELISA, antibodies capable of binding to the target proteins encoded by one or more cancer biomarker genes are immobilized onto a selected surface exhibiting protein affinity, such as wells in a polystyrene or polyvinylchloride microtiter plate. Then, cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the cancer cell samples containing the target proteins are immobilized onto the well surface and then contacted with the antibodies. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radio-labeled-polypeptides and unlabeled polypeptides for binding to a limited quantity of antibodies. Suitable radiolabels include, but are not limited to, $I^{125}$. In one embodiment, a fixed concentration of $I^{25}$-labeled polypeptide is incubated with a series of dilution of an antibody specific to the polypeptide. When the unlabeled polypeptide is added to the system, the amount of the $I^2$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in cancer cell samples are well known in the art.

Suitable antibodies include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

The analyses of gene expression in human breast cancer tumor databases suggest that ~80% of ER− tumors express low levels of BACH1 and therefore would likely benefit from metformin, whereas ~40% of TNBC patients have high BACH1 levels and would likely be resistant to metformin therapy. A tumor microarray (TMA) based assay which can combine protein immunohistochemistry and gene expression analyses, can rapidly screen patients' tissues of multiple patients, enabling rapid stratification of patients according to BACH1/ETC expression. This prescreening methodology can be used for diagnosis, prognosis and ultimately treatment of breast cancer patients including high risk TNBCs.

V. PHARMACEUTICAL COMPOSITIONS

In certain aspects, the compositions or agents for use in the methods, such as therapeutic agents or inhibitors, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices, local administration, and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antgifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VI. KITS

Certain aspects of the present disclosure also concern kits containing compositions of the disclosure or compositions to implement methods of the disclosure. In some embodiments, kits can be used to evaluate one or more nucleic acid and/or polypeptide molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, synthetic RNA molecules or inhibitors, or any value or range and combination derivable therein. In some embodiments, there are kits for evaluating gene expression, protein expression, or protein activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide detecting agents, and/or inhibitors or antagonists of the disclosure for prognostic, diagnostic, or drug screening applications are included. Specifically contemplated are any such molecules corresponding to any nucleic acid or polypeptide identified herein.

In certain aspects, negative and/or positive control agents are included in some kit embodiments. The control molecules can be used to verify transfection efficiency and/or control for transfection-induced changes in cells.

Embodiments of the disclosure include kits for analysis of a pathological sample by assessing a nucleic acid or polypeptide profile for a sample comprising, in suitable container means, two or more RNA probes, or a polypeptide detecting agent, wherein the RNA probes or polypeptide detecting agent detects nucleic acids or polypeptides described herein. Furthermore, the probes, detecting agents and/or inhibiting reagents may be labeled. Labels are known in the art and also described herein. In some embodiments, the kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye. Certain aspects also encompass kits for performing the diagnostic or therapeutic methods. Such kits can be prepared from readily available materials and reagents. For example, such kits can comprise any one or more of the following materials: enzymes, reaction tubes, buffers, detergent, primers, probes, antibodies. In a particular embodiment, these kits allow a practitioner to obtain samples of neoplastic cells in breast, blood, tears, semen, saliva, urine, tissue, serum, stool, sputum, cerebrospinal fluid and supernatant from cell lysate. In another particular embodiment, these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Effective Combination Therapy Targeting BACH1 and Oxidative Phosphorylation for Triple-Negative Breast Cancer To examine other potential functions of BACH1 in TNBC, microarrays of metastatic MDA-MB-231-derived cells (BM1; also termed 1833) expressing shRNA were analyzed for BACH1 (BM1-shBACH1) or control vector (BM1-shCont). Gene set enrichment analysis (GSEA) identified a significant increase in metabolic pathways including energy metabolism and mitochondrial inner membrane genes upon BACH1 depletion (shown in FIG. 1B-C of U.S. Provisional Application No. 62/517,626, which is incorporated by reference). The inventors validated induction of genes enriched in the mitochondrial inner membrane by quantitative RT-PCR using two TNBC cell lines stably knocked down with BACH1 shRNA, BM1 and MDA-MB-436 (MB436), as well as MDA-MB-231 cells transiently expressing BACH1 siRNA (shown in FIG. 1D, FIG. 5C-D of U.S. Provisional Application No. 62/517,626, which is incorporated by reference). To determine whether mitochondrial genes are direct BACH1 targets, potential BACH1 recruitment sites (MAF recognition element, MARE; TGCTGAG/CTCAT/C (SEQ ID NO: 106)) within the promoter regions of these genes were analyzed. Having identified potential BACH1 binding sites for three ETC genes, COX15, ATP5C, and UQCRC1 (shown in FIG. 1E of U.S. Provisional Application No. 62/517,626, which is incorporated by reference), chromatin immunoprecipitation (ChIP) assays with BACH1 antibody using control or shBACH1 cells were performed; Heme oxygenase 1 (HMOX1) served as a positive control (shown in FIG. 5E of U.S. Provisional Application No. 62/517,626, which is incorporated by reference). The inventors observed a striking enrichment of BACH1 bound to the promoter regions of these three mitochondrial membrane genes (shown in FIG. 1F of U.S. Provisional Application No. 62/517,626, which is incorporated by reference).

To examine other potential functions of BACH1 in TNBC, microarrays of metastatic MDA-MB-231-derived cells (BM1; also termed 1833) expressing shRNA were analyzed for BACH1 (BM1-shBACH1) or control vector (BM1-shCont). Gene set enrichment analysis (GSEA) identified a significant increase in metabolic pathways including energy metabolism and mitochondrial inner membrane genes upon BACH1 depletion (shown in FIG. 1B-C of U.S. Provisional Application No. 62/517,626, which is incorporated by reference). The inventors validated induction of genes enriched in the mitochondrial inner membrane by quantitative RT-PCR using two TNBC cell lines stably knocked down with BACH1 shRNA, BM1 and MDA-MB-436 (MB436), as well as MDA-MB-231 cells transiently expressing BACH1 siRNA (shown in FIG. 1D, FIG. 5C-D of U.S. Provisional Application No. 62/517,626, which is incorporated by reference). To determine whether mitochondrial genes are direct BACH1 targets, potential BACH1 recruitment sites (MAF recognition element, MARE; TGCTGAG/CTCAT/C) within the promoter regions of these genes were analyzed. Having identified potential BACH1 binding sites for three ETC genes, COX15, ATPC, and UQCRC1 (shown in FIG. 1E of U.S. Provisional Application No. 62/517,626, which is incorporated by reference), chromatin immunoprecipitation (ChIP) assays with BACH1 antibody using control or shBACH1 cells were performed; Heme oxygenase 1 (HMOX1) served as a positive control (shown in FIG. 5E of U.S. Provisional Application No. 62/517,626, which is incorporated by reference). The inventors observed a striking enrichment of BACH1 bound to the promoter regions of these three mitochondrial membrane genes (shown in FIG. 1F of U.S. Provisional Application No. 62/517,626, which is incorporated by reference).

It was determined whether the changes in ETC gene expression affect metabolic phenotypes in breast cancer cells by measuring both oxygen consumption rates (OCR), an indication of aerobic respiration, and extracellular acidification rates (ECAR), a readout of lactic acid produced from increased glycolysis, using a Seahorse XFe96 analyzer. TNBC cells (BM1 or MB436) depleted of BACH1 displayed increased basal OCR as well as maximum OCR but decreased ECAR relative to the control (shown in FIGS. 1G and 5F of U.S. Provisional Application No. 62/517,626, which is incorporated by reference). In addition, mass spectrometry analysis of metabolites identified increased levels of tricarboxylic acid (TCA) cycle intermediates such as citrate and oxaloacetate as well as ATP upon BACH1 knockdown (shown in FIG. 1G of U.S. Provisional Application No. 62/517,626, which is incorporated by reference). To explain the increased flow of pyruvate into the TCA cycle, it was asked whether there was a corresponding increase in expression of the gene for pyruvate dehydrogenase (PDH), the enzyme that initiates the conversion of pyruvate to acetyl-coA thereby connecting glycolysis and the TCA cycle. Not only were PDHB mRNA levels induced, but the mRNA and protein levels of the PDH inhibitor, pyruvate dehydrogenase kinase (PDK1, PDK2), were reduced in BACH1-depleted xenograft tumors as well as cultured cells (shown in FIG. 5H of U.S. Provisional Application No. 62/517,626, which is incorporated by reference). In addition, key cellular metabolic and bioenergetics parameters such as produced lactate levels, NADH/NAD$^+$ ratio, and glucose consumption were reduced in BACH1-depleted cells (shown in FIG. 5I-K of U.S. Provisional Application No. 62/517,626, which is incorporated by reference). Together, these results indicate that highly glycolytic breast cancer cells shift their metabolism from aerobic glycolysis to primarily oxidative respiration upon BACH1 depletion by targeting key regulatory steps.

Bioinformatic analysis of TCGA breast cancer patient data provided additional support for these findings. KEGG analysis of genes that negatively correlate with BACH1 expression (Spearman<−0.3) in TNBC as well as all combined breast cancer patient data showed a marked enrichment of oxidative phosphorylation (ETC) genes (shown in FIG. 1H, of U.S. Provisional Application No. 62/517,626, which is incorporated by reference). Furthermore, expression of the ETC genes ATP5C and UQCRC1 inversely correlated with BACH1 expression (Spearman≤−0.4) in all breast cancer patients (shown in FIG. 1E of U.S. Provisional Application No. 62/517,626, which is incorporated by reference).

Since BACH1 depletion shifts tumor cells to oxidative phosphorylation as a source of energy and biosynthetic precursors, the cells should have increased sensitivity to agents that target these pathways. Pharmacokinetic studies of metformin as a cancer drug suggest that it directly inhibits mitochondrial ETC complex I, activates the AMP-activated protein kinase (AMPK) pathway, and regulates pathways involved in nucleotide metabolism, redox and energy status, as well as mitochondrial metabolism. To determine whether the survival of TNBC cells is compromised by treatment with respiratory inhibitors, cell viability was monitored after treatment with metformin, rotenone, or antimycin A. BACH1-depleted cells had a higher sensitivity to inhibitors and significantly reduced cell viability upon treatment with ETC inhibitors relative to control cells using both calcein AM assays and confluency measurements (shown in FIG. 2A and 6A-C of U.S. Provisional Application No. 62/517, 626, which is incorporated by reference). Notably, MB436 cells are more sensitive to metformin than BM1 cells, illustrating the variability in breast cancer cell sensitivity to metformin. Importantly, metformin did not alter the viability of non-malignant mammary epithelial cells, whereas rotenone reduced cell viability by 25-50% (shown in FIG. 6D of U.S. Provisional Application No. 62/517,626, which is incorporated by reference). Since metformin is less toxic for non-malignant epithelial cells, metformin was used for further studies.

ETC Complex I generates cellular $NAD^+$ levels needed for metabolic processes such as synthesis of aspartic acid, an essential building block in cancer cell macromolecular biosynthesis, and metformin depletes $NAD^+$ levels. Consistent with previous findings, addition of pyruvate (2.5 mM) to the growth media increased $NAD^+$ levels and completely rescued the inhibitory effect of metformin (shown in FIG. 2B of U.S. Provisional Application No. 62/517,626, which is incorporated by reference), suggesting that Complex I is the primary target of metformin in the TNBC cells. Notably, expression of the organic cation transporter (OCT1), a metformin transporter, was not altered by BACH1 depletion as shown by microarrays and qRT-PCR (shown in FIG. 6E of U.S. Provisional Application No. 62/517,626, which is incorporated by reference), indicating the metformin transporter was not responsible for the increased sensitivity. Since mitochondrial ETC genes were induced in BACH1 depleted cells, the inventors assessed whether these genes are required for metformin sensitivity. Silencing of COX15 or UQCRC1 using siRNA in BM1-shBACH1 cells completely restored metformin resistance and rescued cell growth (shown in FIG. 2C and 6F-H of U.S. Provisional Application No. 62/517,626, which is incorporated by reference). Together, these results demonstrate that BACH1 depletion increases mitochondrial ETC gene expression and respiration in TNBC cells, thereby enhancing sensitivity to ETC inhibitor treatment.

To leverage the increased sensitivity of BACH1 knockdown cells to metformin, the inventors utilized hemin, the active ingredient of the FDA-approved drug panhematin used for acute porphyria, as an alternative means of depleting BACH1. Heme binding to BACH1 causes BACH1 ubiquitylation and degradation in the cytoplasm. Cultured TNBC cells were treated with 20 μM hemin, a dose that is neither cytotoxic nor growth inhibitory yet is still effective at reducing BACH1 levels (shown in FIG. 3A and 7A-B of U.S. Provisional Application No. 62/517,626, which is incorporated by reference). Hemin increased mitochondrial gene expression as well as HMOX1, similar to the induction observed upon genetic depletion of BACH1 (shown in FIG. 3B and 7C-D of U.S. Provisional Application No. 62/517, 626, which is incorporated by reference). In addition, hemin treatment altered cellular metabolic phenotypes, inducing higher maximum OCR but lower ECAR consistent with genetic deletion of BACH1 (shown in FIGS. 3C and 7E of U.S. Provisional Application No. 62/517,626, which is incorporated by reference). As anticipated, upon subsequent treatment with ETC inhibitors including metformin, hemin exposure drastically decreased viability of TNBC cells such as BM1 (shown in FIGS. 3D and 7F of U.S. Provisional Application No. 62/517,626, which is incorporated by reference), MB436 and BT549 cells (shown in FIG. 7G-H of U.S. Provisional Application No. 62/517,626, which is incorporated by reference). These results indicate that pharmacological depletion of BACH1 using hemin mimics genetic knockdown of BACH1 for transcriptional regulation and metabolic phenotype.

Given the critical role of BACH1 in regulating sensitivity to ETC inhibitors in vitro, the inventors then tested whether BACH1 is a useful therapeutic target in vivo using several pre-clinical TNBC mouse models. Initially, BACH1-depleted xenograft TNBC tumors (MB436-shBACH1 and BM1-shBACH1) were treated with metformin (200-300 mg/kg) in drinking water when tumors reached a palpable size ($\sim$25 mm$^3$ in volume). BACH1 depletion did not alter tumor growth compared to control tumors, consistent with previous observations. Similarly, no effect on control tumor growth was seen with metformin alone (shown in FIG. 4A and 8A-B of U.S. Provisional Application No. 62/517,626, which is incorporated by reference). However, TNBC tumor growth that stably expressed shBACH1 was drastically suppressed within a week upon metformin administration (shown in FIG. 8C-D of U.S. Provisional Application No. 62/517,626, which is incorporated by reference). Moreover, a significant fraction of shBACH xenograft mice were tumor-free relative to the control (shown in FIG. 4B of U.S. Provisional Application No. 62/517,626, which is incorporated by reference).

It was then asked whether combination treatment using hemin and metformin is similarly effective. Initially, BACH1 expression in the mouse models was monitored by immunoblotting using tumor lysates (shown in FIG. 4C of U.S. Provisional Application No. 62/517,626, which is incorporated by reference). A transgenic TNBC mouse model, (C3(1)-TAg), had very low BACH1 expression whereas the BM1 xenograft and patient-derived xenograft (PDX) tumors expressed relatively high levels of BACH1. As predicted, the C3(1)-TAg mice were highly sensitive to metformin in the absence of hemin treatment (shown in FIG. 4D of U.S. Provisional Application No. 62/517,626, which is incorporated by reference). After determining the optimal dosing schedule for hemin degradation of BACH1 in tumors (shown in FIG. 8E-F of U.S. Provisional Application No. 62/517,626, which is incorporated by reference), MB436 xenograft mice were treated with hemin (50 mg/kg/day, i.p. consecutive 10 days) prior to metformin treatment after the tumors reached a palpable size. As observed with shBACH1, the combination of hemin and metformin significantly suppressed breast tumor growth, while neither hemin nor metformin alone significantly altered tumor growth (shown in FIG. 4E and 8G-H of U.S. Provisional Application No. 62/517,626, which is incorporated by reference).

To test the efficacy of the hemin/metformin combination treatment directly on patient tumors, a TNBC PDX tumor that was selected based on the relatively high BACH1 expression levels was used. PDX tumor pieces (2-3 mm in diameter) were transplanted orthotopically into the mammary fat pads of immunocompromised SCID-BEIGE mice (n=9-10/group) and allowed to grow to ~50 mm in volume prior to treatment with hemin (50 mg/kg/day, i.p) and/or metformin (300 mg/kg/day) for 2 months. Notably, sequential combination treatment with hemin and metformin markedly suppressed PDX tumor volume and weight compared to controls consistent with results obtained from the TNBC xenograft tumors (shown in FIGS. 4F and 8I-J of U.S. Provisional Application No. 62/517,626, which is incorporated by reference). Interestingly, in this PDX model, hemin treatment alone also caused considerable reduction in tumor volumes relative to control tumors or metformin alone. This was not due to overall toxicity, since all the mice in this and previous treatment groups showed no changes in body weight (shown in FIG. 8K of U.S. Provisional Application No. 62/517,626, which is incorporated by reference). Taken together, these results show that depletion of BACH1, either genetically or following hemin treatment, sensitizes TNBC to metformin (shown in FIG. 8G of U.S. Provisional Application No. 62/517,626, which is incorporated by reference).

To determine whether the inverse correlation between BACH1 expression and oxidative phosphorylation also applies to breast cancer patients, Oncoprint analysis showing either upregulation or downregulation of BACH1 and ETC genes were performed for each patient in the TCGA breast cancer provisional data set (shown in FIG. 4H of U.S. Provisional Application No. 62/517,626, which is incorporated by reference). Consistent with other findings, these data demonstrate that, in general, individual patients with high BACH1 expression have low ETC expression, whereas patients with low BACH1 expression have increased ETC expression. It was also noted that BACH1 mRNA expression was increased not only in breast cancer but also in many other cancer types including lung, kidney, sarcoma, and acute myeloid leukemia (shown in FIGS. 4I and 9A of U.S. Provisional Application No. 62/517,626, which is incorporated by reference). Consistent with a similar role for BACH1 in other tumor tissues, the negative correlation between BACH1 and oxidative phosphorylation (ETC genes), including ATP5D and UQCRC1, extends to other major TCGA cancer types including prostate, pancreatic, ovarian, melanoma, colorectal, lung and liver cancers (shown in FIG. 4J and 9B of U.S. Provisional Application No. 62/517,626, which is incorporated by reference).

In conclusion, these results highlight BACH1 as a key regulator of oxidative phosphorylation and an intrinsic molecular determinant of TNBC response to metformin treatment. The striking inverse correlation between BACH1 and ETC gene expression in individual patients raises the possibility that these biomarkers may be useful for prediction of metformin therapeutic outcome. These findings also demonstrate a novel combination therapeutic strategy through repurposing two FDA-approved drugs, Panhematin and metformin. Previous studies have shown that inefficient glucose utilization predisposes cells to inhibitors of mitochondrial respiration. Here it is shown that targeting the BACH1 pathway represents a novel approach to markedly enhancing the efficacy of oxidative phosphorylation inhibitors through restriction of metabolic plasticity. More generally, the inventors propose reprogramming the metabolic network to decrease metabolic variance and increase the fraction of cells dependent upon oxidative phosphorylation as a source of energy and biosynthetic intermediates. This approach would make the cells more susceptible to mitochondrial inhibitors and could also be applied to other tumor types that utilize BACH1 or other key regulators of the metabolic balance.

Example 2 BACH1 Expression is High and Negatively Correlates with Oxidative Phosphorylation in Triple-Negative Breast Cancer Analysis of BACH1 expression in primary tumor datasets compiled by the Cancer Genome Atlas (TCGA provisional, n=1105)[11] showed a significant gain of copy number and gene expression in TNBC and basal-like breast cancer relative to other subtypes such as luminal A, luminal B, HER2-enriched and normal-like breast cancer (FIG. 1A and FIG. 7a). Analysis of other patient datasets such as META-BRIC (n=2509)[2] also showed significant enrichment of BACH1 gene expression in TNBC patients relative to non-TNBC (FIG. 1A), consistent with a role in metastatic progression These results were consistent with BACH1 expression in breast cancer cell lines. Analysis of cell lysates from ER-positive (T47D), TNBC [SUM159PT, MDA-MB-468 (MB468), Hs578T, MDA-MB-436 (MB436), BM1 (a bone-tropic derivative of MDA-MB-231[24]), MDA-MB-157, and BT549], human mammary primary epithelial cells (HMPEC), and non-transformed breast epithelial cells (MCF10A) revealed the more aggressive TNBC cell lines, MB436 and BM1, to be most enriched in BACH1 expression (FIG. 1B). To obtain a range of BACH1-expressing cells, we utilized BM1, MB436 and MB468 cells in subsequent studies.

To further understand which biological pathway involves BACH1 in breast cancer, we carried out a bioinformatics analysis of TCGA breast cancer patient data. KEGG[25] analyses showed oxidative phosphorylation as the functional category that is most negatively correlated with BACH1 expression in both total breast cancer (p=4.09e-16, FDR=5.44e-13) and TNBC (p=1.55e-22, FDR=1.77e-20) (FIG. 1C). Other functional categories that are highly correlated with BACH1 include metabolic pathways as well as a number of neuronal diseases that generally have defective respiratory pathways (e.g. Parkinson's disease[26]). These data suggest that BACH1 is a negative regulator of oxidative phosphorylation.

Example 3 BACH1 Transcriptionally Regulates Mitochondrial Electron Transport Genes and Mitochondrial Respiration in TNBC To determine whether BACH1 inhibits oxidative phosphorylation in TNBC, we analyzed microarrays for differential gene expression in high BACH1 versus BACH1-depleted cells. Initially we used BM1 cells that expressed control vector (BM1-shCont) or BACH1 shRNA (BM1-shBACH1) (FIG. 1D, top). Gene set enrichment analysis (GSEA)[27] identified a significant increase in metabolic pathways including energy metabolism and mitochondrial inner membrane genes upon BACH1 depletion, consistent with a role in oxidative phosphorylation (FIG. 1d,e and FIG. 7b). We validated induction of mitochondrial membrane genes by quantitative RT-PCR and immunoblotting using three human TNBC cell lines that either express or are BACH1-depleted by shRNA or siRNA (FIG. 2A, B and FIG. 8A-C).

To determine whether these genes are direct BACH1 targets, we examined potential BACH1 recruitment sites (MAF recognition element, MARE; TGCTGAG/CTCAT/C (SEQ ID NO: 106) within the promoter regions of these genes[17]. Having identified potential BACH1 binding sites for six mitochondrial genes, ATP5D, COX15, UQCRC1, ATP5J, SLC25A22, and TIMM8B (FIG. 8D), we performed chromatin immunoprecipitation (ChIP) assays using BACH1-enriched TNBC cells (BM1 and MB436) as well as MB468 cells that do not express BACH1 as a negative control (see FIG. 1b). Heme oxygenase 1 (HMOX1) served as a positive control in both cell lines, and shBACH1 cells were included as an additional negative cell control[17] (FIG. 8E). With one exception (ATP5J in MB436 cells), we observed a striking enrichment of BACH1 bound to the promoter regions of these six mitochondrial membrane genes in both BM1 and MB436 cells; by contrast, no significant binding was observed in MB468 cells (FIG. 2C, FIG. 8F). ChIP analysis of Histone 3 Lysine 27 trimethylation (H3K27Me3), a transcription repression histone marker[28], also supports transcriptional suppression of these mitochondrial genes by BACH1.

We then determined whether the inhibition of mitochondrial electron transport chain (ETC) gene expression by BACH1 affects metabolic phenotypes in breast cancer cells. We measured both oxygen consumption rates (OCR), an indication of aerobic respiration, and extracellular acidification rates (ECAR), a read-out of lactic acid produced from increased glycolysis, using a Seahorse XFe96 analyzer. TNBC cells (BM1 or MB436) depleted of BACH1 displayed increased basal and maximum OCR and increased spare respiratory capacity but decreased ECAR relative to the control (FIG. 2D and FIG. 9A). Taken together, these findings demonstrate that BACH1 binds to promoters and inhibits mitochondrial membrane gene expression, thereby suppressing mitochondrial oxidative phosphorylation in breast cancer.

These results suggest that loss of BACH1 rewires the metabolic network from largely glycolytic toward a higher engagement of the tricarboxylic acid (TCA) cycle. To measure the metabolic flux directly, we labeled cells with $^{13}C$-glucose for 16 hours and monitored incorporation of $^{13}C$ into metabolites at the end of this period. Consistent with more oxidative phosphorylation activity, we observed a significant increase in the relative $^{13}C$-levels of pyruvate and $^{13}C$-oxaloacetate (OAA) and a decrease in $^{13}C$-glyceraldehyde 3-phosphate (G3P) levels following BACH1 depletion (FIG. 2E). The fractional isotopic incorporation into $^{13}C$-phosphoenol pyruvate (PEP), $^{13}C$-pyruvate and $^{13}C$-OAA also increased, and the incorporation into $^{13}C$-lactate decreased, confirming that glycolytic flux favors the TCA cycle rather than lactic acid upon BACH1 depletion (FIG. 2F). In line with the cellular metabolomics, lactic acid levels in the conditioned media of TNBC cells were higher in control compared to shBACH1 cells (FIG. 9B). Although significant, the actual changes are moderate, in part due to a diversion of $^{13}C$-glucose in shBACH1 cells into glycerol-phospholipid metabolism as shown by a decrease in relative levels of $^{13}C$-G3P/dihydroxyacetone phosphate (DHAP) and an increase in $^{13}C$-glycerol-3-P levels (FIG. 9C). We also noted an additional diversion of $^{13}C$-glucose to the pentose phosphate shunt as shown by higher relative $^{13}C$-phosphoribosyl pyrophosphate (PRPP) levels in shBACH1 cells (FIG. 9C).

Consistent with these results, mass spectrometry analysis of metabolites identified increased levels of tricarboxylic acid (TCA) cycle intermediates such as citrate and oxaloacetate as well as ATP upon BACH1 knockdown (FIG. 9D). When cells were grown at lower glucose (10 mM) concentrations, we observed a relative decrease in the steady state levels of multiple intermediates in the glycolysis pathway including glucose 6-phosphate (G6P), glucose 1-phosphate (G1P), fructose 6-phosphate (F6P), fructose 1,6-bisphophsphate (F16BP), D-glycerate 3-phosphate (DG3P), and pyruvate (Pyr) as well as reduced lactic acid (Lac) in BACH1-depleted cells (FIG. 9e). In addition, NAD+/NADH levels were increased upon BACH1 depletion, consistent with generation of NAD+ by Complex I of the ETC (FIG. 9F). Taken together, these data indicate that loss of BACH1 reprograms metabolism from a glycolysis-based pathway toward more oxidative phosphorylation-dependent metabolism.

To understand the increased flow of $^{13}C$-labeled glucose metabolites into the TCA cycle, we analyzed the regulation of enzymes involved in pyruvate conversion. Pyruvate is generally metabolized into acetyl-CoA by pyruvate dehydrogenase (PDH), oxaloacetate by pyruvate carboxylase (PC), or lactate by lactate dehydrogenase (LDH)[29]. PDH is additionally inhibited by pyruvate dehydrogenase kinase (PDK), which phosphorylates PDH at Ser29330. We focused on regulation of PDK and PDH since relative lactate levels were decreased, and gene expression of PC was not altered with BACH1 loss (FIG. 9G). BACH1 depletion reduced both PDK1 mRNA as well as phosphorylated PDH levels (Ser293) in both BM1 and MB436 cells (FIG. 2G and FIG. 9I). ChIP assays showed that BACH1 binds to the promoters of PDK genes along with RNA polymerase II in BM1 and MB436 but not MB468 cells (FIG. 2H and FIG. 9J). These results suggest that BACH1 is a transcriptional activator of PDK, leading to phosphorylation and inhibition of PDH activity and decreased pyruvate to acetyl-CoA conversion. Thus, BACH1 depletion favors oxidative phosphorylation as a source of energy and biosynthetic precursors and impairs glycolysis by targeting key metabolic regulatory steps.

Figure 10D:
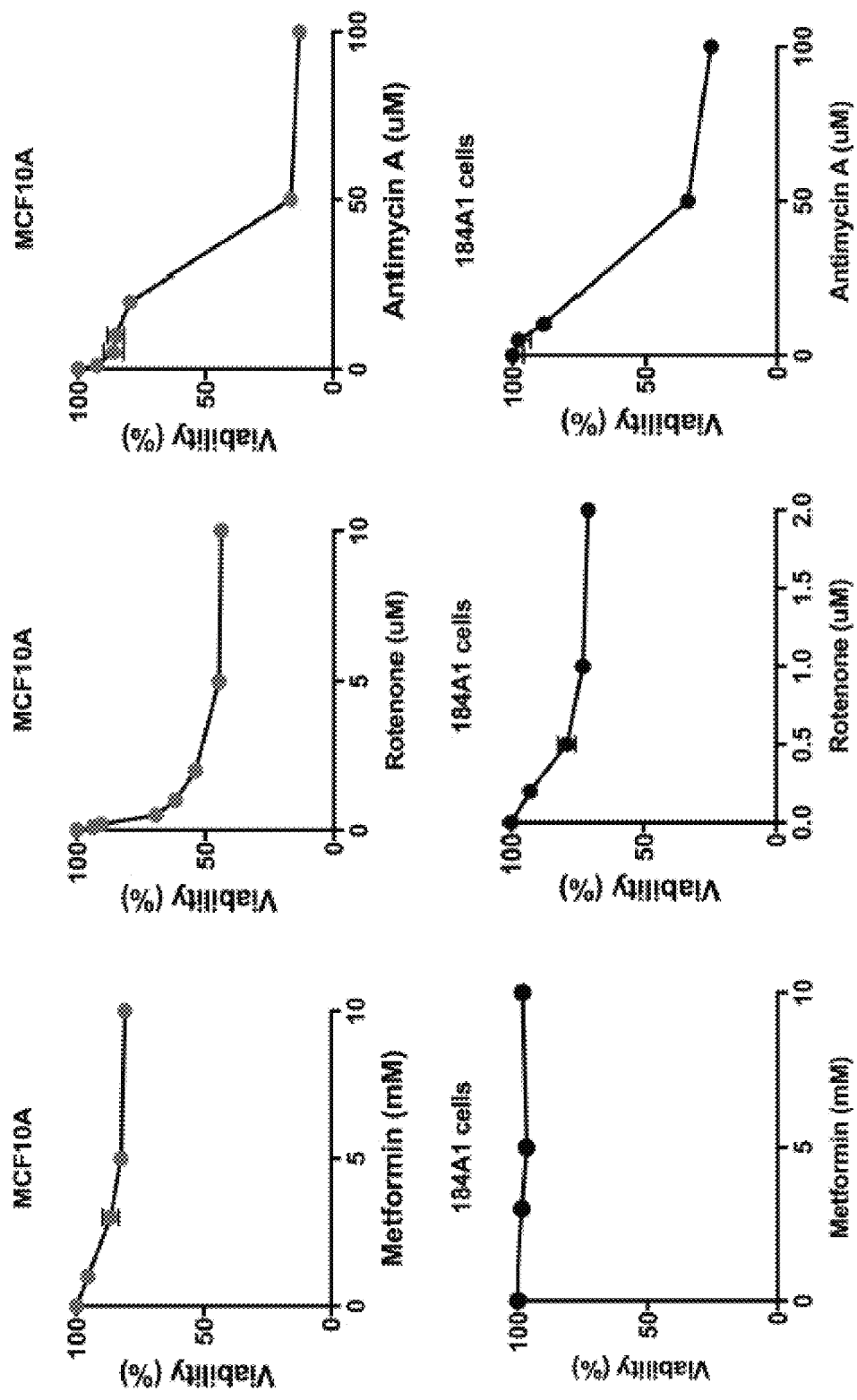

Example 4-BACH1 Confers Resistance to Mitochondrial Respiratory Inhibitors in TNBC Since BACH1 depletion promotes induction of aerobic metabolism, we hypothesized that the tumor cells should have increased sensitivity to agents that inhibit these pathways. Metformin as a cancer drug revealed targets mitochondrial metabolism[31-34]. For example, experiments using metformin-resistant yeast complex I subunits have shown that complex I is a primary target of metformin in cancer[32, 33]. To determine whether the survival of TNBC cells with BACH1 knockdown is compromised by treatment with respiratory inhibitors, viable cells were monitored after treatment with metformin, rotenone, or antimycin A. Treatment with ETC inhibitors reduced viability of BACH1-depleted cells relative to control cells using both calcein AM assays and Incucyte cell growth measurements[35] (FIG. 3a and FIG. 10a-c). Metformin doses routinely used for cells are significantly higher than effective doses for tumors in vivo due at least in part to differences in cell culture versus physiological conditions[34,36-38]. Importantly, metformin did not alter the viability of non-malignant mammary epithelial cells (184A1 and MCF10A). By contrast, rotenone, an ETC complex I inhibitor, was more toxic at even lower dosages, reducing cell viability by 25-50%[39] (FIG. 10d). Since metformin was less toxic for the non-malignant epithelial cells, we used metformin for further studies.

BACH1-depleted TNBC cells were more sensitive to ETC inhibitors than BACH1-expressing cells. MB468 cells, which marginally express BACH, were also more sensitive to metformin than BM1 or MB436 cells (FIGS. 11A and B). BACH knockdown in MB436 or BM1 cells drives increased sensitivity to metformin treatment, whereas BACH1 overexpression in MB468 cells renders cells more resistant to metformin treatment (FIG. 11C). Together, these results suggest that BACH1 expression is a determinant of metformin efficacy.

Metformin treatment may deplete $NAD^+$ levels by inhibiting ETC Complex I, which turns over NADH that is coupled to numerous metabolic processes including the malate aspartate shuttle and related anabolic pathways[40,41]. BACH1 depletion enhanced $NAD^+$ levels, consistent with increased mitochondrial activity (FIG. 9B). As noted previously[34,38], addition of pyruvate (2.5 mM) to the growth media increased $NAD^+$ levels (FIG. 3b) and completely rescued the inhibitory effect of metformin (FIG. 3c), consistent with mitochondria as the target of metformin in the TNBC cells. Notably, expression of the organic cation transporter (OCT1), a metformin transporter, was not altered by BACH1 depletion as shown by qRT-PCR (FIG. 11D). Furthermore, expression of mitochondrial biogenesis genes such as peroxisome proliferator-activated receptor gamma (PPARγ) or peroxisome proliferator-activated receptor gamma coactivator1-alpha (PGC1α) was not altered by BACH1 depletion (FIG. 11E). These results suggest that neither metformin transporters nor mitochondrial master regulators are responsible for the increased sensitivity. Since mitochondrial ETC genes were induced in BACH1 depleted cells, we assessed whether these genes are required for metformin sensitivity. Silencing of COX15 or UQCRC1 using siRNA in BM1-shBACH1 cells completely restored metformin resistance and rescued cell growth (FIG. 3D and FIG. 11F-H). Together, these results demonstrate that BACH1 depletion increases mitochondrial ETC gene expression and respiration in TNBC cells, thereby enhancing sensitivity to ETC inhibitor treatment.

Example 5-Pharmacological BACH1 Suppression Using Hemin

To take advantage of BACH1 as a target pharmacologically, we utilized hemin, the active ingredient of the FDA-approved drug (panhematin), as an alternative means of depleting BACH1[42]. Heme binding causes BACH1 degradation in the cytoplasm[19]. TNBC cells were treated with a range of hemin (10-80 μM) up to 124 hours, a dose that is neither cytotoxic nor growth inhibitory yet is still effective at reducing BACH1 levels. Therefore, we used the intermediate dose of 20 μM hemin for subsequent assays (FIGS. 12A and B). Hemin treatment for 48 hours increased mitochondrial gene expression as well as HMOX1, similar to the induction observed upon genetic depletion of BACH1 in BM1 and MB436 cells (FIG. 4 A, B and FIG. 12C). In addition, hemin pre-treatment altered cellular metabolic phenotypes, inducing higher maximum OCR and a higher spare respiratory capacity but lower basal ECAR, consistent with genetic deletion of BACH1 (FIG. 4C and FIG. 12D). As anticipated, upon subsequent treatment with ETC inhibitors including metformin, hemin exposure significantly decreased viability of BM1 (FIG. 4D and FIG. 12E), MB436 and BT549 cells (FIG. 12F-I). These results indicate that pharmacological depletion of BACH1 using hemin mimics genetic knockdown of BACH1 for transcriptional regulation, metabolic phenotype and ETC inhibitor sensitivity.

Since heme has numerous biological functions ranging from redox to signaling, the possibility remains that the action of hemin in combination with metformin is independent of BACH1. To address this concern, we utilized several approaches to determine whether hemin increases metformin sensitivity of cells by targeting BACH1 and/or BACH1-regulated genes. First, as noted previously, expression of wild type (wt) BACH1 in MB468 cells converted cells from a metformin-sensitive to a metformin-resistant phenotype. When we treated these BACH1-expressing cells with hemin, metformin sensitivity was restored (FIG. 4E, F). Second, overexpression of wt BACH1 in MB436-shBACH1 cells generated a metformin-resistance phenotype (FIG. 12J, K). Third, to specifically address hemin specificity, we generated a heme-resistant BACH1 mutant (Mut-Bach1). This mutant has cysteine to alanine point mutations in 4 heme binding motif sites in the C-terminus of BACH1. These sites have been implicated in heme binding and release of BACH1 from DNA for nuclear export and subsequent degradation[44]. As expected, hemin treatment (20 μM) did not degrade Mut-Bach1 (FIG. 4G). Furthermore, expression of Mut-Bach1 in two TNBC cell lines (BM1-shBACH1 and MB436-shBACH1) restored resistance to metformin even following heme treatment and functionally inhibited transcription of HMOX1 (FIG. 4H,I and FIG. 12L-N). Taken together, these results indicate that hemin treatment causes sensitivity of cancer cells to metformin through induction of BACH1 degradation.

Example 6 Combination Treatment Using Hemin and Metformin Suppresses BACH1-Enriched Breast Tumor Growth Given the critical role of BACH1 in regulating sensitivity to ETC inhibitors in vitro, we then tested whether BACH1 is a useful therapeutic target in vivo using several pre-clinical TNBC mouse models. We used metformin (200-300 mg/kg) in the range commonly used for mouse studies[33,38]. These metformin doses result in mouse tumor and plasma concentrations (3-12 μM) that are similar to the levels in metformin-treated human diabetic patients (~10 μM range)[45,46].

Initially, BACH1-depleted xenograft TNBC tumors (MB436-shBACH1 and BM1-shBACH1) were treated with metformin in drinking water when tumors reached a palpable size (~25 mm³). BACH1 depletion alone did not alter tumor growth compared to control tumors, consistent with previous observations[13]. Similarly, no effect on control tumor growth was seen with metformin alone. However, growth of TNBC tumors that stably express shBACH1 was drastically suppressed within one week of metformin administration (FIG. 5A and FIG. 7a-c). Comparable results were observed with BM1 xenograft tumors expressing shBACH1 (FIG. 13D). MB436-shBACH1 tumors also had reduced BACH1 and pPDH (Ser293) protein levels, consistent with in vitro measurements in cultured cells (FIG. 5B and FIG. 13E). Moreover, a significant fraction of shBACH1 MB436 xenograft mice were tumor-free following metformin treatment (FIG. 5C). Finally, loss of BACH1 suppressed formation of lung metastases, consistent with previous observations[13] (FIG. 5D and FIG. 13F).

After demonstrating that BACH1 depletion overcame tumor resistance to metformin treatment, we then asked whether the pharmacological combination of hemin and metformin is similarly effective. We first monitored BACH1 expression in the mouse TNBC models by immunoblotting using tumor lysates (FIG. 5E). A transgenic TNBC mouse model, (C3(1)-TAg)[47], had very low BACH1 expression whereas the BM1 xenograft and patient-derived xenograft (PDX) tumors expressed relatively high levels of BACH1. As predicted, the C3(1)-TAg mice (n=5/group) were highly sensitive to metformin in the absence of hemin treatment (FIG. 5F). To test the efficacy of hemin treatment of tumors, we determined the optimal dosing schedule for hemin degradation of BACH1 by immunoblotting, and validated functional loss of BACH1 by measuring induction of HMOX1 expression (FIG. 14A, B). We then pretreated MB436 xenograft mice that displayed palpable tumors with a dose of 50 mg/kg/day hemin for 10 consecutive days prior to combined hemin and metformin treatment for 6 weeks. The combination treatment using hemin and metformin significantly suppressed breast tumor volume compared to control (p=0.0025), while neither hemin nor metformin alone altered tumor growth (FIG. 5G and FIG. 14C, D).

Finally, to test the efficacy of the hemin/metformin combination treatment directly on patient tumors, we used a BACH1-enriched TNBC PDX tumor that was selected based on the relatively high BACH1 expression levels. PDX tumor pieces (2-3 mm in diameter) were transplanted orthotopically into the mammary fat pads of immunocompromised SCID-BEIGE mice[48] (n=9-10/group) and allowed to grow to ~50 mm$^3$ in volume prior to treatment with hemin (50 mg/kg/day) and/or metformin (300 mg/kg/day) for 2 months. Notably, combination treatment with hemin and metformin markedly suppressed PDX tumor size compared to controls, (p=0.0007) consistent with the results obtained from the TNBC xenograft tumors (FIG. 5H and FIG. 14E,F). Interestingly, in this PDX model, hemin treatment alone also caused reduction in tumor volumes relative to control tumors (p=0.0007) or metformin alone (p=0.0001). However, the combination of hemin and metformin significantly reduced tumor volumes even further (p=0.0459). This was not due to overall toxicity, since all the mice in this and previous treatment groups showed no changes in body weight (FIG. 14G). As observed with xenograft tumors, both BACH1 and pPDH (Ser293) protein expression in PDX tumors were depleted following hemin treatment (FIG. 5I). Taken together, these results show that depletion of BACH1, either genetically or pharmacologically using hemin, sensitizes TNBC to metformin treatment through inhibition of PDK and activation of the electron transport genes (FIG. 5J).

Example 7-Inverse Correlation Between BACH1 and ETC Genes in Patient Cohort

These findings are supported by bioinformatics analyses of clinical samples. Expression of ETC genes such as UQCRC1 and ATP5D (see FIG. 1e) is negatively correlated with expression of BACH1 (Pearson's=−0.35, Spearman's=−0.4) in the TCGA breast cancer dataset (n=1105) (FIG. 6A and Supplementary Data Table 1). Of these patients, a small but significant fraction (n=119) was TNBC. Similarly, ETC gene expression, as illustrated by COX15, ATP5D, and ATP5G2, is significantly lower whereas BACH1 expression is enriched in TNBC patients in multiple breast cancer data sets (METABRIC, GSE2034, GSE11121) (FIG. 6B-D and FIG. 15A-C).

To determine whether the inverse correlation between BACH1 and ETC gene expression also applies to individual breast cancer patients, we did Oncoprint analysis. The heat map illustrates either upregulation (red) or downregulation (blue) of genes for each patient using the TCGA breast cancer data set (FIG. 6E). Consistent with our in vitro results, these data demonstrate that, for a substantial fraction of patients, individuals with high tumor BACH1 expression have low tumor ETC expression, whereas other patients with low tumor BACH1 expression have high tumor ETC expression. We also noted that an additional group of patients exhibit low to relatively high ETC gene expression at moderate BACH1 levels (FIG. 6E).

Figure 16:
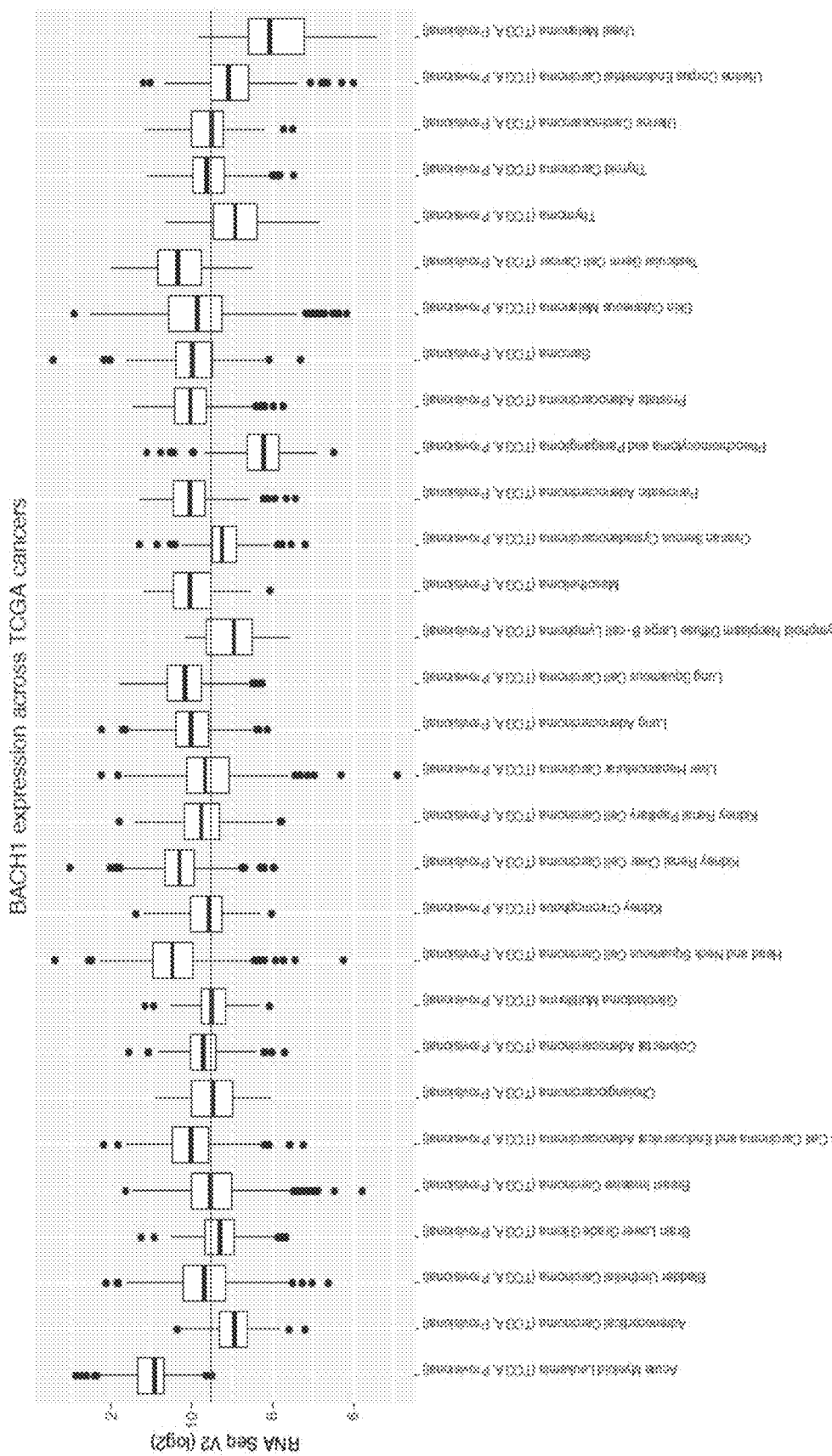
FIG. 16. BACH1 expression is enriched in various cancer. BACH1 expression (RNA-seq) in TCGA provisional cancer data sets. Red bar indicates median BACH1 expression level in breast cancers.
Figure 17:
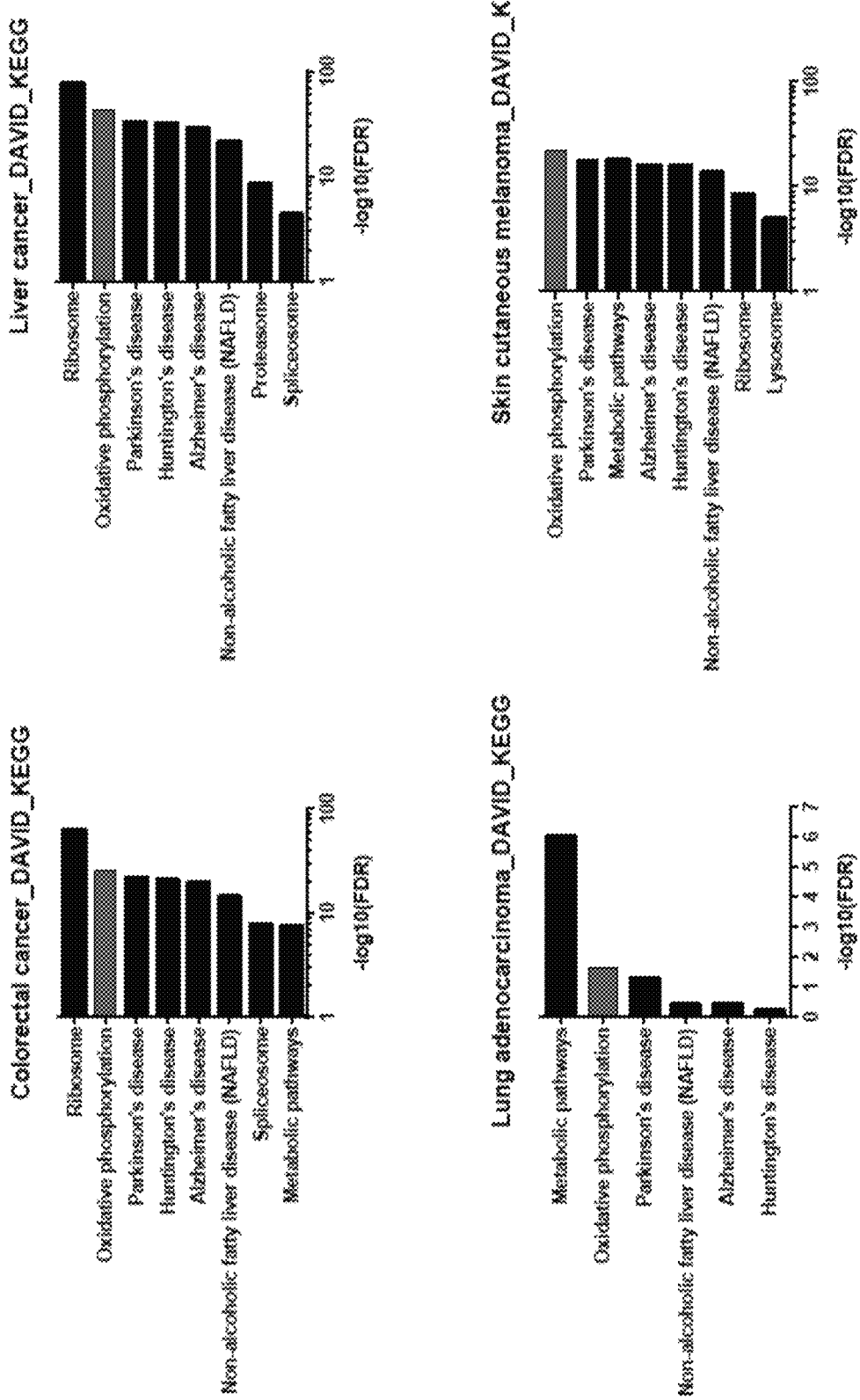
FIG. 17. KEGG pathways are negatively correlated with BACH1 expression in TCGA cancer. KEGG pathway analyses, carried out using DAVID, of genes that are negatively correlated with BACH1 expression are shown. The top 8 most significantly enriched pathways with FDR values (−log 10FDR) are shown for each cancer type of colorectal, liver, lung, skin, ovary, pancreas, prostate and TNBC.
Figure 17:
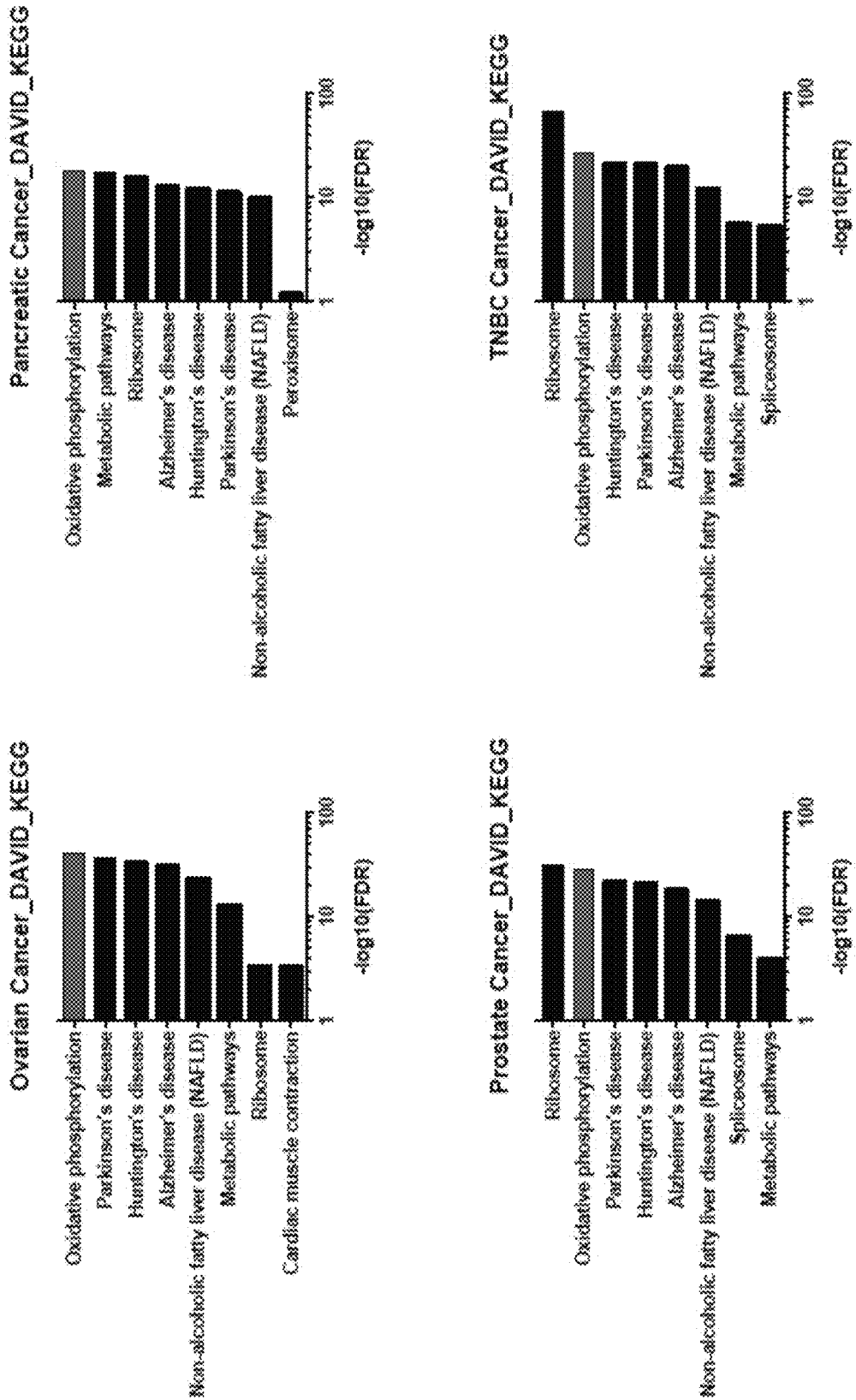

We next addressed BACH1 expression levels in other types of cancer. BACH1 mRNA expression was increased not only in breast cancer but also in many other cancer types including lung, kidney, uterine, prostate, and acute myeloid leukemia (FIG. 6F and FIG. 16). Consistent with a similar role for BACH1 in other tumor tissues, the negative correlation between BACH1 and oxidative phosphorylation in KEGG pathways extends to other major TCGA cancer types including prostate, pancreatic, ovarian, melanoma, colorectal, lung and liver cancers (FIG. 6G). The top 8 most negatively correlated pathways are shown for each cancer type (FIG. 17). Moreover, co-expression analyses using TCGA data revealed a significant inverse correlation between BACH1 and individual ETC genes such as UQCRC1 (Spearman's≤−0.3, Pearson's≤−0.3) in tumors from skin, prostate, colorectal, and liver cancer patients (FIG. 6H). Finally, oncoprint analyses demonstrating inversely correlated expression of BACH1 and ETC genes in individual patient tumors were also observed for other TCGA cancer types including liver, prostate, skin, and colon cancers (data not shown). Together, patient data analyses suggest that BACH1 inhibition of mitochondrial ETC genes may be a common mechanism in cancer.

VIII. METHODS SUMMARY

TNBC cell lines stably knocked down with lenti-viral shRNA for BACH1 were constructed and maintained as described previously. Gene expression analysis of cultured cells and isolated tumor tissues used a Reverse transcriptase kit followed by Roche96 cycler for real time mRNA quantification and Lycor imaging for immunoblotting. For in vitro cell viability assay with mitochondrial inhibitors, TNBC cells ($2 \times 10^3$-$5 \times 10^3$/well) seeded on 96 well plates overnight with culture media (DMEM with 25 mM Glucose) were treated with inhibitors in fresh culture media (DMEM with 1.25 mM Glucose) for 48 and 72 hours and stained with calcein AM and/or monitored for cellular confluency using an IncuCyte Zoom Live Cell Analysis system. Extracellular flux analyzer was used to assay metabolic phenotypes of BACH1-depleted TNBC cells and TNBC cells that are treated with hemin overnight before assays. For bioinformatics analysis using primary patient data cohort (TCGA), cBioportal and R were used. All protocols for animal studies were approved by the University of Chicago Institutional Animal Care and Use Committee.

A. Cell Cultures

Human breast cancer cell lines (MDA-MB-231-BM1, MDA-MB-436, BT549) and nonmalignant mammary epithelial cells (MCF10A and 184A1) were obtained from ATCC and cultured as described previously. Stable knock down of BACH1 was carried out using a lenti-viral construction carrying shRNA targeting BACH1. Transfected breast cancer cells were selected with puromycin (0.2 μg/ml) in growth media for 10 days. Expression of BACH1 was validated by western blotting with an anti-BACH1 antibody. Mycoplasma detection kits were used routinely to ensure cells are not infected with mycoplasma using MycoAlert Detection Kit (Lonza). Cell line authentication was validated by STR analysis.

B. Real-Time Quantitative PCR

Total RNA from cells and tumor samples was isolated using Trizol (Invitrogen) according to the manufacturer's instructions. Two μg of RNA was adapted for reverse transcriptase PCR (Applied Biosystem) to generate cDNA. Real-time PCR was carried out using LightCycler 96 (Roche) and a Fast Start Essential DNA master mix (2×) reagent. Cq values normalized relative to the expression of endogenous control genes using $2^{(-\Delta\Delta Cq)}$ were plotted. Primer pairs used are shown in the table below:

TABLE 2

List of primers for gene expression analysis using real time RT-PCR and ChIP assays.

| Genes | Forward primer (5'-3') | SEQ ID NO | Reverse primer (3'-5') | SEQ ID NO |
|---|---|---|---|---|
| \multicolumn{5}{c}{Primers for Real Time RT-PCR} |
| BACH1 | CACCGAAGGAGACAGTGAATCC | 16 | GCTGTTCTGGAGTAAGCTTGTGC | 17 |
| ATP5J | GTTCTCCTCTGTCATTCGGTCA | 18 | TCCAGATGTCTGTCGCTTAGAT | 19 |
| ATP5G | CCAGAGTTGCATACAGACCAAT | 20 | CCCATTAAATACCGTAGAGCCCT | 21 |
| ATP5D | TCCCACGCAGGTGTTCTTC | 22 | GGAACCGCTGCTCACAAAGT | 23 |
| COX15 | CAGCGCCTAGAGCACAGTG | 24 | GCCAGACTCTGTCAACCTAGT | 25 |
| COX18 | GGGCAGCATTCTGCTCTCC | 26 | CCCAACTGATTTGCACGAACT | 27 |
| HSD3B | CACATGGCCCGCTCCATAC | 28 | GTGCCGCCGTTTTTCAGATTC | 29 |
| MRPL10 | CACCGTCGTGTGATGCACTT | 30 | CGGCTATCATTCGGTTGTCCT | 31 |
| NDUFA9 | GTCACGTTCTGCCATTACTGC | 32 | GGTGGTTGACAACATATCGCC | 33 |
| NDUFB6 | CCACAGAAGATGGGGCCTATG | 34 | TCCAGACAGGTACAAGTACATGA | 35 |
| NDUFS7 | CTTCGCAAGGTCTACGACCAG | 36 | GGAATAGTGGTAGTAGCCTCCTC | 37 |
| OCT1 | GTG TGT AGA CCC CCT GGC TA | 38 | GTG TAG CCA GCC ATC CAG TT | 39 |
| PDHA | TGGTAGCATCCCGTAATTTTGC | 40 | ATTCGGCGTACAGTCTGCATC | 41 |
| PDHB | AAGAGGCGCTTTCACTGGAC | 42 | ACTAACCTTGTATGCCCCATCA | 43 |
| PDHX | TTGGGAGGTTCCGACCTGT | 44 | CAACCACTCGACTGTCACTTG | 45 |
| SLC25A15 | CCTGAAGACTTACTCCCAGGT | 46 | GCGATGTTGGCGATTAGTGC | 47 |
| SLC25A22 | GCCAGCCAAGCTCATCAATG | 48 | GAGGCAGTCGGACATGCTC | 49 |
| TIMM17A | GGTGGGGCCTTTACGATGG | 50 | GCCCTGGTTTTAATAGCTGTCA | 51 |
| T1MM8B | TCACTTCATGGAGTTATGTTGGG | 52 | AGACAATTTTCAGTGCGAGAGTC | 53 |
| UCP3 | TGTTTTGCTGACCTCGTTACC | 54 | GACGGAGTCATAGAGGCCGAT | 55 |
| UQCRC1 | GGGGCACAAGTGCTATTGC | 56 | GTTGTCCAGCAGGCTAACC | 57 |

TABLE 2-continued

List of primers for gene expression analysis using real time RT-PCR and ChIP assays.

| Genes | Forward primer (5'-3') | SEQ ID NO | Reverse primer (3'-5') | SEQ ID NO |
|---|---|---|---|---|
| Primers for ChIP assays | | | | |
| ATP5D | GAGGAAGCCTGGTCAGCTC | 58 | CAGGGAAGACCCAGCTTGT | 59 |
| ATP5J | AACTGGAGTCCCAAAAGGCC | 60 | GAAGTAGAGCGGAGGTGGTG | 61 |
| COX15 | TGGGACAGGGATGAGTGATT | 62 | TGTCTGCTTTGTTTTCATTTGC | 63 |
| COX18 | ACTGTTGATGACTGAAAAGCCA | 64 | AAAAGCCACCACTGTTCCCA | 65 |
| SLC25A22 | GCCAGGTCGATGGGAAACA | 66 | CATGGTCAAGGAAGCCGGT | 67 |
| TIMM8B | AGCCCATACCTCTGTAGCCA | 68 | CCCGTGCTGAACAAGAGTCA | 69 |
| UCP3 | AAAGCTCTGCCTAAGACCGC | 70 | CCATCCAGGAGCGACAGAAA | 71 |
| UQCRC1 | GTTGGGATGGAGGTTGAATGA | 72 | GTGTGTATCTCTGTGCCTGTG | 73 |
| PDK1 | AACAAGGGCAGCTTGGAAGT/ | 74 | GTGAGGGGTGAGTCAGTTC | 75 |
| PDK2 | TGCACACAAGGGACCTTCAG | 76 | TCGACCTTGGGAGGAAATGC | 77 |
| PDK3 | ACACAAACGTCACAGAGGCA | 78 | GAGTCGGTTGCTGCACGTA | 79 |
| PDK4 | GGCTTGGGTTTCCTGTCTGT | 80 | AGCGGGTCACATTCTCAGTG | 81 |

C. Cell Proliferation and Viability Assays

Breast cancer cells (5,000 cells/well) and non-malignant mammary epithelial cells (8,000 cells/well) were plated on 96-well plates to observe growth of cells every 4 hours by phase contrast imaging using an IncuCyte Zoom Live Cell Analysis system (Essen Bioscience). After 24 hours of plating, inhibitors were added and monitored until control cells reached 100% confluent. To determine cell viability, cells were seeded in black walled 96-well plates overnight and treated with inhibitors for 48 hours. Calcein AM (R&D system) in PBS was then added and incubated for 1 hour at 37° C. Fluorescence was determined using a Victor3 plate reader (PerkinElmer) with excitation at 420 nm and emission at 520 nm. The absorbance was used to reflect live cell numbers and was normalized to those in control with vehicles and shown as relative viability (%).

D. Chemicals

Hemin (Sigma) was prepared in 20 mM NaOH for in vitro assays or further diluted in PBS to adjust pH to 7.5 and filter sterilized using 0.22 μm filters for animal treatment. Rotenone (Sigma) and Antimycin A (Sigma) were prepared as stock solutions and added to growth media. Sodium Pyruvate (Gibco 11360) was added directly to growth media.

E. siRNA siRNAs for BACH1 (3 unique 27mer siRNA duplexes SR300391, Origene), UQCRC1 (Human UQCRC1 Flexi tube siRNA, SI00051275, Qiagen) and COX15 (Human COX15 6flexi Tube siRNA, SI014180911, Qiagen) or siRNA control (Universal Scrambled negative control siRNA, SR30004, Origene) were transfected into breast cancer cells with Lipofectamine 3000 (Invitrogen) in OPTI-MEM overnight for in vitro assays.

F. Chromatin Immunoprecipitation Assays

Two million cells were plated on 10 cm plates overnight prior to crosslinking with 10% formaldehyde for 10 min followed by quenching with 2 M glycine for 3 min. After washing cells with cold PBS, total cell lysates in ice were sonicated at 80% output for 10 seconds with a 10 second pause for 4 cycles and pre-cleared with goat-IgG for 1 hour at 4° C. Supernatants were immunoprecipitated with antibodies against BACH1 (AF5776, R&D System), RNA Pol II (Cell Signalling), H3K273Me (Abcam) antibody or IgG (normal Goat, Santa Cruz) overnight and followed by washing for qPCR as previously described in the art. Primers for ChIP qPCR are as following.

```
COX15-Forward (5'-3'):
                                        (SEQ ID NO: 82)
TGGGACAGGGATGAGTGATT/

Rev:
                                        (SEQ ID NO: 83)
TGTCTGCTTTGTTTTCATTTGC
```

ATP5C-Forward:
GAGGAAGCCTGGTCAGCTC/ (SEQ ID NO: 84)

Rev:
CAGGGAAGACCCAGCTTGT (SEQ ID NO: 85)

UQCRC1-Forward:
GTTGGGATGGAGGTTGAATGA/ (SEQ ID NO: 86)

Rev:
GTGTGTATCTCTGTGCCTGTG (SEQ ID NO: 87)

ATP5J-Forward:
AACTGGAGTCCCAAAAGGCC/ (SEQ ID NO: 88)

Reverse:
GAAGTAGAGCGGAGGTGGTG (SEQ ID NO: 89)

SLC25A22-Forward:
GCCAGGTCGATGGGAAACA/ (SEQ ID NO: 90)

Reverse:
CATGGTCAAGGAAGCCGGT (SEQ ID NO: 91)

UCP3-Forward:
AAAGCTCTGCCTAAGACCGC/ (SEQ ID NO: 92)

Reverse:
CCATCCAGGAGCGACAGAAA (SEQ ID NO: 93)

TIMM8B-Forward:
AGCCCATACCTCTGTAGCCA/ (SEQ ID NO: 94)

Reverse:
CCCGTGCTGAACAAGAGTCA (SEQ ID NO: 95)

COX18-Forward:
ACTGTTGATGACTGAAAAGCCA/ (SEQ ID NO: 96)

Reverse:
AAAAGCCACCACTGTTCCCA (SEQ ID NO: 97)

PDK1-Forward:
AACAAGGGCAGCTTGGAAGT/ (SEQ ID NO: 98)

Reverse:
GTGAGGGGGTGAGTCAGTTC (SEQ ID NO: 99)

PDK2-Forward:
TGCACACAAGGGACCTTCAG/ (SEQ ID NO: 100)

Reverse:
TCGACCTTGGGAGGAAATGC (SEQ ID NO: 101)

PDK3-Forward:
ACACAAACGTCACAGAGGCA/ (SEQ ID NO: 102)

Reverse:
GAGTCGGTTGCTGCACGTA (SEQ ID NO: 103)

PDK4-Forward:
GGCTTGGGTTTCCTGTCTGT/ (SEQ ID NO: 104)

Reverse:
AGCGGGTCACATTCTCAGTG (SEQ ID NO: 105)

G. Immunoblotting

Whole cell lysates were prepared using RIPA buffer (Sigma) with protease inhibitor cocktails (1:100 ThermoFisher) and phosphatase inhibitors (SimpleStop1, Gold Biotechnology) at 4° C. and quantified using Bradford assays for western blotting using antibodies against BACH1 (sc-271211; Santa Cruz), and alpha-TUBULIN (sc-28199; Santa Cruz). Blots were imaged and processed using a Licor Odyssey Fc, dual-mode imaging system (Licor).

H. NAD/NADH, Lactate, Glucose Measurement

NAD(H) was measured using the NAD/NADH-Glo Assay kit (Promega) in accordance with the manufacturer's protocol. Lactate produced by cells were measured using the media that $5 \times 10^5$ cells were plated on 6 well plates in 2 ml media containing 1.25 mM glucose for 3 days or overnight. Harvested media was used for L-Lactate Assay Kit I (Eton Bioscience). For glucose consumption measurement, media from the cells cultured in 12 well plates were freshly replenished with media containing 5 mM glucose and collected after 21 hours for glucose measurement using Glucose Assay Kit I (Eton Bioscience).

I. Metabolic Phenotypes

Extracellular acidification rates (ECAR) and oxygen consumption rates (OCR) were monitored by a Seahorse Bioscience Analyzer (XF24; Univ. of Illinois at Chicago and XFe96; Biophysics Core Facility at Univ. of Chicago). Cells were seeded in 24 well plates at a density of $5 \times 10^4$ and 96 well plates at a density of $8 \times 10^3$ cells per well with growth media for at least 18 hours. The following day, media was changed to base media (DMEM, 143 mM NaCl, Phenol red, pH 7.35). For ECAR analysis, cells were added with media (2 mM Glutamine, pH 7.35) and monitored every 3 minutes following successive administration of 10 mM of glucose, and inhibitors such as 1 μM of oligomycin and 50 mM of 2-DG. For OCR analysis, cells were added with mito stress test base media (10 mM Glucose, 2 mM Glutamine, 1 mM Pyruvate, pH 7.4) and monitored every 3 minutes following successive administration of inhibitors such as 2 μM of oligomycin, 2 μM of FCCP, and 0.5 M of Rotenone/AntimycinA. BCA protein assays were used to normalize metabolic rates to cell number.

J. Mouse Experiments

All animal protocols related to mouse experiments were approved by the University of Chicago Institutional Animal Care and Use Committee. Two million human breast cancer cells (MDA-MB-436-shCont, MDA-MB-436-shBACH1, BM1-shBACH1, or BM1-shCont) in 100 μl PBS were injected into the mammary fat pads of 5 to 6 weeks old athymic nude female mice (Charles River Laboratories). When tumors were about 20-30 or 50 mm$^3$ in volume, hemin (50 mg/kg/day) or vehicle (20 mM NaOH in phosphate buffered saline) was injected intraperitoneally for 10 days prior to metformin treatment for 8 weeks. Metformin (200 mg/kg for MDA-MB-436 cells or 300 mg/kg for BM1-cells) was provided in drinking water ad libidum. Tumor growth was monitored weekly by caliper measurement in two dimensions to generate ellipsoid volumes using an equation of vol.=$0.4 \times (L \times W^2)$.

For a transgenic TNBC mouse model, C3(1)-TAg, mice (n=5/group) were treated with metformin (200 mg/kg/day), after 10 days of mice developed palpable tumors (about 25 mm$^3$), at age of 15 weeks. Tumor volume was assayed by caliper measurement twice per week.

For a patient-derived xenografts (PDX) model, frozen PDX tumors in 0.5 ml of sterile HBSS were prepared in a volume of 10-20 mm$^3$. In brief, tumor fragments were implanted into the mammary fat pads of 5 weeks old SCID-Beige mice following standard procedures. When tumors reached 50 mm$^3$ in volume, hemin (50 mg/kg/day, i.p) and metformin (300 mg/kg) in drinking water were administrated for 6 weeks. Tumor volume was measured by caliper weekly. Tumor weight was measured at the end of drug treatment. Tumor size was shown as mean+/_s.e.m. with significance (p-value) by paired Student's t-test. All the animals were also monitored regularly for body weights.

K. Statistical Analysis

Gene expression, ChIP assays, viability assays and tumor volumes in vitro and in vivo data were analyzed using two-tailed t-test and one-way ANOVA using GraphPad Prism 7.0a software. In vitro experiments were repeated at least three times for statistical analyses. According to in vitro data, effect size of hemin/metformin on cancer cell growth was 80-90% with p-value less than 0.05, which results in at least 6 mice per group would be required to ensure adequate power. For in vivo animal experiments, mouse allocation to the treatment group was randomized when tumors reached the minimum size and the mice that failed tumor formation were excluded from the experiments. For human data analysis using TCGA was performed in the R environment.

L. GSA and GSEA Analysis

The R package "GSA" was used to determine which gene sets were enriched in the shBACH1 phenotype. 200 permutations were used to estimate false discovery rates. Enriched gene sets with p and FDR values more than 5% were filtered out. After the initial enrichment analysis, positively correlated (enrichment score >0) and negatively correlated (enrichment score <0) were considered separately.

Gene Set Enrichment Analysis was conducted on the desktop version of the GSEA software (v2.2.3). The "max-probe" option was used for collapsing expression values of genes with multiple probes. Gene set size was limited to 10-500 genes per set. Student's t-test was the metric used for ranking genes. Like GSA analysis, 200 permutations were used to estimate false discovery rates.

M. TCGA Data Analysis

BACH1 expression data (RNA Seq V2 RSEM) from 817 publically available breast cancer cases was downloaded from cBioPortal website (www.cbioportal.org) in the form of z-score transformed data. The clinical data associated with these breast cancer cases were also downloaded from the same website. Triple negative breast cancer sub-population within the breast cancer cases was determined by "Negative" status for the IHC scores of ER, PR, and Her2 genes (total of 83 cases). For the analysis of BACH1 expression across different Pam50 categories, TCGA breast cancer expression and clinical data were accessed and processed using the R package "TCGAbiolinks" (installed through Bioconductor.org). This analysis was done solely on cases for which Pam50 classification information was available (total of 522 cases: 98 basal, 58 Her2-enriched, 231 luminal-A, 127 luminal-B, 8 normal-like). Statistical significance of differential BACH1 expression between different PAM50 subgroups, as well as TNBC vs. Non-TNBC, was determined by Student's t-test (p<0.05).

Comparison of BACH1 expression levels in different cancer types was conducted based on RNA-seq values (log 2) of BACH1 in the provisional TCGA data sets. All cases (complete and incomplete) were used for each cancer type. Genes that are negatively correlated with BACH1 were determined based on a Spearman coefficient cut-off of +/−0.3. These genes then were subjected to KEGG pathway enrichment analysis either by DAVID (available on the world wide web at david.ncifcrf.gov) or by the R package "goseq" (available on the world wide web at bioconductor.org/packages/release/bioc/html/goseq.html).

The frequency of tumors that have upregulated BACH1 expression with respect to their matched healthy tissue was determined using the online tool BioXpress (available on the world wide web at hive.biochemistry.gwu.edu). Only those TCGA samples that have a matched normal tissue expression data were used for this analysis.

N. Mutant Bach1 Heme Binding

Heme binding dipeptide motifs (CP) of Bach1 were mutated to Alanine (A) from Cystein (C) at Cys438, Cys464, Cys 495, and Cys649 (Thermo Fisher) and cloned into pCDH and sequenced for mammalian cell transduction using Lipofectamin 3000 (Invitrogen).

O. Lung Metastasis

Whole fixed lungs were evaluated by serial sectioning every 100 μm and followed by H&E staining (Human Tissue Resource Center, University of Chicago) for visualization of lung metastasis under microscope (Evos XL cell imaging system, Thermo Fisher).

P. Patient Data Analysis

BACH1 expression data (RNA Seq V2 RSEM) from 817 publically available breast cancer cases was downloaded from cBioPortal website (cbioportal.org) in the form of z-score transformed data. The clinical data associated with these breast cancer cases were also downloaded from the same website. Triple negative breast cancer sub-population within the breast cancer cases was determined by "Negative" status for the IHC scores of ER, PR, and Her2 genes (total of 83 cases). For the analysis of BACH1 expression across different Pam50 categories, TCGA breast cancer expression and clinical data were accessed and processed using the R package "TCGAbiolinks" (installed through Bioconductor.org). This analysis was done solely on cases for which Pam50 classification information was available (total of 522 cases: 98 basal, 58 Her2-enriched, 231 luminal-A, 127 luminal-B, 8 normal-like). Statistical significance of differential BACH1 expression between different PAM50 subgroups, as well as TNBC vs. Non-TNBC, was determined by Student's t-test (p<0.05).

Comparison of BACH1 expression levels in different cancer types was conducted based on RNA-seq values (log 2) of BACH1 in the provisional TCGA data sets. All cases (complete and incomplete) were used for each cancer type. Genes that are negatively correlated with BACH1 were determined based on a Spearman coefficient cut-off of ±0.3. These selected genes then were subjected to KEGG pathway enrichment analysis either by DAVID (found on the world wide web at david.ncifcrf.gov) or by the R package "GOseq" (found on the world wide web at bioconductor.org).

The frequency of tumors that have upregulated BACH1 expression with respect to their matched healthy tissue was determined using the online tool BioXpress (found on the world wide web at hive.biochemistry.gwu.edu)[1]. Only those TCGA samples that have a matched normal tissue expression data were used for this analysis.

The clinical data sets including METABRIC, GSE2034, GSE1121 were processed according to a gene-centered platform[4].

Q. Metabolomics Profiling

As previously reported with metabolomics profiling, 2 million cells were harvested per replicate and flash-frozen[1]. For polar metabolites, cell pellets were extracted in 40:40:20 acetonitrile/methanol/water including 10 nM D3-15N-serine (CIL) as an internal standard. Insoluble debris was separated by centrifugation at 13,000 rpm for 10 min. Aliquots of extracts were then injected into an Agilent 6460 or 6430 QQQ-LC/MS/MS. Separation of metabolites was achieved using normal-phase chromatography with a Luna 5 mm $NH_2$ column (Phenomenex) using a mobile phase (Buffer A, acetonitrile, followed with Buffer B, 95:5 water/acetonitrile) with the modifiers 0.1% formic acid or 0.2% ammonium hydroxide with 50 mM ammonium acetate for positive and negative ionization mode, respectively. Each run used the same flow: 100% A at 0.2 mL/min for 5 min, followed by a gradient starting at 0% B and linearly increasing to 100% B in 15 min with a flow rate of 0.7 mL/min, succeeded by an isocratic gradient of 100% B for 5 min at 0.7 mL/min before equilibrating for 5 min with 0% B at 0.7 mL/min.

For nonpolar metabolites, cell pellets were extracted in 3 ml of 2:1 chloroform/methanol and 1 ml of PBS along with internal standards dodecylglycerol (10 nmol, Santa Cruz Biotechnology) and pentadecanoic acid (10 nmol, Sigma-Aldrich). Organic and aqueous layers were separated via centrifugation (1000×g for 5 min) and the organic layer collected, dried under nitrogen and dissolved in 120 μl chloroform. For nonpolar metabolites, metabolomes were separated using reverse-phase chromatography with a Luna C5 column (50 mm×4.6 mm with 5 □m diameter particles, Phenomenex). Mobile phase A was a 95:5 ratio of water/methanol and mobile phase B was a 60:35:5 ratio of 2-propanol/methanol/water. Solvent modifiers 0.1% formic acid with 5 mM ammonium formate and 0.1% ammonium hydroxide were used in both positive and negative ionization modes, respectively. The flow rate started at 0.1 ml/min for 5 min to alleviate backpressure associated with injecting chloroform. The gradient began at 0% B and increased linearly to 100% B over the course of 45 min at a flow rate of 0.4 ml/min, followed by an isocratic gradient of 100% B for 17 min at 0.5 ml/min before equilibrating for 8 min at 0% B with a flow rate of 0.5 ml/min.

MS analysis was performed via an electrospray ionization (ESI) source on an Agilent 6430 or 6460 QQQ LC-MS/MS (Agilent Technologies). The capillary voltage was set to 3.0 kV, and the fragmentor voltage to 100 V. The drying gas temperature was 350° C., flow rate was 10 l/min, and nebulizer pressure was 35 psi. Metabolites were identified by SRM of the transition from precursor to product ions at associated optimized collision energies and retention times as previously described[2,3]. Metabolites were quantified by integrating the area under the curve, and then normalized to internal standard values.

TABLE 1

Co-expression correlations of ETC genes enriched in Oxidative phosphorylation pathway with BACH1 in various cancer types

| Cancers | Correlated genes | Cytoband | Pearson's coefficiency | Spearman's coefficiency |
|---|---|---|---|---|
| Breast cancer (TCGA, provisional) | COX6C | 8q22.2 | −0.31 | −0.44 |
| | COX7A2 | 6q12 | −0.35 | −0.40 |
| | COX7C | 5q14 | −0.40 | −0.44 |
| | COX17 | 3q13.33 | −0.44 | −0.56 |
| | COX5B | 2q11.2 | −0.36 | −0.43 |
| | COX6B1 | 19q13.1 | −0.32 | −0.41 |
| | COX4I1 | 16q24.1 | −0.33 | −0.36 |
| | COX6A1 | 12q24.2 | −0.46 | −0.55 |
| | COX14 | 12q13.12 | −0.43 | −0.49 |
| | COX8A | 11q12-q13 | −0.37 | −0.48 |
| | ATP5I | 4p16.3 | −0.41 | −0.51 |
| | ATP5D | 19p13.3 | −0.38 | −0.51 |
| | ATP5G2 | 12q13.13 | −0.47 | −0.51 |
| | ATPIF1 | 1p35.3 | −0.44 | −0.50 |
| | ATP6V0C | 16p13.3 | −0.39 | −0.45 |
| | ATP6V1F | 7q32 | −0.34 | −0.43 |
| | ATP6V0B | 1p32.3 | −0.35 | −0.43 |
| | ATPAF2 | 17p11.2 | −0.36 | −0.42 |
| | ATP6V0E2 | 7q36.1 | −0.33 | −0.40 |
| | ATP5SL | 19q13.2 | −0.32 | −0.40 |
| | ATP5H | 17q25 | −0.31 | −0.39 |
| | ATP6AP1 | Xq28 | −0.33 | −0.38 |
| | ATP5E | 20q13.32 | −0.33 | −0.37 |
| | ATP13A1 | 19p13.11 | −0.31 | −0.35 |
| | UQCR11 | 19p13.3 | −0.42 | −0.50 |
| | UQCRQ | 5q31.1 | −0.35 | −0.41 |
| | UQCRC1 | 3p21.3 | −0.35 | −0.40 |
| | UQCR10 | 22q12.2 | −0.34 | −0.39 |
| | NDUFA7 | 19p13.2 | −0.48 | −0.62 |
| | NDUFA2 | 5q31.2 | −0.49 | −0.59 |
| | NDUFA13 | 19p13.2 | −0.44 | −0.56 |
| | NDUFB10 | 16p13.3 | −0.47 | −0.56 |
| | NDUFS8 | 11q13 | −0.39 | −0.54 |
| | NDUFAF3 | 3p21.31 | −0.45 | −0.51 |
| | NDUFA3 | 19q13.42 | −0.40 | −0.51 |
| | NDUFS7 | 19p13.3 | −0.42 | −0.51 |
| | NDCFB7 | 19p13.12 | −0.41 | −0.51 |
| | NDUFB11 | Xp11.23 | −0.37 | −0.48 |
| | NDUFA8 | 9q33.2 | −0.39 | −0.47 |
| | NDUFB2 | 7q34 | −0.40 | −0.47 |
| | NDUFC1 | 4q31.1 | −0.40 | −0.47 |
| | NDUFB8 | 10q24.31 | −0.43 | −0.47 |
| | NDUFS6 | 5p15.33 | −0.36 | −0.46 |
| | NDUFS3 | 11p11.11 | −0.39 | −0.46 |
| | NDUFA11 | 19p13.3 | −0.38 | −0.45 |
| | NDUFB6 | 9p21.1 | −0.38 | −0.42 |
| | NDUFA1 | Xq24 | −0.37 | −0.41 |
| | NDUFB1 | 14q32.12 | −0.35 | −0.41 |
| | NDUFAB1 | 16p12.2 | −0.37 | −0.40 |
| | NDUFV2 | 18p11.22 | −0.33 | −0.37 |
| | NDUFB4 | 3q13.33 | −0.32 | −0.36 |
| | NDUFV1 | 11q13 | −0.33 | −0.33 |
| | NDUFAF2 | 5q12.1 | −0.31 | −0.32 |
| | NDUFA10 | 2q37.3 | −0.32 | −0.32 |
| | NDUFAF1 | 15q11.2-q21.3 | −0.32 | −0.32 |
| Liver hepatocarcinoma (TCGA, provisional) | COX7B | Xq21.1 | −0.35 | −0.43 |
| | COX6C | 8q22.2 | −0.34 | −0.43 |
| | COX7C | 5q14 | −0.37 | −0.44 |
| | COX17 | 3q13.33 | −0.41 | −0.49 |
| | COX5B | 2q11.2 | −0.38 | −0.50 |
| | COX4I1 | 16q24.1 | −0.36 | −0.49 |
| | COX5A | 15q24.1 | −0.31 | −0.38 |
| | COX16 | 14q24.2 | −0.31 | −0.41 |
| | COX6A1 | 12q24.2\|12q24.2 | −0.39 | −0.51 |
| | COX14 | 12q13.12 | −0.35 | −0.40 |
| | COX8A | 11q12-q13 | −0.40 | −0.49 |
| | UQCRB | 8q22 | −0.36 | −0.47 |
| | UQCRQ | 5q31.1 | −0.37 | −0.47 |
| | UQCRC1 | 3p21.3 | −0.32 | −0.38 |
| | UQCR10 | 22q12.2 | −0.38 | −0.46 |
| | UQCR11 | 19p13.3 | −0.41 | −0.56 |
| | ATP6AP1 | Xq28 | −0.30 | −0.38 |
| | ATP6V1F | 7q32 | −0.32 | −0.39 |
| | ATP5J2 | 7q22.1 | −0.35 | −0.47 |
| | ATP6V0E1 | 5q35.1 | −0.34 | −0.40 |

TABLE 1-continued

Co-expression correlations of ETC genes enriched in Oxidative phosphorylation pathway with BACH1 in various cancer types

| Cancers | Correlated genes | Cytoband | Pearson's coefficiency | Spearman's coefficiency |
|---|---|---|---|---|
| | ATP5I | 4p16.3 | −0.35 | −0.49 |
| | ATP5E | 20q13.32 | −0.35 | −0.48 |
| | ATPIF1 | 1p35.3 | −0.34 | −0.37 |
| | ATP5D | 19p13.3 | −0.33 | −0.46 |
| | ATP5H | 17q25 | −0.36 | −0.45 |
| | ATP5G2 | 12q13.13 | −0.36 | −0.48 |
| | ATP5L | 11q23.3 | −0.37 | −0.40 |
| | NDUFA1 | Xq24 | −0.41 | −0.51 |
| | NDUFB11 | Xp11.23 | −0.37 | −0.52 |
| | NDUFA8 | 9q33.2 | −0.36 | −0.48 |
| | NDUFB6 | 9p21.1 | −0.40 | −0.44 |
| | NDUFB9 | 8q13.3 | −0.35 | −0.49 |
| | NDUFB2 | 7q34 | −0.41 | −0.53 |
| | NDUFA4 | 7p21.3 | −0.39 | −0.47 |
| | NDUFA2 | 5q31.2 | −0.41 | −0.54 |
| | NDUFAF2 | 5q12.1 | −0.31 | −0.37 |
| | NDUFS4 | 5q11.1 | −0.37 | −0.46 |
| | NDUFS6 | 5p15.33 | −0.38 | −0.52 |
| | NDUFC1 | 4q31.1 | −0.34 | −0.47 |
| | NDUFB4 | 3q13.33 | −0.40 | −0.48 |
| | NDUFAF3 | 3p21.31 | −0.35 | −0.42 |
| | NDUFB3 | 2q31.3 | −0.31 | −0.40 |
| | NDUFA6 | 22q13.2 | −0.34 | −0.44 |
| | NDUFS5 | 1p34.2-p33 | −0.38 | −0.53 |
| | NDUFA3 | 19q13.42 | −0.38 | −0.55 |
| | NDUFS7 | 19p13.3 | −0.38 | −0.51 |
| | NDUFA11 | 19p13.3 | −0.40 | −0.55 |
| | NDUFA7 | 19p13.2 | −0.43 | −0.52 |
| | NDUFA13 | 19p13.2 | −0.38 | −0.58 |
| | NDUFB10 | 16p13.3 | −0.34 | −0.42 |
| | NDUFAB1 | 16p12.2 | −0.33 | −0.38 |
| | NDUFB1 | 14q32.12 | −0.37 | −0.54 |
| | NDUFA12 | 12q22 | −0.39 | −0.46 |
| | NDUFC2 | 11q14.1 | −0.31 | −0.39 |
| | NDUFV1 | 11q13 | −0.31 | −0.42 |
| | NDUFS8 | 11q13 | −0.36 | −0.57 |
| | NDUFS3 | 11p11.11 | −0.38 | −0.49 |
| Prostate adeno-carcinoma (TCGA, provisional) | COX7B | Xq21.1 | −0.51 | −0.56 |
| | COX6C | 8q22.2 | −0.46 | −0.58 |
| | COX19 | 7p22.3 | −0.40 | −0.46 |
| | COX7A2 | 6q12 | −0.50 | −0.53 |
| | COX7C | 5q14 | −0.50 | −0.52 |
| | COX17 | 3q13.33 | −0.45 | −0.52 |
| | COX5B | 2q11.2 | −0.55 | −0.62 |
| | COX4I2 | 20q11.21 | −0.39 | −0.42 |
| | COX6B1 | 19q13.1 | −0.55 | −0.64 |
| | COX4I1 | 16q24.1 | −0.51 | −0.54 |
| | COX5A | 15q24.1 | −0.40 | −0.39 |
| | COX6A1 | 12q24.2\|12q4.2 | −0.49 | −0.52 |
| | COX14 | 12q13.12 | −0.56 | −0.63 |
| | COX8A | 11q12-q13 | −0.58 | −0.61 |
| | UQCRBP1 | Xp11.21 | −0.36 | −0.40 |
| | UQCRB | 8q22 | −0.43 | −0.53 |
| | UQCRQ | 5q31.1 | −0.51 | −0.57 |
| | UQCRC1 | 3p21.3 | −0.53 | −0.56 |
| | UQCR10 | 22q12 2 | −0.53 | −0.56 |
| | UQCRHL | 1p36.21 | −0.44 | −0.46 |
| | UQCRH | 1p34.1 | −0.48 | −0.49 |
| | UQCR11 | 19p13.3 | −0.56 | −0.64 |
| | ATP6V1F | 7q32 | −0.43 | −0.50 |
| | ATP5J2 | 7q22.1 | −0.44 | −0.56 |
| | ATP6V0E1 | 5q35.1 | −0.45 | −0.45 |
| | ATP5I | 4p16.3 | −0.55 | −0.61 |
| | ATP5G3 | 2q31.1 | −0.38 | −0.42 |
| | ATP6V1E1 | 22q11.1 | −0.43 | −0.46 |
| | ATP5O | 21q22.11 | −0.49 | −0.51 |
| | ATP5J | 21q21.1 | −0.45 | −0.51 |
| | ATP5E | 20q13.32 | −0.54 | −0.62 |
| | ATPIF1 | 1p35.3 | −0.56 | −0.57 |
| | ATP6V0B | 1p32.3 | −0.48 | −0.48 |
| | ATP5SL | 19q13.2 | −0.39 | −0.44 |
| | ATP5D | 19p13.3 | −0.53 | −0.63 |
| | ATP13A1 | 19p13.11 | −0.33 | −0.32 |
| | ATP5H | 17q25 | −0.47 | −0.50 |
| | ATP5G1 | 17q21.32 | −0.53 | −0.57 |
| | ATPAF2 | 17p11.2 | −0.45 | −0.46 |
| | ATP6V0D1 | 16q22.1 | −0.38 | −0.33 |
| | ATP6V0C | 16p13.3 | −0.52 | −0.53 |
| | NDUFA1 | Xq24 | −0.55 | −0.60 |
| | NDUFB11 | Xp11.23 | −0.56 | −0.63 |
| | NDUFA8 | 9q33.2 | −0.55 | −0.58 |
| | NDUFB6 | 9p21.1 | −0.37 | −0.43 |
| | NDUFB9 | 8q13.3 | −0.43 | −0.53 |
| | NDUFB2 | 7q34 | −0.53 | −0.58 |
| | NDUFA4 | 7p21.3 | −0.40 | −0.45 |
| | NDUFA2 | 5q31.2 | −0.55 | −0.59 |
| | NDUFAF2 | 5q12.1 | −0.48 | −0.48 |
| | NDUFS4 | 5q11.1 | −0.42 | −0.41 |
| | NDUFS6 | 5p15.33 | −0.54 | −0.63 |
| | NDUFC1 | 4q31.1 | −0.52 | −0.56 |
| | NDUFAF3 | 3p21.31 | −0.47 | −0.51 |
| | NDUFA10 | 2q37.3 | −0.45 | −0.46 |
| | NDUFB3 | 2q31.3 | −0.41 | −0.43 |
| | NDUFA6 | 22q13.2 | −0.56 | −0.61 |
| | NDUFV3 | 21q22.3 | −0.43 | −0.47 |
| | NDUFAF5 | 20p12.1 | −0.52 | −0.55 |
| | NDUFS5 | 1p34.2-p33 | −0.56 | −0.65 |
| | NDUFA3 | 19q13.42 | −0.52 | −0.60 |
| | NDUFS7 | 19p13.3 | −0.58 | −0.65 |
| | NDUFA11 | 19p13.3 | −0.55 | −0.67 |
| | NDUFA7 | 19p13.2 | −0.52 | −0.58 |
| | NDUFA13 | 19p13.2 | −0.55 | −0.67 |
| | NDUFB7 | 19p13.12 | −0.54 | −0.65 |
| | NDUFV2 | 18p11.22 | −0.38 | −0.36 |
| | NDUFB10 | 16p13.3 | −0.55 | −0.60 |
| | NDUFAB1 | 16p12.2 | −0.48 | −0.49 |
| | NDUFAF1 | 15q11.2-q21.3 | −0.36 | −0.38 |
| Skin cutaneous melanoma (TCGA, provisional) | COX6C | 8q22.2 | −0.31 | −0.41 |
| | COX7C | 5q14 | −0.33 | −0.38 |
| | COX5B | 2q11.2 | −0.40 | −0.58 |
| | COX6B1 | 19q13.1 | −0.41 | −0.60 |
| | COX4I1 | 16q24.1 | −0.38 | −0.50 |
| | COX5A | 15q24.1 | −0.42 | −0.55 |
| | COX6A1 | 12q24.2\|12q24.2 | −0.44 | −0.61 |
| | COX14 | 12q13.12 | −0.38 | −0.46 |
| | COX8A | 11q12-q13 | −0.42 | −0.55 |
| | ATP6AP1 | Xq28 | −0.36 | −0.46 |
| | ATP6V1F | 7q32 | −0.43 | −0.56 |
| | ATP5J2 | 7q22.1 | −0.34 | −0.41 |
| | ATP5I | 4p16.3 | −0.34 | −0.48 |
| | ATP5G3 | 2q31.1 | −0.35 | −0.41 |
| | ATP13A2 | 1p36 | −0.38 | −0.45 |
| | ATP6V0B | 1p32.3 | −0.34 | −0.47 |
| | ATP5SL | 19q13.2 | −0.31 | −0.39 |
| | ATP5D | 19p13.3 | −0.35 | −0.49 |
| | ATP5H | 17q25 | −0.40 | −0.55 |
| | ATP5G1 | 17q21.32 | −0.42 | −0.55 |
| | ATP6V0A1 | 17q21 | −0.35 | −0.41 |
| | ATPAF2 | 17p11.2 | −0.33 | −0.42 |
| | ATP6V0D1 | 16q22.1 | −0.35 | −0.45 |
| | ATP6V0C | 16p13.3 | −0.43 | −0.62 |
| | ATP5G2 | 12q13.13 | −0.38 | −0.50 |
| | UQCC2 | 6p21.31 | −0.35 | −0.48 |
| | UQCRQ | 5q31.1 | −0.39 | −0.51 |
| | UQCRC1 | 3p21.3 | −0.41 | −0.52 |
| | UQCR10 | 22q12.2 | −0.42 | −0.55 |
| | UQCR11 | 19p13.3 | −0.34 | −0.39 |
| | UQCC3 | 11q12.3 | −0.36 | −0.48 |
| | NDUFA1 | Xq24 | −0.31 | −0.50 |
| | NDUFB11 | Xp11.23 | −0.40 | −0.53 |
| | NDUFA8 | 9q33.2 | −0.42 | −0.58 |
| | NDUFB9 | 8q13.3 | −0.32 | −0.45 |
| | NDUFB2 | 7q34 | −0.32 | −0.42 |
| | NDUFA2 | 5q31.2 | −0.36 | −0.48 |
| | NDUFS6 | 5p15.33 | −0.40 | −0.56 |

TABLE 1-continued

Co-expression correlations of ETC genes enriched in Oxidative phosphorylation pathway with BACH1 in various cancer types

| Cancers | Correlated genes | Cytoband | Pearson's coefficiency | Spearman's coefficiency |
|---|---|---|---|---|
| | NDUFC1 | 4q31.1 | −0.31 | −0.39 |
| | NDUFB4 | 3q13.33 | −0.41 | −0.58 |
| | NDUFAF3 | 3p21.31 | −0.37 | −0.51 |
| | NDUFV3 | 21q22.3 | −0.33 | −0.38 |
| | NDUFS2 | 1q23 | −0.35 | −0.44 |
| | NDUFS5 | 1p34.2-p33 | −0.35 | −0.46 |
| | NDUFA3 | 19q13.42 | −0.40 | −0.59 |
| | NDUFS7 | 19p13.3 | −0.42 | −0.59 |
| | NDUFA11 | 19p13.3 | −0.37 | −0.49 |
| | NDUFA7 | 19p13.2 | −0.38 | −0.53 |
| | NDUFA13 | 19p13.2 | −0.36 | −0.54 |
| | NDUFB7 | 19p13.12 | −0.41 | −0.58 |
| | NDUFB10 | 16p13.3 | −0.43 | −0.57 |
| | NDUFB1 | 14q32.12 | −0.34 | −0.48 |
| | NDUFA12 | 12q22 | −0.33 | −0.43 |
| | NDUFA9 | 12p13.3 | −0.33 | −0.44 |
| | NDUFV1 | 11q13 | −0.34 | −0.55 |
| | NDUFS8 | 11q13 | −0.37 | −0.58 |
| | NDUFS3 | 11p11.11 | −0.39 | −0.51 |
| | NDUFB8 | 10q24.31 | −0.32 | −0.44 |
| Ovarian serous Cystadeno-carcinoma (TCGA, provisional) | COX5B | 2q11.2 | −0.32 | −0.39 |
| | COX4I1 | 16q24.1 | −0.32 | −0.38 |
| | COX5A | 15q24.1 | −0.32 | −0.36 |
| | COX8A | 11q12-q13 | −0.34 | −0.37 |
| | UQCRB | 8q22 | −0.32 | −0.32 |
| | UQCC3 | 11q12.3 | −0.34 | −0.38 |
| | ATP5J2 | 7q22.1 | −0.35 | −0.40 |
| | ATP5G3 | 2q31.1 | −0.33 | −0.37 |
| | ATP5F1 | 1p13.2 | −0.33 | −0.39 |
| | ATP5H | 17q25 | −0.32 | −0.35 |
| | ATP5G2 | 12q13.13 | −0.33 | −0.32 |
| | NDUFA1 | Xq24 | −0.33 | −0.37 |
| | NDUFA8 | 9q33.2 | −0.35 | −0.40 |
| | NDUFA2 | 5q31.2 | −0.34 | −0.38 |
| | NDUFS6 | 5p15.33 | −0.34 | −0.41 |
| | NDUFV2 | 18p11.22 | −0.31 | −0.39 |
| | NDUFAB1 | 16p12.2 | −0.31 | −0.40 |
| | NDUFB1 | 14q32.12 | −0.34 | −0.41 |
| | NDUFV1 | 11q13 | −0.32 | −0.32 |
| | NDUFS8 | 11q13 | −0.35 | −0.39 |
| | NDUFS3 | 11p11.11 | −0.37 | −0.44 |
| Lung adeno-carcinoma (TCGA, provisional) | ATPIF1 | 1p35.3 | −0.34 | −0.42 |
| | NDUFAF3 | 3p21.31 | −0.31 | −0.36 |
| | NDUFS7 | 19p13.3 | −0.31 | −0.32 |
| | NDUFV1 | 11q13 | −0.30 | −0.44 |
| Lung squamous (TCGA, provisional) | COX8A | 11q12-q13 | −0.31 | −0.34 |
| Pancreas adeno-carcinoma (TCGA, provisional) | COX7B | Xq21.1 | −0.37 | −0.45 |
| | COX6C | 8q22.2 | −0.36 | −0.39 |
| | COX19 | 7p22.3 | −0.39 | −0.42 |
| | COX7A2 | 6q12 | −0.34 | −0.36 |
| | COX7C | 5q14 | −0.42 | −0.47 |
| | COX17 | 3q13.33 | −0.39 | −0.42 |
| | COX5B | 2q11.2 | −0.44 | −0.52 |
| | COX4I2 | 20q11.21 | −0.34 | −0.32 |
| | COX6B1 | 19q13.1 | −0.33 | −0.41 |
| | COX4I1 | 16q24.1 | −0.39 | −0.43 |
| | COX5A | 15q24.1 | −0.36 | −0.39 |
| | COX16 | 14q24.2 | −0.42 | −0.49 |
| | COX6A1 | 12q24.2\|12q24.2 | −0.39 | −0.44 |
| | COX14 | 12q13.12 | −0.46 | −0.40 |
| | COX8A | 11q12-q13 | −0.57 | −0.60 |
| | UQCRB | 8q22 | −0.36 | −0.35 |
| | UQCC2 | 6p21.31 | −0.43 | −0.49 |
| | UQCRQ | 5q31.1 | −0.41 | −0.53 |
| | UQCRC1 | 3p21.3 | −0.33 | −0.43 |
| | UQCR10 | 22q12.2 | −0.46 | −0.51 |
| | UQCC1 | 20q11.22 | −0.43 | −0.42 |
| | UQCRFS1 | 19q12 | −0.32 | −0.37 |
| | UQCR11 | 19p13.3 | −0.50 | −0.59 |
| | UQCC3 | 11q12.3 | −0.41 | −0.52 |
| | ATP6AP1 | Xq28 | −0.39 | −0.32 |
| | ATP6V0E2-AS1 | 7q36.1 | −0.39 | −0.41 |
| | ATP6V0E2 | 7q36.1 | −0.43 | −0.50 |
| | ATP5J2 | 7q22.1 | −0.37 | −0.46 |
| | ATP6V1E2 | 2p21 | −0.37 | −0.33 |
| | ATP5J | 21q21.1 | −0.31 | −0.32 |
| | ATP5E | 20q13.32 | −0.44 | −0.46 |
| | ATPIF1 | 1p35.3 | −0.45 | −0.52 |
| | ATPAF1 | 1p33 | −0.36 | −0.31 |
| | ATP6V0B | 1p32.3 | −0.32 | −0.55 |
| | ATP1A1-AS1 | 1p13.1 | −0.40 | −0.36 |
| | ATP5SL | 19q13.2 | −0.34 | −0.38 |
| | ATP5D | 19p13.3 | −0.45 | −0.60 |
| | ATP13A1 | 19p13.11 | −0.45 | −0.42 |
| | ATP5A1 | 18q21 | −0.38 | −0.31 |
| | ATP5H | 17q25 | −0.31 | −0.36 |
| | ATP5G1 | 17q21.32 | −0.46 | −0.55 |
| | ATP2A3 | 17p13.3 | −0.38 | −0.36 |
| | ATPAF2 | 17p11.2 | −0.53 | −0.47 |
| | ATP6V0C | 16p13.3 | −0.39 | −0.39 |
| | ATP5G2 | 12q13.13 | −0.45 | −0.47 |
| | NDUFA1 | Xq24 | −0.46 | −0.49 |
| | NDUFB11 | Xp11.23 | −0.49 | −0.62 |
| | NDUFA8 | 9q33.2 | −0.43 | −0.44 |
| | NDUFB6 | 9p21.1 | −0.36 | −0.38 |
| | NDCFB2 | 7q34 | −0.52 | −0.59 |
| | NDUFB2-AS1 | 7q34 | −0.43 | −0.48 |
| | NDUFA2 | 5q31.2 | −0.48 | −0.55 |
| | NDUFAF2 | 5q12.1 | −0.34 | −0.35 |
| | NDCFS6 | 5p15.33 | −0.38 | −0.59 |
| | NDUFC1 | 4q31.1 | −0.50 | −0.56 |
| | NDUFAF3 | 3p21.31 | −0.47 | −0.51 |
| | NDUFAF5 | 20p12.1 | −0.35 | −0.34 |
| | NDUFA3 | 19q13.42 | −0.41 | −0.52 |
| | NDUFS7 | 19p13.3 | −0.54 | −0.56 |
| | NDUFA11 | 19p13.3 | −0.42 | −0.53 |
| | NDUFA7 | 19p13.2 | −0.49 | −0.55 |
| | NDUFA13 | 19p13.2 | −0.48 | −0.55 |
| | NDUFB7 | 19p13.12 | −0.52 | −0.58 |
| | NDUFB10 | 16p13.3 | −0.42 | −0.49 |
| Pancreas adeno-carcinoma (TCGA, provisional) | NDUFAB1 | 16p12.2 | −0.38 | −0.42 |
| | NDUFB1 | 14q32.12 | −0.38 | −0.55 |
| | NDUFC2 | 11q14.1 | −0.42 | −0.43 |
| | NDUFV1 | 11q13 | −0.52 | −0.58 |
| | NDUFS8 | 11q3 | −0.50 | −0.57 |
| | NDUFS3 | 11p11.11 | −0.49 | −0.55 |
| | NDUFB8 | 10q24.31 | −0.45 | −0.47 |
| Colorectal adeno-carcinoma (TCGA, Provisional) | COX7B | Xq21.1 | −0.34 | −0.44 |
| | COX7A2 | 6q12 | −0.33 | −0.36 |
| | COX7C | 5q14 | −0.34 | −0.34 |
| | COX17 | 3q13.33 | −0.33 | −0.35 |
| Colorectal adeno-carcinoma (TCGA, Provisional) | COX5B | 2q11.2 | −0.41 | −0.52 |
| | COX6B1 | 19q13.1 | −0.33 | −0.48 |
| | COX4I1 | 16q24.1 | −0.43 | −0.50 |
| | COX5A | 15q24.1 | −0.38 | −0.38 |
| | COX16 | 14q24.2 | −0.32 | −0.31 |
| | COX6A1 | 12q24.2\|12q24.2 | −0.38 | −0.41 |
| | COX8A | 11q12-q13 | −0.38 | −0.41 |
| | UQCRC1 | 3p21.3 | −0.33 | −0.32 |
| | ATP6V1F | 7q32 | −0.31 | −0.35 |
| | ATP5J2 | 7q22.1 | −0.41 | −0.50 |
| | ATP5G3 | 2q31.1 | −0.30 | −0.33 |
| | ATP5E | 20q13.32 | −0.30 | −0.32 |
| | ATPIF1 | 1p35.3 | −0.42 | −0.42 |
| | ATP5G1 | 17q21.32 | −0.42 | −0.43 |
| | ATP5G2 | 12q13.13 | −0.34 | −0.35 |
| | ATP5L | 11q23.3 | −0.34 | −0.40 |
| | ATP5C1 | 10p15.1 | −0.34 | −0.39 |
| | NDUFA1 | Xq24 | −0.35 | −0.40 |
| | NDUFB11 | Xp11.23 | −0.41 | −0.47 |
| | NDUFA8 | 9q33.2 | −0.40 | −0.43 |

TABLE 1-continued

Co-expression correlations of ETC genes enriched in Oxidative phosphorylation pathway with BACH1 in various cancer types

| Cancers | Correlated genes | Cytoband | Pearson's coefficiency | Spearman's coefficiency |
|---|---|---|---|---|
| | NDUFB6 | 9p21.1 | −0.34 | −0.43 |
| | NDUFB9 | 8q13.3 | −0.31 | −0.34 |
| | NDUFB2 | 7q34 | −0.39 | −0.47 |
| | NDUFAF4 | 6q16.1 | −0.31 | −0.31 |
| | NDUFA2 | 5q31.2 | −0.38 | −0.44 |
| | NDUFAF2 | 5q12.1 | −0.35 | −0.37 |
| | NDUFC1 | 4q31.1 | −0.36 | −0.38 |
| | NDUFB4 | 3q13.33 | −0.33 | −0.35 |
| | NDUFAF3 | 3p21.31 | −0.31 | −0.33 |
| | NDUFA10 | 2q37.3 | −0.35 | −0.34 |
| | NDUFS5 | 1p34.2-p33 | −0.31 | −0.36 |
| | NDUFS7 | 19p13.3 | −0.36 | −0.42 |
| | NDUFA7 | 19p13.2 | −0.42 | −0.46 |
| | NDUFA13 | 19p13.2 | −0.30 | −0.49 |
| | NDUFB7 | 19p13.12 | −0.35 | −0.46 |
| | NDUFB10 | 16p13.3 | −0.30 | −0.41 |
| | NDUFAB1 | 16p12.2 | −0.37 | −0.44 |
| | NDUFB1 | 14q32.12 | −0.36 | −0.43 |
| | NDUFC2 | 11q14.1 | −0.33 | −0.36 |
| | NDUFB8 | 10q24.31 | −0.41 | −0.43 |
| | NDUFV1 | 11q13 | −0.32 | −0.33 |
| | NDUFS8 | 11q13 | −0.38 | −0.45 |
| | NDUFS3 | 11p11.11 | −0.39 | −0.43 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

1. DeBerardinis, R. J., Lum, J. J., Hatzivassiliou, G. & Thompson, C. B. The biology of cancer: metabolic reprogramming fuels cell growth and proliferation. Cell Metab. 7, 11-20(2008).
2. Oyake, T. et al. Bach proteins belong to a novel family of BTB-basic leucine zipper transcription factors that interact with MafK and regulate transcription through the NF-E2 site. Mol. Cell. Biol. 16, 6083-6095 (1996).
3. Ogawa, K. et al. Heme mediates derepression of Maf recognition element through direct binding to transcription repressor Bach. EMBO J. 20, 2835-2843 (2001).
4. Foretz, M., Guigas, B., Bertrand, L., Pollak, M. & Viollet, B. Metformin: from mechanisms of action to therapies. Cell Metab. 20, 953-966 (2014).
5. Stockmans, G., Deraedt, K., Wildiers, H., Moerman, P. & Paridaens, R. Triple-negative breast cancer. Curr. Opin. Oncol. 20, 614-620 (2008).
6. Yun, J. et al. Signalling pathway for RKIP and Let-7 regulates and predicts metastatic breast cancer. EMBO J. 30, 4500-4514 (2011).
7. Lee, U. et al. A prognostic gene signature for metastasis-free survival of triple negative breast cancer patients. PloS One 8, e82125 (2013).
8. Bach1 deficiency and accompanying overexpression of heme oxygenase-1 do not influence aging or tumorigenesis in mice. |PubFacts.com. Available at: https://www.pubfacts.com/detail/25050144/Bach1-deficiency-and-accompanying-overexpression-of-heme-oxygenase-1-do-not-influence-aging-or-tumor. (Accessed: 3 Mar. 2017)
9. Minn, A. J. et al. Genes that mediate breast cancer metastasis to lung. Nature 436, 518-524(2005).
10. Kim, J., Tchernyshyov, I., Semenza, G. L. & Dang, C. V. HIF-1-mediated expression of pyruvate dehydrogenase kinase: a metabolic switch required for cellular adaptation to hypoxia. Cell Metab. 3, 177-185 (2006).
11. Wheaton, W. W. et al. Metformin inhibits mitochondrial complex I of cancer cells to reduce tumorigenesis. eLife 3, e02242 (2014).
12. Shaw, R. J. et al. The kinase LKB1 mediates glucose homeostasis in liver and therapeutic effects of metformin. Science 310, 1642-1646 (2005).
13. Gui, D. Y. et al. Environment Dictates Dependence on Mitochondrial Complex I for NAD+ and Aspartate Production and Determines Cancer Cell Sensitivity to Metformin. Cell Metab. 24, 716-727 (2016).
14. Chandel, N. S. Mitochondria and cancer. Cancer Metab. 2, 8 (2014).
15. Weinberg, S. E. & Chandel, N. S. Targeting mitochondria metabolism for cancer therapy. Nat. Chem. Biol. 11, 9-15 (2015).
16. Peterson, A., Bossenmaier, I., Cardinal, R. & Watson, C. J. Hematin treatment of acute porphyria. Early remission of an almost fatal relapse. JAMA 235, 520-522 (1976).
17. Findlay, G. H. EPIDERMAL HAEMATIN ENZYMES AND THE METABOLISM OF PORPHYRIC EPIDERMIS. South Afr. J. Lab. Clin. Med. Suid-Afr. Tydskr. Vir Lab.-En Kliniekw. 14, 241-244 (1963).
18. Dhar, G. J., Bossenmaier, I., Petryka, Z. J., Cardinal, R. & Watson, C. J. Effects of hematin in hepatic porphyria. Further studies. Ann. Intern. Med. 83, 20-30 (1975).
19. Green, J. E. et al. The C3(1)/SV40 T-antigen transgenic mouse model of mammary cancer: ductal epithelial cell targeting with multistage progression to carcinoma. Oncogene 19, 1020-1027 (2000).
20. Dobrolecki, L. E. et al. Patient-derived xenograft (PDX) models in basic and translational breast cancer research. Cancer Metastasis Rev. 35, 547-573 (2016).
21. Birsoy, K. et al. Metabolic determinants of cancer cell sensitivity to glucose limitation and biguanides. Nature 508, 108-112 (2014).
22. Lipner, M. B. et al. Metformin Treatment Does Not Inhibit Growth of Pancreatic Cancer Patient-Derived Xenografts. PloS One 11, e0147113 (2016).
23. Tsilidis, K. K. et al. Metformin does not affect cancer risk: a cohort study in the U.K. Clinical Practice Research Datalink analyzed like an intention-to-treat trial. Diabetes Care 37, 2522-2532 (2014).
24. Lee, J. et al. Network of mutually repressive metastasis regulators can promote cell heterogeneity and metastatic transitions. Proc. Natl. Acad. Sci. U.S.A 111, E364-373 (2014).
25. Wan Q, Dingerdissen H, Fan Y, Gulzar N, Pan Y, Wu T-J, Yang C, Zhang H, and Mazumder R. BioXpress: An integrated RNA-seq derived gene expression database for pan-cancer analysis. Database (Oxford). 2015 Mar. 28. pii: bav019. PMID: 25819073

26. Louie, S. M., Grossman, E. A., Crawford, L. A., Ding, L., Camarda, R., Huffman, T. R., Miyamoto, D. K., Goga, A., Weerapana, E., and Nomura, D. K. (2016) GSTP1 Is a Driver of Triple-Negative Breast Cancer Cell Metabolism and Pathogenicity. *Cell Chem. Biol.* 23, 567-578.

27. Benjamin, D. I., Cozzo, A., Ji, X., Roberts, L. S., Louie, S. M., Mulvihill, M. M., Luo, K., and Nomura, D. K. (2013) Ether lipid generating enzyme AGPS alters the balance of structural and signaling lipids to fuel cancer pathogenicity. *Proc. Natl. Acad. Sci. U.S.A* 110, 14912-14917.

What is claimed is:

1. A method for reducing or ameliorating metformin-resistant triple negative breast cancer (TNBC) tumor growth in a subject comprising administering an effective amount of hemin and metformin to the subject.

2. The method of claim 1, wherein hemin is administered at the same time or prior to metformin.

3. The method of claim 2, wherein hemin and metformin are administered in the same composition.

4. The method of claim 1, wherein the administration is intra-tumoral, intravenous, peri-tumoral, oral, or sub-cutaneous.

5. The method of claim 1, wherein the subject has been determined to have an increased expression of BACH1 in a biological sample from the subject compared to a control.

6. The method of claim 1, wherein the method further comprises determining the level of BACH1 in a biological sample from the subject.

7. The method of claim 1, wherein the method further comprises administration of a further therapeutic agent.

8. The method of claim 7, wherein the further therapeutic agent is ABT-737, ABT-263 (navitoclax), ABT-199 (venetoclax, RG7601, GDC-0199), gambogic acid, 2,3-DCPE, gossypol, (−)-epigallocatechin gallate, nilotinib, AG 1024, HA14-1, obatoclax mesylate, piperlongumine, TW-37, EM20-25, YC137, genasense, oblimersen sodium, desferrioxamine, deferasirox, or combinations thereof.

9. A method for reducing or ameliorating metformin-resistant triple negative breast cancer (TNBC) tumor growth in a subject comprising:
   administering a first therapeutic regimen comprising metformin to a subject determined to have a decreased or substantially the same level of expression of BACH1 relative to a control sample or to a cut-off value; wherein the first therapeutic regimen excludes a BACH1 inhibitor; or
   administering a second therapeutic regimen comprising hemin and metformin to a subject determined to have an increased level of expression of BACH1 relative to a control sample or a cut-off value.

* * * * *

UNITED STATES PATENT AND TRADEMARK OFFICE
CERTIFICATE OF CORRECTION

| | |
|---|---|
| PATENT NO. | : 10,888,569 B1 |
| APPLICATION NO. | : 16/005052 |
| DATED | : January 12, 2021 |
| INVENTOR(S) | : Rosner et al. |

It is certified that error appears in the above-identified patent and that said Letters Patent is hereby corrected as shown below:

In the Specification

On Column 1, Line 7, the paragraph should read as follows:
This invention was made with government support under W81XWH-17-1-0261 awarded by the Defense Advanced Research Projects Agency. The government has certain rights in the invention.

Signed and Sealed this
Twenty-first Day of November, 2023

Katherine Kelly Vidal
*Director of the United States Patent and Trademark Office*